US010047152B2

(12) United States Patent
Orengo et al.

(10) Patent No.: US 10,047,152 B2
(45) Date of Patent: Aug. 14, 2018

(54) HUMAN ANTIBODIES TO FEL D1 AND METHODS OF USE THEREOF

(71) Applicant: Regeneron Pharmaceuticals, Inc., Tarrytown, NY (US)

(72) Inventors: Jamie Orengo, Cortlandt Manor, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 143 days.

(21) Appl. No.: 15/263,848

(22) Filed: Sep. 13, 2016

(65) Prior Publication Data

US 2016/0376358 A1 Dec. 29, 2016

Related U.S. Application Data

(62) Division of application No. 14/732,578, filed on Jun. 5, 2015, now Pat. No. 9,475,869, which is a division of application No. 13/875,401, filed on May 2, 2013, now Pat. No. 9,079,948.

(60) Provisional application No. 61/783,312, filed on Mar. 14, 2013, provisional application No. 61/718,044, filed on Oct. 24, 2012, provisional application No. 61/642,083, filed on May 3, 2012.

(51) Int. Cl.
| | |
|---|---|
| *C12N 1/20* | (2006.01) |
| *C12N 5/00* | (2006.01) |
| *C12N 5/02* | (2006.01) |
| *C12N 5/07* | (2010.01) |
| *C12N 5/16* | (2006.01) |
| *C07K 16/18* | (2006.01) |
| *A61K 39/395* | (2006.01) |
| *A61K 45/06* | (2006.01) |
| *C07K 16/46* | (2006.01) |
| *A61K 39/12* | (2006.01) |
| *A61K 39/35* | (2006.01) |
| *A61K 39/00* | (2006.01) |

(52) U.S. Cl.
CPC .............. *C07K 16/18* (2013.01); *A61K 39/12* (2013.01); *A61K 39/35* (2013.01); *A61K 39/3955* (2013.01); *A61K 45/06* (2013.01); *C07K 16/468* (2013.01); *A61K 2039/505* (2013.01); *A61K 2039/507* (2013.01); *A61K 2039/5252* (2013.01); *C07K 2317/21* (2013.01); *C07K 2317/24* (2013.01); *C07K 2317/31* (2013.01); *C07K 2317/34* (2013.01); *C07K 2317/565* (2013.01); *C07K 2317/92* (2013.01); *C12N 2760/16334* (2013.01)

(58) Field of Classification Search
None
See application file for complete search history.

(56) References Cited

U.S. PATENT DOCUMENTS

| | | |
|---|---|---|
| 5,670,626 A | 9/1997 | Chang et al. |
| 6,596,541 B2 | 7/2003 | Murphy et al. |
| 6,849,259 B2 | 2/2005 | Haurum et al. |
| 2003/0003133 A1 | 1/2003 | Schneider |
| 2004/0101920 A1 | 5/2004 | Radziejewski et al. |
| 2007/0231341 A1 | 10/2007 | McGavin et al. |
| 2007/0280945 A1 | 12/2007 | Stevens et al. |
| 2010/0143266 A1 | 6/2010 | Wells et al. |
| 2010/0239599 A1 | 9/2010 | Hafner et al. |
| 2015/0299303 A1 | 10/2015 | Orengo et al. |

FOREIGN PATENT DOCUMENTS

| | | |
|---|---|---|
| CN | 101802015 A | 8/2010 |
| EP | 2380591 A2 | 10/2016 |
| WO | 1993/013772 A1 | 7/1993 |
| WO | 2005/103081 A2 | 11/2005 |
| WO | 2006/097530 A2 | 9/2006 |
| WO | 2007/065633 A1 | 6/2007 |
| WO | 2007/140505 A2 | 12/2007 |
| WO | 2008/119353 A1 | 10/2008 |
| WO | 2008/145142 A1 | 12/2008 |

OTHER PUBLICATIONS

Al-Lazikani et al. (1997) "Standard Conformations for the Canonical Structures of Immunoglobulins", J. Mol. Biol. 273:927-948.
Altschul et al. (1990) "Basic Local Alignment Search Tool", J. Mol. Biol. 215: 403-410.
Altschul et al. (1997) "Gapped BLAST and PSI-BLAST: a new generation of protein database search programs", Nucleic Acids Res. 25:3389-3402.
Anderson et al. (1985) "A comparative study of the allergens of cat urine, serum, saliva, and pelt", J. Allergy Clin. Immunol. 76:563-569.
Bartholome et al. (1985) "Where does cat allergen 1 come from?", J. Allergy Clin. Immunol. 76:503-506.
Cady et al. (2010) "IgG antibodies produced during subcutaneous allergen immunotherapy mediate inhibition of basophil activation (Continued)

*Primary Examiner* — Nora Rooney
(74) *Attorney, Agent, or Firm* — FisherBroyles, LLP; Veronica Mallon; Cara L. Crowley-Weber

(57) ABSTRACT

The present invention provides antibodies that bind to the cat allergen, Fel d1, compositions comprising the antibodies, nucleic acids encoding the antibodies and methods of use of the antibodies. According to certain embodiments of the invention, the antibodies are fully human antibodies that bind to Fel d1. The antibodies of the invention are useful for binding to the Fel d1 allergen in vivo, thus preventing binding of the Fel d1 allergen to pre-formed IgE on the surface of mast cells or basophils. In doing so, the antibodies act to prevent the release of histamine and other inflammatory mediators from mast cells and/or basophils, thus ameliorating the untoward response to the cat allergen in sensitized individuals. The antibodies of the invention may also be useful for diagnostic purposes to determine if a patient is allergic to the Fel d1 cat allergen.

8 Claims, No Drawings

(56) References Cited

OTHER PUBLICATIONS via a mechanism involving both FcgammaRIIA and FcgammaRIIB", Immunol. Letters 130:57-65.
Carter (2006) "Potent Antibody Therapeutics by Design", J. of Immnol. 6:343-357.
Chapman et al. (1988) "Monoclonal Antibodies to the Major Feline Allergen Fel d 1", J. of Immnol. 140(3):812-818.
Charpin et al. (1991) "Fel d 1 allergen distribution in cat fur and skin", J. Allergy Clin. Immunol. 88:77-82.
Dabrowski et al. (1990) "Cat skin as an important source of Fel d 1 allergen", J. Allergy Clin. Immunol. 86:462-465.
Davies and Riechmann (1996) "Affinity improvement of single antibody VH domains: residues in all three hypervariable regions affect antigen binding", Immunotech. 2:169-179.
De Groot et al. (1988) "Monoclonal antibodies to the major feline allergen Fel d l", J. Allergy Clin. Immunol. 82 (5):778-786.
Duffort et al. (1991) "Studies on the biochemical structure of the major cat allergen Felis domesticus l", Mol. Immunol. 28:301-309.
Ehring (1999) "Hydrogen Exchange/Electrospray Ionization Mass Spectrometry Studies of Structural Features of Proteins and Protein/Protein Interactions", Analytical Biochemistry 267(2):252-259.
Engen and Smith (2001) "The Basics of Ion Chromatography", Anal. Chem. 73:256A-265A.
GenBank accession No. NP_001041619.1.
GenBank accession No. NP_001041618.1.
GenBank accession No. P30440.
GenBank accession No. P30438.
Gonnet et al. (1992) "Exhaustive Matching of the Entire Protein Sequence Database", Science 256: 1443-1445.
Griffith et al. (1992) "Expression and genomic structure of the genes encoding Fdl, the major allergen from the domestic cat", Gene 113:263-268.
Hedlin et al. (1991) "Immunotherapy with cat- and dog-dander extracts. V. Effects of 3 years of treatment", J. Allergy Clin. Immunol. 87:955-964.
Holt et al. (2003) "Domain antibodies: proteins for therapy", Trends in Biotech. 21(11):484-490.
Ichikawa et al. (2011) "Molecular cloning, expression and modelling of cat allergen, cystatin (Fel d 3), a cysteine protease inhibitor", Clin. Exp. Allergy, 31:1279-1286.
Junghans et al. (1990) "Anti-Tac-H, a Humanized Antibody to the Interleukin 2 Receptor with New Features for Immunotherapy in Malignant and Immune Disoders", Cancer Res. 50:1495-1502.
Kaiser et al. (2003) "The Crystal Structure of the Major Cat Allergen Fel d 1, a Member of the Secretoglobin Family", J. Biol. Chem. 278(39):37730-37735.
Kaiser et al. (2007) "Structural Characterization of the Tetrameric form of the Major Cat Allergen Fel d 1", J. Mol. Biol. 370:714-727.
Kazane et al. (2012) "Synthesis of Bispecific Antibodies using Genetically Encoded Unnatural Amino Acids", J. Am. Chem. Soc. [Epub: Dec. 4, 2012].
Klug et al. (2000) "Uteroglobin/Clara cell 10-kDa family of proteins: nomenclature committee report", Ann. N.Y. Acad. Sci. 923:348-354.
Klein et al. (2012) "Progress in overcoming the chain association issue in bispecific heterodimeric IgG antibodies", mAbs 4:6, 1-11.
Kristensen et al. (1997) "Determination of isoforms, N-linked glycan structure and disulfide bond linkages of the major cat allergen Fel dl by a mass spectrometric approach", Biol. Chem. 378:899-908.
Kufer et al. (2004) "A revival of bispecific antibodies," Trends Biotechnol. 22:238-244.
Lau et al. (2000) "Early exposure to house-dust mite and cat allergens and development of childhood asthma: a cohort study. Multicentre Allergy Study Group", Lancet 356:1392-1397.
Langer (1990) "New methods of drug delivery", Science 249:1527-1533.
Leitermann et al. (1984) "Cat allergen 1: Biochemical, antigenic, and allergenic properties", J. Allergy Clin. Immunol. 74:147-153.
Lija et al. (1989) "Immunotherapy with cat- and dog-dander extracts. IV. Effects of 2 years of treatment", J. Allergy Clin. Immunol. 83:37-44.
Lowenstein et al. (1985) "Identification and clinical significance of allergenic molecules of cat origin. Part of the DAS 76 Study", Allergy 40:430-441.
Mariuzza, R.A. et al. (1987) "The Structural Basis of Antigen-Atibody Recognition", Ann. Rev. Biophys. Biphys. Chem. 16:139-159.
Martin et al. (1989) "Modeling antibody hypervariable loops: A combined algorithm", Proc. Natl. Acad. Sci. USA 86:9268-9272.
Martinez-Gomez et al. (2009) "Targeting the MHC class II pathway of antigen presentation enhances immunogenicity and safety of allergen immunotherapy", Allergy 64:172-178.
Mata et al. (1992) "Fel d 1 allergen: skin and or saliva?", Ann. Allergy 69(4):321-322.
Morgenstern et al. (1991) "Amino acid sequence of Fel dl, the major allergen of the domestic cat: protein sequence analysis and cDNA cloning", PNAS 88:9690-9694.
Norman et al. (1996) "Treatment of cat allergy with T-cell reactive peptides", Am. J. Respir. Crit. Care Med. 154:1623-1628.
Ormstad et al. (2003) "The effect of endotoxin on the production of IgE, IgG1 and IgG2a antibodies against the cat allergen Fel d 1 in mice", Toxicology 188:309-318.
Oldfield et al. (2002) "Effect of T-cell peptides derived from Fel d 1 on allergic reactions and cytokine production in patients sensitive to cats: a randomised controlled trial", Lancet, 360:47-53.
Padlan et al. (1995) Indentification of specificity-determining residues in anitbodies, FASEB J. 9:133-139.
Pearson (1994) "Using the FASTA Program to Search Protein and DNA Sequence Databases", Methods Mol. Biol. 24: 307-331.
Platts-Mills et al. (1997) "Indoor allergens and asthma: report of the Third International Workshop", J. Allergy Clin. Immunol. 100:S2-S24.
Powell et al. (1998) "Compendium of excipients for parenteral formulations", PDA J Pharm Sci Technol 52:238-311.
Rader et al. (1998) "A phage display approach for rapid antibody humanization: Designed combinatorial V gene libraries", PNAS 95:8910-8915.
Reddy et al. (2000) "Elimination of Fc Receptor-Dependent Effector Functions of a Modified IgG4 Monoclonal Antibody to Human CD4", J. Immunol. 164:1925-1933.
Reineke (2004) "Antibody Epitope Mapping Using Arrays of Synthetic Peptides", Methods Mol Biol 248:443-463.
Rudikoff et al. (1982) "Single Amino Acid Substitution Altering Antigen-Binding Specificity", PNAS 79:1979-1983.
Saarne et al. (2011) "Treatment with a Fel d 1 hypoallergen reduces allergic responses in a mouse model for cat allergy", Allergy 66(2):255-263.
Senti et al. (2012) "Intralymphatic immunotherapy for cat allergy induces tolerance after only 3 injections", J. Allergy Clin. Immunol. 129(5):1290-1296.
Shields et al. (2002) "Lack of Fucose on Human IgG1 N-Linked Oligosaccharide Improves Binding to Human Fc RIII and Antibody-dependent Cellular Toxicity", The Journal of Bilogical Chemistry 277:26733-26740.
Tomer (2000) "Characterization of a discontinuous epitope of the human immunodeficiency virus (HIV) core protein p24 by epitope excision and differential chemical modification followed by mass spectrometric peptide mapping analysis", Protein Science 9:487-496.
Tutt et al. (1991) "Trispecific F(ab')3 Derivatives that use Cooperative Signaling via the TCR/CD3 Complex and CD2 to Activate and Redirect Resting Cytotoxic T Cells", J. Immunol. 147:60-69.
Uermosi et al. (2010) "Mechanisms of allergen-specific desensitization", J. Allergy Clin. Immunol. 126:375-383.
Vajdos et al. (2002) "Comprehensive Functional Maps of the Antigenbinding Site of an Anti-ErbB2 Antibody Obtained with Shotgun Scanning Mutagenesis", J Mol Biol 320:415-428.
Van Ree et al. (1999) "Purified natural and recombinant Fel d 1 and cat albumin in in vitro diagnostics for cat allergy", J. Allergy Clin. Immunol. 104(6): 1223-1230.

(56) References Cited

OTHER PUBLICATIONS

Van Milligen et al. (1992) "Presence of Felis domesticus allergen 1 in the cat's salivary and lacrimal glands", Int. Arch. Allergy Appl. Immunol. 92(4):375-378.
Van Milligen et al. (1993) "Calculation of the affinity constant KASS for solid phase antigen", Journal of Immunological Methods 162:165-173.
Wark et al. (2006) "Latest Technologies for the Enhancement of Antibody Affinity", Advanced Drug Delivery Reviews 58(5-6):657-670.
Wu et al. (1987) "Receptor-mediated in VitroGene Transformation by a Soluble DNA Carrier System", J. Biol. Chem. 262:4429-4432.
International Search Report with respect to PCT/US2013/039192 dated Sep. 19, 2013.
PCT Invitation to Pay Fees with respect to PCT/US2013/039192 dated Jul. 26, 2013.

SEQUENCE LISTING

<160> NUMBER OF SEQ ID NOS: 490

<210> SEQ ID NO 1
<211> LENGTH: 363
<212> TYPE: DNA
<213> ORGANISM: Artificial Sequence
<220> FEATURE:
<223> OTHER INFORMATION: Synthetic

<400> SEQUENCE: 1

```
gaggtgcagc tggtggagtc tgggggaggc ttggtccagc ctgggggtc cctgagactc      60 tcctgtacag cctctggatt cattttagt aacttttgga tgacttgggt ccgccaggct     120
ccagggaagg ggctggagtg ggtggccaac ataaagcaag atggaagtga gacatactgt     180
gtggactctg tgaagggccg attcaccatc tccagagacc acgccaagaa ctcactgttt     240
ctgcaaatga acagcctgag agccgaggac acggctgtat attactgtgc aagaggagct     300
ggaacaatct actactacgg tatggacgtc tggggccaag gaccacggt cattgtctcc      360 tca                                                                 363
```

<210> SEQ ID NO 2
<211> LENGTH: 121
<212> TYPE: PRT
<213> ORGANISM: Artificial Sequence
<220> FEATURE:
<223> OTHER INFORMATION: Synthetic

<400> SEQUENCE: 2

```
Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Ile Phe Ser Asn Phe
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Thr Tyr Cys Val Asp Ser Val
    50                  55                  60

Lys Gly Arg Phe Thr Ile Ser Arg Asp His Ala Lys Asn Ser Leu Phe
65                  70                  75                  80

Leu Gln Met Asn Ser Leu Arg Ala Glu Asp Thr Ala Val Tyr Tyr Cys
```

```
                     85                  90                  95
Ala Arg Gly Ala Gly Thr Ile Tyr Tyr Tyr Gly Met Asp Val Trp Gly
                100                 105                 110

Gln Gly Thr Thr Val Ile Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcattt ttagtaactt ttgg                                     24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Ile Phe Ser Asn Phe Trp
1               5
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
ataaagcaag atggaagtga gaca                                     24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

```
Ile Lys Gln Asp Gly Ser Glu Thr
1               5
```

<210> SEQ ID NO 7
<211> LENGTH: 42
<212> TYPE: DNA
<213> ORGANISM: Artificial Sequence
<220> FEATURE:
<223> OTHER INFORMATION: Synthetic

<400> SEQUENCE: 7
gcaagaggag ctggaacaat ctactactac ggtatggacg tc                 42

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Ala Arg Gly Ala Gly Thr Ile Tyr Tyr Tyr Gly Met Asp Val
1               5                   10

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9

```
gacatccaga tgacccagtc tccatcttcc gtgtctgcat ctgtaggaga cagactcacc    60
atcacttgtc gggcgagtca ggatattagc agctggttaa cctggtatca gcagaaacca   120
gggaaagccc ctaacctcct gatctatgct gcatccggtt tgcaaagtgg agtcccatca   180
aggttcagcg gcagtggatc tgggacagat ttcactctca ccatcagcaa cctgcagcct   240
gaagattttg caacttacta ttgtcaacag gctaacagtt tcccgctcac cttcggccaa   300
gggacacgac tggagattaa a                                             321
```

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Val Ser Ala Ser Val Gly
1               5                   10                  15

Asp Arg Leu Thr Ile Thr Cys Arg Ala Ser Gln Asp Ile Ser Ser Trp
            20                  25                  30

Leu Thr Trp Tyr Gln Gln Lys Pro Gly Lys Ala Pro Asn Leu Leu Ile
        35                  40                  45

Tyr Ala Ala Ser Gly Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gln Gly Thr Arg Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
caggatatta gcagctgg                                                  18
```

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Asp Ile Ser Ser Trp
  1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                                  9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
  1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacaggcta acagtttccc gctcacc                                             27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Ala Asn Ser Phe Pro Leu Thr
  1               5

<210> SEQ ID NO 17
<211> LENGTH: 357
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggaggc tggtcaagc ctgggggtc cctgagactc          60 tcctgtgcag cctctggatt caccttcaga aactataaca taaactgggt ccgccaggct       120
ccagggaagg ggctggagtg ggtctcactc atcagtggta gtagtagtta catatattac       180
gcagactcag tgaagggccg attcaccgtc tccagagaca cgccaagaa ctcactgtat        240 ctgcaaatga acagcctgag agccgaggac acggctgtgt attactgtgc gaggcggaca       300
ttaagctact acgttatgga cgtctggggc caagggacca cggtcaccgt ctcctca          357

<210> SEQ ID NO 18
<211> LENGTH: 119
<212> TYPE: PRT
```

<213> ORGANISM: Artificial Sequence
<220> FEATURE:
<223> OTHER INFORMATION: Synthetic

<400> SEQUENCE: 18

```
Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Arg Asn Tyr
            20                  25                  30
Asn Ile Asn Trp Val Arg Gln Ala Pro Gly Lys Gly Leu Glu Trp Val
        35                  40                  45
Ser Leu Ile Ser Gly Ser Ser Ser Tyr Ile Tyr Tyr Ala Asp Ser Val
    50                  55                  60
Lys Gly Arg Phe Thr Val Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Arg Thr Leu Ser Tyr Tyr Val Met Asp Val Trp Gly Gln Gly
            100                 105                 110
Thr Thr Val Thr Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagaaacta taac                                    24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly Phe Thr Phe Arg Asn Tyr Asn
 1               5
```

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
atcagtggta gtagtagtta cata                                    24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

```
Ile Ser Gly Ser Ser Ser Tyr Ile
 1               5
```

<210> SEQ ID NO 23
<211> LENGTH: 36
<212> TYPE: DNA
<213> ORGANISM: Artificial Sequence
<220> FEATURE:
<223> OTHER INFORMATION: Synthetic

<400> SEQUENCE: 23
gcgaggcgga cattaagcta ctacgttatg gacgtc         36

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Ala Arg Arg Thr Leu Ser Tyr Tyr Val Met Asp Val
 1               5                  10

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25
gacatccagg tgacccagtc tccatccccc ctgtctgcat ctgtaggaga cagagtcacc    60
atcacttgcc gggcgagtca gggcattagc aattatttag cctggtatca gcagaaacca   120
gggagagttc ctcagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataacagtg ccccgtacac ttttggccag   300
gggaccaagc tggagatcaa a                                             321

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Gln Val Thr Gln Ser Pro Ser Pro Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Arg Val Pro Gln Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105

```
<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagggcatta gcaattat                                                 18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Gly Ile Ser Asn Tyr
 1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc                                                            9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
 1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caaaagtata acagtgcccc gtacact                                       27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Lys Tyr Asn Ser Ala Pro Tyr Thr
 1               5

<210> SEQ ID NO 33
<211> LENGTH: 363
<212> TYPE: DNA
```

<213> ORGANISM: Artificial Sequence
<220> FEATURE:
<223> OTHER INFORMATION: Synthetic

<400> SEQUENCE: 33

| | | |
|---|---|---|
| caggtacagc tgcagcagtc aggtccagga ctggtgaagt cctcgcagac cctctcactc | 60 |
| acctgtgcca tctccgggga cagtgtctct agcaacagtg ttgcttggaa ttggatcagg | 120 |
| cagtccccat cgagaggcct tgagtggctg gggaggacat actacaggtc caaatggtat | 180 |
| aatgattatg cagtatctgt gaaaagtcga ataaacatca acccagacac atccaagaac | 240 |
| cacttctccc tgcagttgaa ttctgtgact cccgaggaca cggctgttta tttctgtgca | 300 |
| agagcctgga actggtacta ccttgactac tggggccagg gcaccctggt caccgtctcg | 360 |
| tca | 363 |

<210> SEQ ID NO 34
<211> LENGTH: 121
<212> TYPE: PRT
<213> ORGANISM: Artificial Sequence
<220> FEATURE:
<223> OTHER INFORMATION: Synthetic

<400> SEQUENCE: 34

Gln Val Gln Leu Gln Gln Ser Gly Pro Gly Leu Val Lys Ser Ser Gln
1               5                   10                  15

Thr Leu Ser Leu Thr Cys Ala Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Asn Ile Asn Pro Asp Thr Ser Lys Asn
65                  70                  75                  80

His Phe Ser Leu Gln Leu Asn Ser Val Thr Pro Glu Asp Thr Ala Val
                85                  90                  95

Tyr Phe Cys Ala Arg Ala Trp Asn Trp Tyr Tyr Leu Asp Tyr Trp Gly
            100                 105                 110

Gln Gly Thr Leu Val Thr Val Ser Ser
        115                 120

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35

| | |
|---|---|
| ggggacagtg tctctagcaa cagtgttgct | 30 |

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

Gly Asp Ser Val Ser Ser Asn Ser Val Ala
1               5                   10

<210> SEQ ID NO 37
<211> LENGTH: 27
<212> TYPE: DNA
<213> ORGANISM: Artificial Sequence
<220> FEATURE:
<223> OTHER INFORMATION: Synthetic

<400> SEQUENCE: 37
acatactaca ggtccaaatg gtataat                                              27

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Thr Tyr Tyr Arg Ser Lys Trp Tyr Asn
 1               5

<210> SEQ ID NO 39
<211> LENGTH: 33
<212> TYPE: DNA
<213> ORGANISM: Artificial Sequence
<220> FEATURE:
<223> OTHER INFORMATION: Synthetic

<400> SEQUENCE: 39
gcaagagcct ggaactggta ctaccttgac tac                                       33

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Ala Arg Ala Trp Asn Trp Tyr Tyr Leu Asp Tyr
 1               5                  10

<210> SEQ ID NO 41
<211> LENGTH: 339
<212> TYPE: DNA
<213> ORGANISM: Artificial Sequence
<220> FEATURE:
<223> OTHER INFORMATION: Synthetic

<400> SEQUENCE: 41
gatattgtga tgacccagtc tccagactcc ctggctatgt ctctaggcga gagggccacc          60
atcaactgca agtccagcca gagtgtttta tacagctcca acaataagaa ttacttaggt         120
tggtaccagc agaaaccagg acagcctcct aaactgctca tttactgggc atctacccgg         180
gaatccggtg tccctgaccg aatcagtggc agcgggtctg ggacagattt cactctcacc         240
atcagcagcc tgcaggctga agatgtggca gtttattact gtcagcaata tcttagaaat         300
acgctcactt tcggcggagg gaccaaggtg gagatcaaa                                 339

<210> SEQ ID NO 42
<211> LENGTH: 113
<212> TYPE: PRT
<213> ORGANISM: Artificial Sequence
<220> FEATURE:
<223> OTHER INFORMATION: Synthetic

<400> SEQUENCE: 42

Asp Ile Val Met Thr Gln Ser Pro Asp Ser Leu Ala Met Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Gly Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Ile Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Leu Arg Asn Thr Leu Thr Phe Gly Gly Gly Thr Lys Val Glu Ile
            100                 105                 110

Lys

<210> SEQ ID NO 43
<211> LENGTH: 36
<212> TYPE: DNA
<213> ORGANISM: Artificial Sequence
<220> FEATURE:
<223> OTHER INFORMATION: Synthetic

<400> SEQUENCE: 43
cagagtgttt tatacagctc caacaataag aattac                                36

<210> SEQ ID NO 44
<211> LENGTH: 12
<212> TYPE: PRT
<213> ORGANISM: Artificial Sequence
<220> FEATURE:
<223> OTHER INFORMATION: Synthetic

<400> SEQUENCE: 44

Gln Ser Val Leu Tyr Ser Ser Asn Asn Lys Asn Tyr
1               5                   10

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 tgggcatct                                                              9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Trp Ala Ser
1

<210> SEQ ID NO 47
<211> LENGTH: 27

```
<212> TYPE: DNA
<213> ORGANISM: Artificial Sequence
<220> FEATURE:
<223> OTHER INFORMATION: Synthetic

<400> SEQUENCE: 47
cagcaatatc ttagaaatac gctcact                                              27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Tyr Leu Arg Asn Thr Leu Thr
 1               5

<210> SEQ ID NO 49
<211> LENGTH: 381
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggaggc ctggtcaagc ctggggggtc cctgagactc          60
tcctgtgcag cctctggatt caccttcagt agctatagca tgaactgggt ccgccaggct         120
ccagggaagg ggctggagtg ggtctcatcc attagtagta gaagtagtta catatactac         180
gcagactcag tgaagggccg attcaccatc tcaagagaca acgccaagaa ctcactgtat         240
ctgcaaatga acagcctgag agccgaggac acggctgtgt attattgtgc gagagatcat         300
attgtagtag taccaggtgc tcctactac tactacggta tggacgtctg gggccaaggg          360
accacggtca ccgtctcctc a                                                   381

<210> SEQ ID NO 50
<211> LENGTH: 127
<212> TYPE: PRT
<213> ORGANISM: Artificial Sequence
<220> FEATURE:
<223> OTHER INFORMATION: Synthetic

<400> SEQUENCE: 50

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Ser Ile Ser Ser Arg Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp His Ile Val Val Val Pro Gly Ala Pro Tyr Tyr Tyr Tyr
            100                 105                 110

Gly Met Asp Val Trp Gly Gln Gly Thr Thr Val Thr Val Ser Ser
        115                 120                 125
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct tcagtagcta tagc                                          24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Ser
 1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagtagta gaagtagtta cata                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Arg Ser Ser Tyr Ile
 1               5

<210> SEQ ID NO 55
<211> LENGTH: 60
<212> TYPE: DNA
<213> ORGANISM: Artificial Sequence
<220> FEATURE:
<223> OTHER INFORMATION: Synthetic

<400> SEQUENCE: 55
gcgagagatc atattgtagt agtaccaggt gcctcctact actactacgg tatggacgtc    60

<210> SEQ ID NO 56
<211> LENGTH: 20
<212> TYPE: PRT
<213> ORGANISM: Artificial Sequence
<220> FEATURE:
<223> OTHER INFORMATION: Synthetic

<400> SEQUENCE: 56

Ala Arg Asp His Ile Val Val Val Pro Gly Ala Ser Tyr Tyr Tyr Tyr
 1               5                  10                  15
Gly Met Asp Val
            20

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctctgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgctcac tttcggcgga   300
gggaccaagg tggagatcaa a                                             321
```

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Ser Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Leu
                85                  90                  95
Thr Phe Gly Gly Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59

```
cagggcatta gaaatgat                                                  18
```

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Arg Asn Asp
1               5

```
<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc                                                                  9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
ctacagcata atagttaccc gctcact                                              27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Leu Gln His Asn Ser Tyr Pro Leu Thr
 1               5

<210> SEQ ID NO 65
<211> LENGTH: 369
<212> TYPE: DNA
<213> ORGANISM: Artificial Sequence
<220> FEATURE:
<223> OTHER INFORMATION: Synthetic

<400> SEQUENCE: 65
caggtgcagc tggtgcagtc tggggctgag gtgaagaagc ctggggcctc agtggaggtc          60
tcctgcaagg cttctggata caccttcacc gactactata tacactggat acgacaggcc        120
cctggacaag ggcttgagtg gatgggatgg atcaaccctg acagtggtcg cacaaactat        180
gcacagaagt ttcaggtcag ggtcaccatg accaggaca cgtccatcac cacagcctac         240
atggaactga acagactgaa atctgacgac acggccgtgt attactgtgc gagaggaccc        300
ctacgtggat atagcggcta cgattttttt gactactggg gccagggaac cctggtcacc        360
gtctcctca                                                                369

<210> SEQ ID NO 66
<211> LENGTH: 123
<212> TYPE: PRT
<213> ORGANISM: Artificial Sequence
<220> FEATURE:
```

<223> OTHER INFORMATION: Synthetic

<400> SEQUENCE: 66

Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Asp Tyr
            20                  25                  30

Tyr Ile His Trp Ile Arg Gln Ala Pro Gly Gln Gly Leu Glu Trp Met
        35                  40                  45

Gly Trp Ile Asn Pro Asp Ser Gly Arg Thr Asn Tyr Ala Gln Lys Phe
    50                  55                  60

Gln Val Arg Val Thr Met Thr Arg Asp Thr Ser Ile Thr Thr Ala Tyr
65                  70                  75                  80

Met Glu Leu Asn Arg Leu Lys Ser Asp Asp Thr Ala Val Tyr Tyr Cys
                85                  90                  95

Ala Arg Gly Pro Leu Arg Gly Tyr Ser Gly Tyr Asp Phe Phe Asp Tyr
            100                 105                 110

Trp Gly Gln Gly Thr Leu Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggatacacct tcaccgacta ctat                                          24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Tyr Thr Phe Thr Asp Tyr Tyr
1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
atcaaccctg acagtggtcg caca                                          24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Asn Pro Asp Ser Gly Arg Thr
1               5

<210> SEQ ID NO 71
<211> LENGTH: 48
<212> TYPE: DNA
<213> ORGANISM: Artificial Sequence
<220> FEATURE:
<223> OTHER INFORMATION: Synthetic

<400> SEQUENCE: 71
gcgagaggac ccctacgtgg atatagcggc tacgattttt ttgactac        48

<210> SEQ ID NO 72
<211> LENGTH: 16
<212> TYPE: PRT
<213> ORGANISM: Artificial Sequence
<220> FEATURE:
<223> OTHER INFORMATION: Synthetic

<400> SEQUENCE: 72

Ala Arg Gly Pro Leu Arg Gly Tyr Ser Gly Tyr Asp Phe Phe Asp Tyr
 1               5                  10                  15

<210> SEQ ID NO 73
<211> LENGTH: 339
<212> TYPE: DNA
<213> ORGANISM: Artificial Sequence
<220> FEATURE:
<223> OTHER INFORMATION: Synthetic

<400> SEQUENCE: 73
gacatcgtga tgacccagtc tccagactcc ctggctatat ctctgggcga gagggccacc      60
atcaactgca gtccagcca gagtgtttta tacagctcca acaataagca gtacttagct      120
tggtacaagc agagaccagg acagcctcct aagctgctca tttcctggac atctacccgg     180
gaatccgggg tccctgaccg attcagtggc agcgggtctg ggacagattt cactctcacc     240
atcagcagcc tgcaggctga agatgtggca gtttatttct gtcaacaata ttatagtact     300
ccgtacactt ttggccaggg gaccaagctg gagatcaga                            339

<210> SEQ ID NO 74
<211> LENGTH: 113
<212> TYPE: PRT
<213> ORGANISM: Artificial Sequence
<220> FEATURE:
<223> OTHER INFORMATION: Synthetic

<400> SEQUENCE: 74

Asp Ile Val Met Thr Gln Ser Pro Asp Ser Leu Ala Ile Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Gln Tyr Leu Ala Trp Tyr Lys Gln Arg Pro Gly Gln
        35                  40                  45

Pro Pro Lys Leu Leu Ile Ser Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ser Thr Pro Tyr Thr Phe Gly Gln Gly Thr Lys Leu Glu Ile
            100                 105                 110

Arg

<210> SEQ ID NO 75
<211> LENGTH: 36
<212> TYPE: DNA
<213> ORGANISM: Artificial Sequence
<220> FEATURE:
<223> OTHER INFORMATION: Synthetic

<400> SEQUENCE: 75
cagagtgttt tatacagctc caacaataag cagtac       36

<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Gln Ser Val Leu Tyr Ser Ser Asn Asn Lys Gln Tyr
 1               5                  10

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 tggacatct       9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Trp Thr Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacaatatt atagtactcc gtacact       27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Tyr Tyr Ser Thr Pro Tyr Thr
 1               5

<210> SEQ ID NO 81
<211> LENGTH: 369
<212> TYPE: DNA

<213> ORGANISM: Artificial Sequence
<220> FEATURE:
<223> OTHER INFORMATION: Synthetic

<400> SEQUENCE: 81

```
caggtggtac tggtggagtc tggggaggc gtggtccagc ctgggaggtc cctgagactc      60
tcctgtgcag cgtctggatt caccttcagt agctatggca tgcactgggt ccgccaggct     120
ccaggcaagg gctggagtg gtggcagtt atatggtatg atggaagtaa taaatactat      180
gtagactccg tgaagggccg attcaccatc tccagagaca attccaataa cacaatctat    240
ctgcaaatga acagcctgag agccgaggac acggctgtat attactgtgc gagatcccct    300
ataccagtgg ctggtacgga ccccattttt ggatactggg gccagggaac cctggtcacc    360
gtctcctca                                                             369
```

<210> SEQ ID NO 82
<211> LENGTH: 123
<212> TYPE: PRT
<213> ORGANISM: Artificial Sequence
<220> FEATURE:
<223> OTHER INFORMATION: Synthetic

<400> SEQUENCE: 82

```
Gln Val Val Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Val Asp Ser Val
         50                  55                  60

Lys Gly Arg Phe Thr Ile Ser Arg Asp Asn Ser Asn Asn Thr Ile Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ile Pro Val Ala Gly Thr Asp Pro Ile Phe Gly Tyr
                100                 105                 110

Trp Gly Gln Gly Thr Leu Val Thr Val Ser Ser
            115                 120
```

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83

```
ggattcacct tcagtagcta tggc                                            24
```

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

```
Gly Phe Thr Phe Ser Ser Tyr Gly
  1               5
```

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
atatggtatg atggaagtaa taaa                                           24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Trp Tyr Asp Gly Ser Asn Lys
 1               5

<210> SEQ ID NO 87
<211> LENGTH: 48
<212> TYPE: DNA
<213> ORGANISM: Artificial Sequence
<220> FEATURE:
<223> OTHER INFORMATION: Synthetic

<400> SEQUENCE: 87
gcgagatccc ttataccagt ggctggtacg gacccccattt ttggatac                48

<210> SEQ ID NO 88
<211> LENGTH: 16
<212> TYPE: PRT
<213> ORGANISM: Artificial Sequence
<220> FEATURE:
<223> OTHER INFORMATION: Synthetic

<400> SEQUENCE: 88

Ala Arg Ser Leu Ile Pro Val Ala Gly Thr Asp Pro Ile Phe Gly Tyr
 1               5                  10                  15

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccttccacc ctgtctgcat ctgtaggaga cagagtcacc    60
atcacttgcc gggccagtca gagtgttagt agctggttgg cctggtatca gcagaaacca   120
gggaaagccc ctaaactcct gatctttaag gcgtctggtt tagaaagtgg ggtcccattt   180
aggttcagcg gcagtggatc tgggacagaa ttcactctca ccatcagcag cctgcagcct   240
gatgattttg caacttatta ctgccaacag tataatactt attctccgac gttcggccaa   300
gggaccaagg tggagatcaa a                                              321

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Ser Trp
            20                  25                  30

Leu Ala Trp Tyr Gln Gln Lys Pro Gly Lys Ala Pro Lys Leu Leu Ile
        35                  40                  45

Phe Lys Ala Ser Gly Leu Glu Ser Gly Val Pro Phe Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Ser Pro
                85                  90                  95

Thr Phe Gly Gln Gly Thr Lys Val Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagtgtta gtagctgg                                                 18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Val Ser Ser Trp
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 aaggcgtct                                                            9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Lys Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacagtata atacttattc tccgacg                                                27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Tyr Asn Thr Tyr Ser Pro Thr
1               5

<210> SEQ ID NO 97
<211> LENGTH: 360
<212> TYPE: DNA
<213> ORGANISM: Artificial Sequence
<220> FEATURE:
<223> OTHER INFORMATION: Synthetic

<400> SEQUENCE: 97
caggtgcagc tgcaggagtc gggcccagga ctggtgaagc cttcggagac cctgtccctc      60
acctgcactg tctctggtgg ctccatcagt aattactact ggagctggat ccggcagccc     120
ccagggaagg gactggagtg gattggatat atctattata gtgggagaac caactacaac     180
ccctccctca gagtcgagt caccatatca gtggacacgt ccaagaacca gttctccctg     240
aagctgaggt ctgtgaccgc cgcagacacg gccgtgtatt actgtgcgag acatcgtata     300
actagaactg cggactcctt tgactactgg ggccaggaa ccctggtcac cgtctcctca     360

<210> SEQ ID NO 98
<211> LENGTH: 120
<212> TYPE: PRT
<213> ORGANISM: Artificial Sequence
<220> FEATURE:
<223> OTHER INFORMATION: Synthetic

<400> SEQUENCE: 98

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Arg Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg His Arg Ile Thr Arg Thr Ala Asp Ser Phe Asp Tyr Trp Gly Gln
            100                 105                 110

Gly Thr Leu Val Thr Val Ser Ser
        115                 120

<210> SEQ ID NO 99
<211> LENGTH: 24

<212> TYPE: DNA
<213> ORGANISM: Artificial Sequence
<220> FEATURE:
<223> OTHER INFORMATION: Synthetic

<400> SEQUENCE: 99
ggtggctcca tcagtaatta ctac                                          24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Gly Ser Ile Ser Asn Tyr Tyr
 1               5

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
atctattata gtgggagaac c                                             21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Tyr Tyr Ser Gly Arg Thr
 1               5

<210> SEQ ID NO 103
<211> LENGTH: 42
<212> TYPE: DNA
<213> ORGANISM: Artificial Sequence
<220> FEATURE:
<223> OTHER INFORMATION: Synthetic

<400> SEQUENCE: 103
gcgagacatc gtataactag aactgcggac tcctttgact ac                      42

<210> SEQ ID NO 104
<211> LENGTH: 14
<212> TYPE: PRT
<213> ORGANISM: Artificial Sequence
<220> FEATURE:
<223> OTHER INFORMATION: Synthetic

<400> SEQUENCE: 104

Ala Arg His Arg Ile Thr Arg Thr Ala Asp Ser Phe Asp Tyr
 1               5                  10

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105

```
gacatccaga tgacccagtc tccatcctcc ctgtctgcat ctgtaggaga cagagtcacc    60
atcacttgcc aggcgagtca ggacattacc aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatgttg caacatttta ctgtcaccag tatggtgatc tcccgtacac ttttggccag   300
gggaccaagc tggagatcaa a                                             321
```

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Phe Tyr Cys His Gln Tyr Gly Asp Leu Pro Tyr
                85                  90                  95

Thr Phe Gly Gln Gly Thr Lys Leu Glu Ile Lys
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107

```
caggacatta ccaactat                                                  18
```

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

```
Gln Asp Ile Thr Asn Tyr
1               5
```

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gatgcatcc                                                                        9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Asp Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caccagtatg gtgatctccc gtacact                                                   27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

His Gln Tyr Gly Asp Leu Pro Tyr Thr
 1               5

<210> SEQ ID NO 113
<211> LENGTH: 369
<212> TYPE: DNA
<213> ORGANISM: Artificial Sequence
<220> FEATURE:
<223> OTHER INFORMATION: Synthetic

<400> SEQUENCE: 113
caggtggtat tggtggagtc tgggggaggc gtggtccagc ctgggaggtc cctgagactc        60
tcctgtgcag cgtctggatt caccttcagt agctatggca tgcactgggt ccgccaggct       120
ccaggcaagg ggctggagtg ggtggcagtt atttggtatg atggaagtat taaatactat       180
gcagactccg tgaagggccg attcaccatc tccagagaca attccaataa cacaatctat       240
ctgcaaatga acagcctgag agccgaggac acggctgtat attactgtgc gagagccctt       300
ataccagtgg ctggtacgga ccccattttt gggtactggg gccagggaac cctggtcacc       360
gtctcctca                                                              369

<210> SEQ ID NO 114
<211> LENGTH: 123
<212> TYPE: PRT
<213> ORGANISM: Artificial Sequence
<220> FEATURE:
<223> OTHER INFORMATION: Synthetic

<400> SEQUENCE: 114

Gln Val Val Leu Val Glu Ser Gly Gly Gly Val Val Gln Pro Gly Arg
 1               5                   10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Lys Tyr Tyr Ala Asp Ser Val
 50                  55                  60

Lys Gly Arg Phe Thr Ile Ser Arg Asp Asn Ser Asn Asn Thr Ile Tyr
 65                  70                  75                  80

Leu Gln Met Asn Ser Leu Arg Ala Glu Asp Thr Ala Val Tyr Tyr Cys
                85                  90                  95

Ala Arg Ala Leu Ile Pro Val Ala Gly Thr Asp Pro Ile Phe Gly Tyr
            100                 105                 110

Trp Gly Gln Gly Thr Leu Val Thr Val Ser Ser
        115                 120
```

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct tcagtagcta tggc                                        24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

```
Gly Phe Thr Phe Ser Ser Tyr Gly
 1               5
```

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
atttggtatg atggaagtat taaa                                        24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

```
Ile Trp Tyr Asp Gly Ser Ile Lys
 1               5
```

<210> SEQ ID NO 119
<211> LENGTH: 48
<212> TYPE: DNA
<213> ORGANISM: Artificial Sequence
<220> FEATURE:
<223> OTHER INFORMATION: Synthetic

<400> SEQUENCE: 119
gcgagagccc ttataccagt ggctggtacg gacccccattt ttgggtac        48

<210> SEQ ID NO 120
<211> LENGTH: 16
<212> TYPE: PRT
<213> ORGANISM: Artificial Sequence
<220> FEATURE:
<223> OTHER INFORMATION: Synthetic

<400> SEQUENCE: 120

Ala Arg Ala Leu Ile Pro Val Ala Gly Thr Asp Pro Ile Phe Gly Tyr
1               5                   10                  15

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121
gacatccaga tgacccagtc tccttccacc ctgtctgcat ctgtaggaga cagagtcacc     60
atcacttgcc gggccagtca gagtgttagt agctggttgg cctggtatca gcagaaacca    120
gggaaagccc ctaaactcct gatctttaag acgtctggtt tagaaagtgg ggtcccattt    180
aggttcagcg gcagtggatc tgggacagaa ttcactctca ccatcagcag cctgcagcct    240
gatgattttg caacttatta ctgccaacag tataatactt attctccgac gttcggccaa    300
gggaccaagg tggagatcaa a                                              321

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Ser Trp
            20                  25                  30

Leu Ala Trp Tyr Gln Gln Lys Pro Gly Lys Ala Pro Lys Leu Leu Ile
        35                  40                  45

Phe Lys Thr Ser Gly Leu Glu Ser Gly Val Pro Phe Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Ser Pro
                85                  90                  95

Thr Phe Gly Gln Gly Thr Lys Val Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagagtgtta gtagctgg                                                    18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Ser Val Ser Ser Trp
 1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 aagacgtct                                                               9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Lys Thr Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
caacagtata atacttattc tccgacg                                          27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Asn Thr Tyr Ser Pro Thr
 1               5

<210> SEQ ID NO 129
<211> LENGTH: 360
<212> TYPE: DNA
<213> ORGANISM: Artificial Sequence
<220> FEATURE:
<223> OTHER INFORMATION: Synthetic

<400> SEQUENCE: 129
caggtgcagc tgcaggagtc gggcccagga ctggtgaagc cttcggagac cctgtccctc      60
acctgcactg tctctggtgg ctccatcagt agttactact ggagctggat ccggcagccc     120

```
ccagggaagg gactggagtg gattggatat atctattaca gtgggagaac caactacaac    180
ccctccctca agagtcgagt caccatatca gtggacacgt ccaagaacca gttctccctg    240
aaactgagct ctgtgaccgc cgcagacacg gccatttatt actgtgcgag acatcgtgta    300
actagaactg cggactcctt tgactactgg ggccaggaa ccctggtcac cgtctcctca    360
```

<210> SEQ ID NO 130
<211> LENGTH: 120
<212> TYPE: PRT
<213> ORGANISM: Artificial Sequence
<220> FEATURE:
<223> OTHER INFORMATION: Synthetic

<400> SEQUENCE: 130

```
Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Arg Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Ile Tyr Tyr Cys Ala
                85                  90                  95

Arg His Arg Val Thr Arg Thr Ala Asp Ser Phe Asp Tyr Trp Gly Gln
            100                 105                 110

Gly Thr Leu Val Thr Val Ser Ser
        115                 120
```

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131

```
ggtggctcca tcagtagtta ctac                                            24
```

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

```
Gly Gly Ser Ile Ser Ser Tyr Tyr
 1               5
```

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133

```
atctattaca gtgggagaac c                                               21
```

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Tyr Tyr Ser Gly Arg Thr
 1               5

<210> SEQ ID NO 135
<211> LENGTH: 42
<212> TYPE: DNA
<213> ORGANISM: Artificial Sequence
<220> FEATURE:
<223> OTHER INFORMATION: Synthetic

<400> SEQUENCE: 135
gcgagacatc gtgtaactag aactgcggac tcctttgact ac                        42

<210> SEQ ID NO 136
<211> LENGTH: 14
<212> TYPE: PRT
<213> ORGANISM: Artificial Sequence
<220> FEATURE:
<223> OTHER INFORMATION: Synthetic

<400> SEQUENCE: 136

Ala Arg His Arg Val Thr Arg Thr Ala Asp Ser Phe Asp Tyr
 1               5                  10

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcctcc ctgtctgcat ctgtaggaga cagagtcacc      60
atcacttgcc aggcgagtca ggacattaac aactatttaa attggtatca gcagaaaaca     120
gggaaagccc ctaagttcct gatctacgat gcatccaatt tggaaacagg ggtctcatca     180
aggttcagtg aagtggatc tgggacagat tttactttca ccatcagcag cctgcagcct     240
gaagatgttg aacatatta ctgtcaccag tatggtgatc tcccgtacac ttttggccag     300
gggaccaagc tggagatcaa a                                               321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Asn Tyr
             20                  25                  30

Leu Asn Trp Tyr Gln Gln Lys Thr Gly Lys Ala Pro Lys Phe Leu Ile
         35                  40                  45

```
Tyr Asp Ala Ser Asn Leu Glu Thr Gly Val Ser Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Val Gly Thr Tyr Tyr Cys His Gln Tyr Gly Asp Leu Pro Tyr
                 85                  90                  95

Thr Phe Gly Gln Gly Thr Lys Leu Glu Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
caggacatta acaactat                                              18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

```
Gln Asp Ile Asn Asn Tyr
 1               5
```

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gatgcatcc                                                         9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

```
Asp Ala Ser
 1
```

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caccagtatg gtgatctccc gtacact                                    27

<210> SEQ ID NO 144
<211> LENGTH: 9
<212> TYPE: PRT

```
<213> ORGANISM: Artificial Sequence
<220> FEATURE:
<223> OTHER INFORMATION: Synthetic

<400> SEQUENCE: 144

His Gln Tyr Gly Asp Leu Pro Tyr Thr
 1               5

<210> SEQ ID NO 145
<211> LENGTH: 360
<212> TYPE: DNA
<213> ORGANISM: Artificial Sequence
<220> FEATURE:
<223> OTHER INFORMATION: Synthetic

<400> SEQUENCE: 145
gaggtgcagc tggtggagtc tgggggaggc ctggtcaggc cgggggatc cctgagactc      60 tcctgtgcag cctctggatt caccttcact agctatgcca tgaattgggt ccgccaggct    120
ccagggaagg gactggagtg gtctcatcc atttctagtt atagttctta catatatatc     180
gcagactcag tgaagggccg attcaccctc tccagagaca atgccaagaa ctcactgtat    240
ctacaaatgc acagtctgag acccgaggac acggctgttt atttctgtgc gagagaggga    300
tatagtgcct actcctactt tgacttctgg ggccggggaa ccctggtcac cgtctcctca    360

<210> SEQ ID NO 146
<211> LENGTH: 120
<212> TYPE: PRT
<213> ORGANISM: Artificial Sequence
<220> FEATURE:
<223> OTHER INFORMATION: Synthetic

<400> SEQUENCE: 146

Glu Val Gln Leu Val Glu Ser Gly Gly Gly Leu Val Arg Pro Gly Gly
 1               5                  10                  15

Ser Leu Arg Leu Ser Cys Ala Ala Ser Gly Phe Thr Phe Thr Ser Tyr
             20                  25                  30

Ala Met Asn Trp Val Arg Gln Ala Pro Gly Lys Gly Leu Glu Trp Val
         35                  40                  45

Ser Ser Ile Ser Ser Tyr Ser Ser Tyr Ile Tyr Ile Ala Asp Ser Val
     50                  55                  60

Lys Gly Arg Phe Thr Leu Ser Arg Asp Asn Ala Lys Asn Ser Leu Tyr
 65                  70                  75                  80

Leu Gln Met His Ser Leu Arg Pro Glu Asp Thr Ala Val Tyr Phe Cys
                 85                  90                  95

Ala Arg Glu Gly Tyr Ser Ala Tyr Ser Tyr Phe Asp Phe Trp Gly Arg
            100                 105                 110

Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct tcactagcta tgcc                                            24

<210> SEQ ID NO 148
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Thr Ser Tyr Ala
1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atttctagtt atagttctta cata                                              24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Ser Tyr Ser Ser Tyr Ile
1               5

<210> SEQ ID NO 151
<211> LENGTH: 39
<212> TYPE: DNA
<213> ORGANISM: Artificial Sequence
<220> FEATURE:
<223> OTHER INFORMATION: Synthetic

<400> SEQUENCE: 151
gcgagagagg gatatagtgc ctactcctac tttgacttc                              39

<210> SEQ ID NO 152
<211> LENGTH: 13
<212> TYPE: PRT
<213> ORGANISM: Artificial Sequence
<220> FEATURE:
<223> OTHER INFORMATION: Synthetic

<400> SEQUENCE: 152

Ala Arg Glu Gly Tyr Ser Ala Tyr Ser Tyr Phe Asp Phe
1               5                   10

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccttccacc ctgtctgcat ctgttggaga cagagtcacc        60
atcacttgcc gggccagtca gagtgttatt agttggttgg cctggtatca acagaaacca       120
gggaaagccc ctaaactcct gatccatagg cgtctagtt tagaaagtgg ggtcccatca        180
aggttcagcg gcagtggatc tgggacagaa ttcactctca ccatcagcgg cctgcagcct       240
```
gatgattttg caacttatta ctgtcaacag tataatactt attttccgac gttcggccaa      300
gggaccaagg tggaagtcaa a                                                321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ile Ser Trp
            20                  25                  30

Leu Ala Trp Tyr Gln Gln Lys Pro Gly Lys Ala Pro Lys Leu Leu Ile
        35                  40                  45

His Arg Ala Ser Ser Leu Glu Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Asp Asp Phe Ala Thr Tyr Tyr Cys Gln Gln Tyr Asn Thr Tyr Phe Pro
                85                  90                  95

Thr Phe Gly Gln Gly Thr Lys Val Glu Val Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagagtgtta ttagttgg                                                    18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Ser Val Ile Ser Trp
1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 agggcgtct                                                              9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Arg Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caacagtata atacttattt tccgacg                                          27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Tyr Asn Thr Tyr Phe Pro Thr
 1               5

<210> SEQ ID NO 161
<211> LENGTH: 354
<212> TYPE: DNA
<213> ORGANISM: Artificial Sequence
<220> FEATURE:
<223> OTHER INFORMATION: Synthetic

<400> SEQUENCE: 161
gaggtggaac tgttggaatc tggggggaggc ttggtacagc ctgggggggtc cctgagactc     60 tcctgtgcag cctctggatt caccttttagt agttatgcca tgagttgggt ccgccaggct    120
ccagggaagg ggctggagtg ggtctcatct attagtggta gggttggtag cacacatttc    180
gcagactccg tgaagggccg gttcaccttc tccagagaca attccaagaa cacgctgtat    240
ctgcagctga gcagcctgag agccgaggac acggccgtat attactgtgc gagaagtaga    300
ggagcagcct actttgacta ctggggccag ggaaccctgg tcaccgtctc ctca          354

<210> SEQ ID NO 162
<211> LENGTH: 118
<212> TYPE: PRT
<213> ORGANISM: Artificial Sequence
<220> FEATURE:
<223> OTHER INFORMATION: Synthetic

<400> SEQUENCE: 162

Glu Val Glu Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Arg Val Gly Ser Thr His Phe Ala Asp Ser Val
    50                  55                  60

Lys Gly Arg Phe Thr Phe Ser Arg Asp Asn Ser Lys Asn Thr Leu Tyr
65                  70                  75                  80

Leu Gln Leu Ser Ser Leu Arg Ala Glu Asp Thr Ala Val Tyr Tyr Cys 85                  90                  95
Ala Arg Ser Arg Gly Ala Ala Tyr Phe Asp Tyr Trp Gly Gln Gly Thr
            100                 105                 110

Leu Val Thr Val Ser Ser
        115

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcacct ttagtagtta tgcc                                          24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Ser Ser Tyr Ala
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attagtggta gggttggtag caca                                          24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Ser Gly Arg Val Gly Ser Thr
1               5

<210> SEQ ID NO 167
<211> LENGTH: 33
<212> TYPE: DNA
<213> ORGANISM: Artificial Sequence
<220> FEATURE:
<223> OTHER INFORMATION: Synthetic

<400> SEQUENCE: 167
gcgagaagta gaggagcagc ctactttgac tac                                33

<210> SEQ ID NO 168
<211> LENGTH: 11
<212> TYPE: PRT
<213> ORGANISM: Artificial Sequence
<220> FEATURE:
<223> OTHER INFORMATION: Synthetic

<400> SEQUENCE: 168

Ala Arg Ser Arg Gly Ala Ala Tyr Phe Asp Tyr
1               5                   10

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcctcc ctgtctgcat ctgtaggaga cagagtcacc    60
atcacttgcc aggcgaatca ggacattagc aacttttaa attggtatca gcagagacca   120
gggaaagccc ctaacctcct gatctatgct gcatccaatt tggaaacagg gtcccatca   180 aggttcagtg aagtggatc tgggacagat tttactttca ccatcagcag cctgcagcct   240
gaagatattg caacatatta ctgtcaacat tatgataatt ttccattcac tttcggccct   300
gggaccaagg tggatatcaa a                                             321

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Gln Ala Asn Gln Asp Ile Ser Asn Phe
            20                  25                  30

Leu Asn Trp Tyr Gln Gln Arg Pro Gly Lys Ala Pro Asn Leu Leu Ile
        35                  40                  45

Tyr Ala Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Tyr Asp Asn Phe Pro Phe
                85                  90                  95

Thr Phe Gly Pro Gly Thr Lys Val Asp Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
caggacatta gcaacttt                                                  18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

```
Gln Asp Ile Ser Asn Phe
 1               5
```

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gctgcatcc                                                                    9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

```
Ala Ala Ser
 1
```

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacattatg ataattttcc attcact                                               27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

```
Gln His Tyr Asp Asn Phe Pro Phe Thr
 1               5
```

<210> SEQ ID NO 177
<211> LENGTH: 363
<212> TYPE: DNA
<213> ORGANISM: Artificial Sequence
<220> FEATURE:
<223> OTHER INFORMATION: Synthetic

<400> SEQUENCE: 177
cagctgcagc tgcaggagtc gggcccagga ctggtgaacc cttcggagac cctgtccctc           60
acctgctctg tctctggtgg ctccatcagc agtgttaatt actactgggg ctggatccgc          120
cagtccccag ggaagggact ggagtggatt gggagtatct attatactgg gagtaccgac          180
tacaacccgt ccctcaagaa tcgagtcacc atatccgtag acacgtccaa gaaccagttc          240
tccctgaagc agacttctgt gaccgccgca gacacggctg tctattactg tgcgagacat          300
gtggcactgg ctgggggggc ttttgatatc tggggccagg gacaatggt caccgtctct          360 tca                                                                        363

<210> SEQ ID NO 178

<211> LENGTH: 121
<212> TYPE: PRT
<213> ORGANISM: Artificial Sequence
<220> FEATURE:
<223> OTHER INFORMATION: Synthetic

<400> SEQUENCE: 178

```
Gln Leu Gln Leu Gln Glu Ser Gly Pro Gly Leu Val Asn Pro Ser Glu
 1               5                  10                  15
Thr Leu Ser Leu Thr Cys Ser Val Ser Gly Gly Ser Ile Ser Ser Val
            20                  25                  30
Asn Tyr Tyr Trp Gly Trp Ile Arg Gln Ser Pro Gly Lys Gly Leu Glu
        35                  40                  45
Trp Ile Gly Ser Ile Tyr Tyr Thr Gly Ser Thr Asp Tyr Asn Pro Ser
    50                  55                  60
Leu Lys Asn Arg Val Thr Ile Ser Val Asp Thr Ser Lys Asn Gln Phe
65                  70                  75                  80
Ser Leu Lys Gln Thr Ser Val Thr Ala Ala Asp Thr Ala Val Tyr Tyr
                85                  90                  95
Cys Ala Arg His Val Ala Leu Ala Gly Gly Ala Phe Asp Ile Trp Gly
            100                 105                 110
Gln Gly Thr Met Val Thr Val Ser Ser
        115                 120
```

<210> SEQ ID NO 179
<211> LENGTH: 30
<212> TYPE: DNA
<213> ORGANISM: Artificial Sequence
<220> FEATURE:
<223> OTHER INFORMATION: Synthetic

<400> SEQUENCE: 179
ggtggctcca tcagcagtgt taattactac                                      30

<210> SEQ ID NO 180
<211> LENGTH: 10
<212> TYPE: PRT
<213> ORGANISM: Artificial Sequence
<220> FEATURE:
<223> OTHER INFORMATION: Synthetic

<400> SEQUENCE: 180

```
Gly Gly Ser Ile Ser Ser Val Asn Tyr Tyr
 1               5                  10
```

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181
atctattata ctgggagtac c                                               21

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Ile Tyr Tyr Thr Gly Ser Thr
 1               5

<210> SEQ ID NO 183
<211> LENGTH: 39
<212> TYPE: DNA
<213> ORGANISM: Artificial Sequence
<220> FEATURE:
<223> OTHER INFORMATION: Synthetic

<400> SEQUENCE: 183
gcgagacatg tggcactggc tgggggggct tttgatatc            39

<210> SEQ ID NO 184
<211> LENGTH: 13
<212> TYPE: PRT
<213> ORGANISM: Artificial Sequence
<220> FEATURE:
<223> OTHER INFORMATION: Synthetic

<400> SEQUENCE: 184

Ala Arg His Val Ala Leu Ala Gly Gly Ala Phe Asp Ile
 1               5                  10

<210> SEQ ID NO 185
<211> LENGTH: 315
<212> TYPE: DNA
<213> ORGANISM: Artificial Sequence
<220> FEATURE:
<223> OTHER INFORMATION: Synthetic

<400> SEQUENCE: 185
gaaattgtgt tgacgcagtc tccaggcacc ctgtctttgt ctccagggga aagagccacc     60
ctctcctgca gggccagtca gagtgttagt agcagcttct taggctggta ccaacagaaa    120
cctggccagg ctcccaggct cctcatctat ggttcttcca ccagggccac tggcatccca    180
gacaggttca gtggcagtgg gtctgggaca gacttcaata tcaccatcag cagactggag    240
cctgaagatt ttgcagtgta ttactgtcag cagtttggta ggtccttcgg ccctgggacc    300
aagctggaga tcaaa                                                     315

<210> SEQ ID NO 186
<211> LENGTH: 105
<212> TYPE: PRT
<213> ORGANISM: Artificial Sequence
<220> FEATURE:
<223> OTHER INFORMATION: Synthetic

<400> SEQUENCE: 186

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Phe Leu Gly Trp Tyr Gln Gln Lys Pro Gly Gln Ala Pro Arg Leu Leu
            35                  40                  45

Ile Tyr Gly Ser Ser Thr Arg Ala Thr Gly Ile Pro Asp Arg Phe Ser
        50                  55                  60

Gly Ser Gly Ser Gly Thr Asp Phe Asn Ile Thr Ile Ser Arg Leu Glu
 65                  70                  75                  80

Pro Glu Asp Phe Ala Val Tyr Tyr Cys Gln Gln Phe Gly Arg Ser Phe
                85                  90                  95

Gly Pro Gly Thr Lys Leu Glu Ile Lys
            100                 105

<210> SEQ ID NO 187
<211> LENGTH: 21
<212> TYPE: DNA
<213> ORGANISM: Artificial Sequence
<220> FEATURE:
<223> OTHER INFORMATION: Synthetic

<400> SEQUENCE: 187
cagagtgtta gtagcagctt c                                              21

<210> SEQ ID NO 188
<211> LENGTH: 7
<212> TYPE: PRT
<213> ORGANISM: Artificial Sequence
<220> FEATURE:
<223> OTHER INFORMATION: Synthetic

<400> SEQUENCE: 188

Gln Ser Val Ser Ser Ser Phe
 1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 ggttcttcc                                                             9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Gly Ser Ser
 1

<210> SEQ ID NO 191
<211> LENGTH: 18
<212> TYPE: DNA
<213> ORGANISM: Artificial Sequence
<220> FEATURE:
<223> OTHER INFORMATION: Synthetic

<400> SEQUENCE: 191
cagcagtttg gtaggtcc                                                  18

<210> SEQ ID NO 192
<211> LENGTH: 6
<212> TYPE: PRT
<213> ORGANISM: Artificial Sequence
<220> FEATURE:
<223> OTHER INFORMATION: Synthetic

<400> SEQUENCE: 192

Gln Gln Phe Gly Arg Ser
 1               5

<210> SEQ ID NO 193

<211> LENGTH: 360
<212> TYPE: DNA
<213> ORGANISM: Artificial Sequence
<220> FEATURE:
<223> OTHER INFORMATION: Synthetic

<400> SEQUENCE: 193

```
caggtgcagc tggtggagtc tgggggaggc ttggtcaagc ctggagggtc cctgagactc      60
tcctgcgcag cctctggatt caccttcagt gactattaca tgaactggat ccgccaggct     120
ccagggaagg ggctggagtg gatttcatat attagtagtg gtggtagtac cacatactac     180
gcagactctg tgaagggccg attcaccatc tccagggaca cgccaagaa ctcactgtat      240
ctgcaaatga acagcctgag agccgaggac acggccgtgt attactgtgc gagagatggg     300
aagtacaaca cctcgccggg ggactactgg ggccagggaa ccctggtcac cgtctcctca     360
```

<210> SEQ ID NO 194
<211> LENGTH: 120
<212> TYPE: PRT
<213> ORGANISM: Artificial Sequence
<220> FEATURE:
<223> OTHER INFORMATION: Synthetic

<400> SEQUENCE: 194

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Ile
        35                  40                  45

Ser Tyr Ile Ser Ser Gly Gly Ser Thr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Lys Tyr Asn Thr Ser Pro Gly Asp Tyr Trp Gly Gln
            100                 105                 110

Gly Thr Leu Val Thr Val Ser Ser
        115                 120
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

```
ggattcacct tcagtgacta ttac                                              24
```

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

```
Gly Phe Thr Phe Ser Asp Tyr Tyr
 1               5
```

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
attagtagtg gtggtagtac caca                                              24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Ser Gly Gly Ser Thr Thr
1               5

<210> SEQ ID NO 199
<211> LENGTH: 39
<212> TYPE: DNA
<213> ORGANISM: Artificial Sequence
<220> FEATURE:
<223> OTHER INFORMATION: Synthetic

<400> SEQUENCE: 199
gcgagagatg ggaagtacaa cacctcgccg ggggactac                              39

<210> SEQ ID NO 200
<211> LENGTH: 13
<212> TYPE: PRT
<213> ORGANISM: Artificial Sequence
<220> FEATURE:
<223> OTHER INFORMATION: Synthetic

<400> SEQUENCE: 200

Ala Arg Asp Gly Lys Tyr Asn Thr Ser Pro Gly Asp Tyr
1               5                   10

<210> SEQ ID NO 201
<211> LENGTH: 318
<212> TYPE: DNA
<213> ORGANISM: Artificial Sequence
<220> FEATURE:
<223> OTHER INFORMATION: Synthetic

<400> SEQUENCE: 201
gaaattgtgt tgacgcagtc tccagacttt cagtctgtga ctccaaagga gaaagtcacc        60
atcacctgcc gggccagtca gtccattggt agtagcttac actggtacca gcagaaacca       120
gatcagtctc caaagctcct catcaagtat gcttcccagt ccttctcagg ggtcccctcg       180
aggttcagtg gcagtggatc tgggacagat ttcacccctc ccatcaatag cctggaagct       240
gaagatgctg ctacgtatta ctgtcttcag agtagtagtt acggacgttt cggccaaggg       300
accaaagtgg atatcaaa                                                    318

<210> SEQ ID NO 202
<211> LENGTH: 106
<212> TYPE: PRT
<213> ORGANISM: Artificial Sequence
<220> FEATURE:
<223> OTHER INFORMATION: Synthetic

<400> SEQUENCE: 202

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Leu Gln Ser Ser Ser Leu Arg Thr
                85                  90                  95

Phe Gly Gln Gly Thr Lys Val Asp Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagtccattg gtagtagc                                                  18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Gly Ser Ser
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 tatgcttcc                                                             9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Tyr Ala Ser
1

<210> SEQ ID NO 207
<211> LENGTH: 24
<212> TYPE: DNA
<213> ORGANISM: Artificial Sequence
<220> FEATURE:
<223> OTHER INFORMATION: Synthetic

<400> SEQUENCE: 207
cttcagagta gtagtttacg gacg                                  24

<210> SEQ ID NO 208
<211> LENGTH: 8
<212> TYPE: PRT
<213> ORGANISM: Artificial Sequence
<220> FEATURE:
<223> OTHER INFORMATION: Synthetic

<400> SEQUENCE: 208

Leu Gln Ser Ser Ser Leu Arg Thr
1               5

<210> SEQ ID NO 209
<211> LENGTH: 360
<212> TYPE: DNA
<213> ORGANISM: Artificial Sequence
<220> FEATURE:
<223> OTHER INFORMATION: Synthetic

<400> SEQUENCE: 209
caggtgcagc tggtggagtc tgggggaggc ttggtcaagc ctggagggtc cctgagactc      60
tcctgtgcag cctctggatt caccttcagt gactactaca tgaactggat ccgccaggct     120
ccagggaagg ggctggagtg gatttcatac attagtagta gtggtagtac cacatactac     180
gcagactctg tgaagggccg attcaccatc tccagggaca acgccaagaa ctcactgttt     240
ctgcaaatga acagcctgag aggcgaggac acggccgtgt attattgtgc gagagatggg     300
agatacaaca ccgtcgccgg ggactactgg ggccagggaa ccacggtcac cgtctcctca     360

<210> SEQ ID NO 210
<211> LENGTH: 120
<212> TYPE: PRT
<213> ORGANISM: Artificial Sequence
<220> FEATURE:
<223> OTHER INFORMATION: Synthetic

<400> SEQUENCE: 210

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Ile
        35                  40                  45

Ser Tyr Ile Ser Ser Ser Gly Ser Thr Thr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Gly Glu Asp Thr Ala Val Tyr Tyr Cys
                85                  90                  95

Ala Arg Asp Gly Arg Tyr Asn Thr Val Ala Gly Asp Tyr Trp Gly Gln
            100                 105                 110

Gly Thr Thr Val Thr Val Ser Ser
        115                 120

<210> SEQ ID NO 211
<211> LENGTH: 24

<212> TYPE: DNA
<213> ORGANISM: Artificial Sequence
<220> FEATURE:
<223> OTHER INFORMATION: Synthetic

<400> SEQUENCE: 211
ggattcacct tcagtgacta ctac                                      24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Asp Tyr Tyr
 1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attagtagta gtggtagtac caca                                      24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Ser Ser Gly Ser Thr Thr
 1               5

<210> SEQ ID NO 215
<211> LENGTH: 39
<212> TYPE: DNA
<213> ORGANISM: Artificial Sequence
<220> FEATURE:
<223> OTHER INFORMATION: Synthetic

<400> SEQUENCE: 215
gcgagagatg ggagatacaa caccgtcgcc ggggactac                       39

<210> SEQ ID NO 216
<211> LENGTH: 13
<212> TYPE: PRT
<213> ORGANISM: Artificial Sequence
<220> FEATURE:
<223> OTHER INFORMATION: Synthetic

<400> SEQUENCE: 216

Ala Arg Asp Gly Arg Tyr Asn Thr Val Ala Gly Asp Tyr
 1               5                  10

<210> SEQ ID NO 217
<211> LENGTH: 321
<212> TYPE: DNA
<213> ORGANISM: Artificial Sequence
<220> FEATURE:
<223> OTHER INFORMATION: Synthetic -continued

<400> SEQUENCE: 217

```
gaaattgtga tgacgcagtc tccagacttt cagtctgtgg ctccaaagga gaaagtcacc      60
atcacctgcc gggccagtca gaacattggt ggtagcttac actggtacca gcagaaacca     120
gatcagtctc caaagctcct catcaagtat gcttcccagt ccttctcagg gtcccctcg      180 aggttcagtg gcagtggatc tgggacagat ttcaccctca ccatcaatag cctggaagct     240
gaagatgctg caacgtatta ctgtcttcag agttacactt tacggacgtt cggccaaggg     300
accaaggtgg agatcaaacg a                                                321
```

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

Glu Ile Val Met Thr Gln Ser Pro Asp Phe Gln Ser Val Ala Pro Lys
1               5                   10                  15

Glu Lys Val Thr Ile Thr Cys Arg Ala Ser Gln Asn Ile Gly Gly Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Leu Gln Ser Tyr Thr Leu Arg Thr
                85                  90                  95

Phe Gly Gln Gly Thr Lys Val Glu Ile Lys Arg
            100                 105

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219

```
cagaacattg gtggtagc                                                    18
```

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Asn Ile Gly Gly Ser
1               5

<210> SEQ ID NO 221
<211> LENGTH: 9
<212> TYPE: DNA
<213> ORGANISM: Artificial Sequence
<220> FEATURE:
<223> OTHER INFORMATION: Synthetic

```
<400> SEQUENCE: 221 tatgcttcc                                                                9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Tyr Ala Ser
 1

<210> SEQ ID NO 223
<211> LENGTH: 24
<212> TYPE: DNA
<213> ORGANISM: Artificial Sequence
<220> FEATURE:
<223> OTHER INFORMATION: Synthetic

<400> SEQUENCE: 223
cttcagagtt acactttacg gacg                                              24

<210> SEQ ID NO 224
<211> LENGTH: 8
<212> TYPE: PRT
<213> ORGANISM: Artificial Sequence
<220> FEATURE:
<223> OTHER INFORMATION: Synthetic

<400> SEQUENCE: 224

Leu Gln Ser Tyr Thr Leu Arg Thr
 1               5

<210> SEQ ID NO 225
<211> LENGTH: 360
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtcaagc ctggagggtc cctgagactc        60
tcctgtgcag cctctggatt caccttcagt gactactaca tgaactggat ccgccaggct       120
ccagggaagg gctggagtg gtttcatat attagtagta gtggcagcag tatttattac         180
gcagactctg tgaagggccg attcaccatc tccagggaca acgccaagaa ctcactgtat       240
ctgctaatga acagcctgag agccgaggac acggccgtgt attactgtgc gagagatggg       300
aagtataaca gttcgccggg ggactactgg ggccagggaa ccctggtcac cgtctcctca       360

<210> SEQ ID NO 226
<211> LENGTH: 120
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30
```

```
Tyr Met Asn Trp Ile Arg Gln Ala Pro Gly Lys Gly Leu Glu Trp Val
         35                  40                  45

Ser Tyr Ile Ser Ser Ser Gly Ser Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Leu Met Asn Ser Leu Arg Ala Glu Asp Thr Ala Val Tyr Tyr Cys
                 85                  90                  95

Ala Arg Asp Gly Lys Tyr Asn Ser Ser Pro Gly Asp Tyr Trp Gly Gln
                100                 105                 110

Gly Thr Leu Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct tcagtgacta ctac                                          24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Phe Ser Asp Tyr Tyr
 1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtagta gtggcagcag tatt                                          24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Ser Ser Gly Ser Ser Ile
 1               5

<210> SEQ ID NO 231
<211> LENGTH: 39
<212> TYPE: DNA
<213> ORGANISM: Artificial Sequence
<220> FEATURE:
<223> OTHER INFORMATION: Synthetic

<400> SEQUENCE: 231
```

```
gcgagagatg ggaagtataa cagttcgccg ggggactac                                39
```

<210> SEQ ID NO 232
<211> LENGTH: 13
<212> TYPE: PRT
<213> ORGANISM: Artificial Sequence
<220> FEATURE:
<223> OTHER INFORMATION: Synthetic

<400> SEQUENCE: 232

```
Ala Arg Asp Gly Lys Tyr Asn Ser Ser Pro Gly Asp Tyr
  1               5                  10
```

<210> SEQ ID NO 233
<211> LENGTH: 324
<212> TYPE: DNA
<213> ORGANISM: Artificial Sequence
<220> FEATURE:
<223> OTHER INFORMATION: Synthetic

<400> SEQUENCE: 233

```
gacatccaga tgacccagtc tccatcctca ctgtctgcat ctgtaggaga cagagtcacc        60
atcgcttgtc gggcgagtca gggcattagc aattatttag cctggtttca gcagaaacca       120
gggaaagccc ctaagtccct gatctatgct gcatccagtt tgcaaagtgg ggtcccatca       180
aagttcagcg gcagtggatc tgggacagat ttcactctca ccatcagcag cctgcagcct       240
gaagattttg caacttatta ctgccaacag tataacagtt acccgctcac tttcggcgga       300
gggaccaagg tggaaatcaa acga                                              324
```

<210> SEQ ID NO 234
<211> LENGTH: 108
<212> TYPE: PRT
<213> ORGANISM: Artificial Sequence
<220> FEATURE:
<223> OTHER INFORMATION: Synthetic

<400> SEQUENCE: 234

```
Asp Ile Gln Met Thr Gln Ser Pro Ser Leu Ser Ala Ser Val Gly
  1               5                  10                  15

Asp Arg Val Thr Ile Ala Cys Arg Ala Ser Gln Gly Ile Ser Asn Tyr
                 20                  25                  30

Leu Ala Trp Phe Gln Gln Lys Pro Gly Lys Ala Pro Lys Ser Leu Ile
             35                  40                  45

Tyr Ala Ala Ser Ser Leu Gln Ser Gly Val Pro Ser Lys Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys Arg
            100                 105
```

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

```
cagggcatta gcaattat                                                      18
```

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Gly Ile Ser Asn Tyr
 1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 gctgcatcc                                                                  9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ala Ala Ser
 1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
caacagtata acagttaccc gctcact                                             27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Tyr Asn Ser Tyr Pro Leu Thr
 1               5

<210> SEQ ID NO 241
<211> LENGTH: 360
<212> TYPE: DNA
<213> ORGANISM: Artificial Sequence
<220> FEATURE:
<223> OTHER INFORMATION: Synthetic

<400> SEQUENCE: 241
gaggtgcagc tggtggagtc tgggggaggc ttggtcaagc ctggagggtc cctgagactc         60
tcctgtgcag cctctggatt caccttcagt gactactaca tgaactggat ccgccaggct        120
ccagggaagg ggctggagtg ggtttcatat attagtagta gtggcagtag tatttattac        180

```
gcagactctg tgaagggccg attcaccatc tccagggaca acgccaagaa ctcactgtat    240
ctgctaatga acagcctgag agccgaggac acggccgtgt attactgtgc gagagatggg    300
aagtataaca gctcgccggg ggactactgg ggccagggaa ccctggtcac tgtctcctca    360
```

<210> SEQ ID NO 242
<211> LENGTH: 120
<212> TYPE: PRT
<213> ORGANISM: Artificial Sequence
<220> FEATURE:
<223> OTHER INFORMATION: Synthetic

<400> SEQUENCE: 242

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Asn Trp Ile Arg Gln Ala Pro Gly Lys Gly Leu Glu Trp Val
         35                  40                  45

Ser Tyr Ile Ser Ser Ser Gly Ser Ser Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Leu Met Asn Ser Leu Arg Ala Glu Asp Thr Ala Val Tyr Tyr Cys
                 85                  90                  95

Ala Arg Asp Gly Lys Tyr Asn Ser Ser Pro Gly Asp Tyr Trp Gly Gln
            100                 105                 110

Gly Thr Leu Val Thr Val Ser Ser
        115                 120
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243

```
ggattcacct tcagtgacta ctac                                            24
```

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Phe Ser Asp Tyr Tyr
  1               5
```

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245

```
attagtagta gtggcagtag tatt                                            24
```

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Ser Ser Gly Ser Ser Ile
1               5

<210> SEQ ID NO 247
<211> LENGTH: 39
<212> TYPE: DNA
<213> ORGANISM: Artificial Sequence
<220> FEATURE:
<223> OTHER INFORMATION: Synthetic

<400> SEQUENCE: 247
gcgagagatg ggaagtataa cagctcgccg ggggactac                       39

<210> SEQ ID NO 248
<211> LENGTH: 13
<212> TYPE: PRT
<213> ORGANISM: Artificial Sequence
<220> FEATURE:
<223> OTHER INFORMATION: Synthetic

<400> SEQUENCE: 248

Ala Arg Asp Gly Lys Tyr Asn Ser Ser Pro Gly Asp Tyr
1               5                   10

<210> SEQ ID NO 249
<211> LENGTH: 318
<212> TYPE: DNA
<213> ORGANISM: Artificial Sequence
<220> FEATURE:
<223> OTHER INFORMATION: Synthetic

<400> SEQUENCE: 249
gaaattgtgc tgactcagtc tccagacttt cagtctgtga ctccaaagga gaaagtcacc    60
atcacctgcc gggccagtca gagcattggt ggtagcttac actggtacca gcagaaacca   120
gatcagtctc caaagctcct catcaagtat gcttcccagt ccttctcagg ggtcccctcg   180
aggttcagtg gcagtggatc tgggacagat ttcaccctca ccatcaatag cctggaagct   240
gaagatgctg caacgtatta ctgtcttcag agtagtagtt tacggacgtt cggccaaggg   300
accaaggtgg aaatcaaa                                                 318

<210> SEQ ID NO 250
<211> LENGTH: 106
<212> TYPE: PRT
<213> ORGANISM: Artificial Sequence
<220> FEATURE:
<223> OTHER INFORMATION: Synthetic

<400> SEQUENCE: 250

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Gly Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly

```
                50                  55                  60
Ser Gly Ser Gly Thr Asp Phe Thr Leu Thr Ile Asn Ser Leu Glu Ala
 65                  70                  75                  80

Glu Asp Ala Ala Thr Tyr Tyr Cys Leu Gln Ser Ser Leu Arg Thr
                 85                  90                  95

Phe Gly Gln Gly Thr Lys Val Glu Ile Lys
            100                 105
```

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cagagcattg gtggtagc                                                 18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

```
Gln Ser Ile Gly Gly Ser
 1               5
```

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 tatgcttcc                                                            9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

```
Tyr Ala Ser
 1
```

<210> SEQ ID NO 255
<211> LENGTH: 24
<212> TYPE: DNA
<213> ORGANISM: Artificial Sequence
<220> FEATURE:
<223> OTHER INFORMATION: Synthetic

<400> SEQUENCE: 255
cttcagagta gtagtttacg gacg                                          24

<210> SEQ ID NO 256
<211> LENGTH: 8
<212> TYPE: PRT
<213> ORGANISM: Artificial Sequence
<220> FEATURE:

<223> OTHER INFORMATION: Synthetic

<400> SEQUENCE: 256

Leu Gln Ser Ser Ser Leu Arg Thr
1               5

<210> SEQ ID NO 257
<211> LENGTH: 363
<212> TYPE: DNA
<213> ORGANISM: Artificial Sequence
<220> FEATURE:
<223> OTHER INFORMATION: Synthetic

<400> SEQUENCE: 257
gaggtgcagc tggtggagtc tgggggaggc ttggtcaagc ctggagggtc cctgagactc    60
tcctgtgcag cctctggatt caccttcagt gactactaca tgaactggat ccgccaggct   120
ccagggaagg gctggagtg gtttcatac attagtagta gtggtaattc catatactac     180
gcagactctg tgaagggccg attcaccatc tccagggaca cgccaagaa ctcactgttt    240 ctgcagatga gcagcctgag agccgaggac acggccgtgt attactgtgc gagagatggg   300
aggtataacg accgtcgccg ggggtactac tggggccagg gaaccctggt caccgtctcc   360
tca                                                                 363

<210> SEQ ID NO 258
<211> LENGTH: 121
<212> TYPE: PRT
<213> ORGANISM: Artificial Sequence
<220> FEATURE:
<223> OTHER INFORMATION: Synthetic

<400> SEQUENCE: 258

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Gly Asn Ser Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Asp Gly Arg Tyr Asn Asp Arg Arg Arg Gly Tyr Tyr Trp Gly
            100                 105                 110

Gln Gly Thr Leu Val Thr Val Ser Ser
        115                 120

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggattcacct tcagtgacta ctac                                           24

<210> SEQ ID NO 260

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Ser Asp Tyr Tyr
1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
attagtagta gtggtaattc cata                                          24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Ser Ser Gly Asn Ser Ile
1               5

<210> SEQ ID NO 263
<211> LENGTH: 42
<212> TYPE: DNA
<213> ORGANISM: Artificial Sequence
<220> FEATURE:
<223> OTHER INFORMATION: Synthetic

<400> SEQUENCE: 263
gcgagagatg ggaggtataa cgaccgtcgc cgggggtact ac                      42

<210> SEQ ID NO 264
<211> LENGTH: 14
<212> TYPE: PRT
<213> ORGANISM: Artificial Sequence
<220> FEATURE:
<223> OTHER INFORMATION: Synthetic

<400> SEQUENCE: 264

Ala Arg Asp Gly Arg Tyr Asn Asp Arg Arg Gly Tyr Tyr
1               5                   10

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265
gaaattgtga tgacgcagtc tccagacttt cagtctgtga ctccaaagga gaaagtcacc   60
atcacctgcc gggccagtca gagcattggt agtagcttac actggtacca gcagaaacca  120
gatcagtctc caaaactcct catcaagtat gcttcccagt ccttctcagg ggtcccctcg  180
aggttcagtg gcagtggatc tgggacagat ttcaccctca ccatcaatag cctggaagct  240

```
gaagatgctg caacgtatta ctgtcttcag agtagtagtt tacggacgtt cggccaaggg    300
accaaggtgg agatcaaacg a                                              321
```

<210> SEQ ID NO 266
<211> LENGTH: 107
<212> TYPE: PRT
<213> ORGANISM: Artificial Sequence
<220> FEATURE:
<223> OTHER INFORMATION: Synthetic

<400> SEQUENCE: 266

```
Glu Ile Val Met Thr Gln Ser Pro Asp Phe Gln Ser Val Thr Pro Lys
  1               5                  10                  15

Glu Lys Val Thr Ile Thr Cys Arg Ala Ser Gln Ser Ile Gly Ser Ser
             20                  25                  30

Leu His Trp Tyr Gln Gln Lys Pro Asp Gln Ser Pro Lys Leu Leu Ile
         35                  40                  45

Lys Tyr Ala Ser Gln Ser Phe Ser Gly Val Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Leu Gln Ser Ser Ser Leu Arg Thr
                 85                  90                  95

Phe Gly Gln Gly Thr Lys Val Glu Ile Lys Arg
            100                 105
```

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267

```
cagagcattg gtagtagc                                                   18
```

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

```
Gln Ser Ile Gly Ser Ser
  1               5
```

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269

```
tatgcttcc                                                              9
```

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Tyr Ala Ser
 1

<210> SEQ ID NO 271
<211> LENGTH: 24
<212> TYPE: DNA
<213> ORGANISM: Artificial Sequence
<220> FEATURE:
<223> OTHER INFORMATION: Synthetic

<400> SEQUENCE: 271
cttcagagta gtagtttacg gacg                                              24

<210> SEQ ID NO 272
<211> LENGTH: 8
<212> TYPE: PRT
<213> ORGANISM: Artificial Sequence
<220> FEATURE:
<223> OTHER INFORMATION: Synthetic

<400> SEQUENCE: 272

Leu Gln Ser Ser Ser Leu Arg Thr
 1               5

<210> SEQ ID NO 273
<211> LENGTH: 360
<212> TYPE: DNA
<213> ORGANISM: Artificial Sequence
<220> FEATURE:
<223> OTHER INFORMATION: Synthetic

<400> SEQUENCE: 273
gaggtgcagc tggtggagtc tgggggaggc ttggtcaagc ctggagggtc cctgagactc        60
tcctgtgcag cctctggatt caccttcagt gactactaca tgaactggat ccgccaggct       120
ccagggaagg ggctggagtg gatttcatat cttagtagta gtggtagtgc cacatactac       180
gcagactctg tgaagggccg attcaccatc tccagggaca acgccaagaa ctcactgtat       240
ctgcaaatga acagcctgag agccgaggac acggccgtgt attattgtgc gagagatggg       300
aagtacaaca ccgtcgccgg ggactactgg ggccagggaa ccacggtcac cgtctcctca       360

<210> SEQ ID NO 274
<211> LENGTH: 120
<212> TYPE: PRT
<213> ORGANISM: Artificial Sequence
<220> FEATURE:
<223> OTHER INFORMATION: Synthetic

<400> SEQUENCE: 274

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Ile
        35                  40                  45

Ser Tyr Leu Ser Ser Ser Gly Ser Ala Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                    85                  90                  95
Ala Arg Asp Gly Lys Tyr Asn Thr Val Ala Gly Asp Tyr Trp Gly Gln
            100                 105                 110

Gly Thr Thr Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggattcacct tcagtgacta ctac                                          24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Ser Asp Tyr Tyr
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
cttagtagta gtggtagtgc caca                                          24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Leu Ser Ser Ser Gly Ser Ala Thr
1               5

<210> SEQ ID NO 279
<211> LENGTH: 39
<212> TYPE: DNA
<213> ORGANISM: Artificial Sequence
<220> FEATURE:
<223> OTHER INFORMATION: Synthetic

<400> SEQUENCE: 279
gcgagagatg ggaagtacaa caccgtcgcc ggggactac                          39

<210> SEQ ID NO 280
<211> LENGTH: 13
<212> TYPE: PRT
<213> ORGANISM: Artificial Sequence
<220> FEATURE:
<223> OTHER INFORMATION: Synthetic

<400> SEQUENCE: 280
```

Ala Arg Asp Gly Lys Tyr Asn Thr Val Ala Gly Asp Tyr
1               5                   10

<210> SEQ ID NO 281
<211> LENGTH: 324
<212> TYPE: DNA
<213> ORGANISM: Artificial Sequence
<220> FEATURE:
<223> OTHER INFORMATION: Synthetic

<400> SEQUENCE: 281
gacatccagt tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tacaaagtgg ggtcccatca     180
aggttcagcg gcagtggatc tgggacagaa ttcactctca caatcagcag cctgcagcct     240
gaagattttg caacttatta ctgtctacaa cataatagtt acccgtacac ttttggccag     300
gggaccaagg tagagatcaa acga                                             324

<210> SEQ ID NO 282
<211> LENGTH: 108
<212> TYPE: PRT
<213> ORGANISM: Artificial Sequence
<220> FEATURE:
<223> OTHER INFORMATION: Synthetic

<400> SEQUENCE: 282

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Val Glu Ile Lys Arg
            100                 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283
cagggcatta gaaatgat                                                    18

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

```
<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 gctgcatcc                                                                9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Ala Ala Ser
 1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
ctacaacata atagttaccc gtacact                                           27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Leu Gln His Asn Ser Tyr Pro Tyr Thr
 1               5

<210> SEQ ID NO 289
<211> LENGTH: 360
<212> TYPE: DNA
<213> ORGANISM: Artificial Sequence
<220> FEATURE:
<223> OTHER INFORMATION: Synthetic

<400> SEQUENCE: 289
gaggtgcagc tggtggagtc tgggggaggc ttggtcaagc ctggagggtc cctgagactc        60
tcctgtgcag cctctggatt caccttcagt gactactaca tgaactggat ccgccaggct       120
ccagggaagg ggctggagtg gatttcatac attagtagta gtgatgatac cacatactac       180
gcagactctg tgaagggccg attcaccata tccagggaca cgccaagaa ctcactgtat        240 ctgcaaatga acagcctgag agccgaggac acggccgtgt attattgtgc gagagatggg       300
aagtacaaca ccgtcgccgg ggaccactgg ggccagggaa ccctggtcac cgtctcctca       360

<210> SEQ ID NO 290
<211> LENGTH: 120
<212> TYPE: PRT
```

Gln Gly Ile Arg Asn Asp
 1               5

<213> ORGANISM: Artificial Sequence
<220> FEATURE:
<223> OTHER INFORMATION: Synthetic

<400> SEQUENCE: 290

```
Glu Val Gln Leu Val Glu Ser Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Asn Trp Ile Arg Gln Ala Pro Gly Lys Gly Leu Glu Trp Ile
         35                  40                  45

Ser Tyr Ile Ser Ser Ser Asp Asp Thr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Lys Tyr Asn Thr Val Ala Gly Asp His Trp Gly Gln
            100                 105                 110

Gly Thr Leu Val Thr Val Ser Ser
        115                 120
```

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct tcagtgacta ctac                                           24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

```
Gly Phe Thr Phe Ser Asp Tyr Tyr
  1               5
```

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagtagta gtgatgatac caca                                           24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

```
Ile Ser Ser Ser Asp Asp Thr Thr
  1               5
```

<210> SEQ ID NO 295
<211> LENGTH: 39
<212> TYPE: DNA
<213> ORGANISM: Artificial Sequence
<220> FEATURE:
<223> OTHER INFORMATION: Synthetic

<400> SEQUENCE: 295
gcgagagatg ggaagtacaa caccgtcgcc ggggaccac                  39

<210> SEQ ID NO 296
<211> LENGTH: 13
<212> TYPE: PRT
<213> ORGANISM: Artificial Sequence
<220> FEATURE:
<223> OTHER INFORMATION: Synthetic

<400> SEQUENCE: 296

Ala Arg Asp Gly Lys Tyr Asn Thr Val Ala Gly Asp His
 1               5                  10

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gaaattgtga tgacacagtc tccagacttt cagtctgtgg ctccaaagga gaaagtcacc    60
atcacctgcc gggccagtca gaacattggt agtagcttac actggtacca gcagaaacca   120
gatcagtctc caaagctcct catcaagtat gcttcccagt ccttctcagg ggtcccctcg   180
aggttcagtg gcagtggatc tgggacagat ttcaccctca ccatcaatag cctggaagct   240
gaagatgctg caacgtatta ctgtcttcag agttatactt taaggacgtt cggccaaggg   300
accaaggtgg agatcaaacg a                                            321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Glu Ile Val Met Thr Gln Ser Pro Asp Phe Gln Ser Val Ala Pro Lys
 1               5                  10                  15

Glu Lys Val Thr Ile Thr Cys Arg Ala Ser Gln Asn Ile Gly Ser Ser
             20                  25                  30

Leu His Trp Tyr Gln Gln Lys Pro Asp Gln Ser Pro Lys Leu Leu Ile
         35                  40                  45

Lys Tyr Ala Ser Gln Ser Phe Ser Gly Val Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Leu Gln Ser Tyr Thr Leu Arg Thr
                 85                  90                  95

Phe Gly Gln Gly Thr Lys Val Glu Ile Lys Arg
            100                 105

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagaacattg gtagtagc                                                 18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Asn Ile Gly Ser Ser
1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 tatgcttcc                                                            9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Tyr Ala Ser
1

<210> SEQ ID NO 303
<211> LENGTH: 24
<212> TYPE: DNA
<213> ORGANISM: Artificial Sequence
<220> FEATURE:
<223> OTHER INFORMATION: Synthetic

<400> SEQUENCE: 303
cttcagagtt atactttaag gacg                                          24

<210> SEQ ID NO 304
<211> LENGTH: 8
<212> TYPE: PRT
<213> ORGANISM: Artificial Sequence
<220> FEATURE:
<223> OTHER INFORMATION: Synthetic

<400> SEQUENCE: 304

Leu Gln Ser Tyr Thr Leu Arg Thr
1               5

<210> SEQ ID NO 305
<211> LENGTH: 345
<212> TYPE: DNA

<213> ORGANISM: Artificial Sequence
<220> FEATURE:
<223> OTHER INFORMATION: Synthetic

<400> SEQUENCE: 305

```
gaggtgcagc tggtggagtc tgggggaggc ttggtacagc ctgggggtc cctgagactc        60 tcctgtgcag cctctggatt cacctttagc agttatgcca tgagctgggt ccgccaggct       120
ccagggaagg gctggagtg gtctcagct attagtggtc gtggttataa cgcagactac        180
gcagactccg tgaagggccg gttcaccatc tccagggaca attccaagaa cacgctgtat       240
ctgcaaatga acagcctgag agccgaagac acggccgtat attactgtgc gaaattggaa       300
tactttgact actggggcca gggaaccctg gtcactgtct cctca                      345
```

<210> SEQ ID NO 306
<211> LENGTH: 115
<212> TYPE: PRT
<213> ORGANISM: Artificial Sequence
<220> FEATURE:
<223> OTHER INFORMATION: Synthetic

<400> SEQUENCE: 306

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Tyr Asn Ala Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Glu Tyr Phe Asp Tyr Trp Gly Gln Gly Thr Leu Val Thr
            100                 105                 110

Val Ser Ser
        115
```

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307

```
ggattcacct ttagcagtta tgcc                                              24
```

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

```
Gly Phe Thr Phe Ser Ser Tyr Ala
 1               5
```

<210> SEQ ID NO 309

<211> LENGTH: 24
<212> TYPE: DNA
<213> ORGANISM: Artificial Sequence
<220> FEATURE:
<223> OTHER INFORMATION: Synthetic

<400> SEQUENCE: 309
attagtggtc gtggttataa cgca                                              24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Gly Arg Gly Tyr Asn Ala
 1               5

<210> SEQ ID NO 311
<211> LENGTH: 24
<212> TYPE: DNA
<213> ORGANISM: Artificial Sequence
<220> FEATURE:
<223> OTHER INFORMATION: Synthetic

<400> SEQUENCE: 311
gcgaaattgg aatactttga ctac                                              24

<210> SEQ ID NO 312
<211> LENGTH: 8
<212> TYPE: PRT
<213> ORGANISM: Artificial Sequence
<220> FEATURE:
<223> OTHER INFORMATION: Synthetic

<400> SEQUENCE: 312

Ala Lys Leu Glu Tyr Phe Asp Tyr
 1               5

<210> SEQ ID NO 313
<211> LENGTH: 321
<212> TYPE: DNA
<213> ORGANISM: Artificial Sequence
<220> FEATURE:
<223> OTHER INFORMATION: Synthetic

<400> SEQUENCE: 313
gacatccaga tgacccagtc tccttccacc ctgtctgcat ctgtaggaga cagagtcacc        60
atcacttgcc gggccagtca gagtattagt agctggttgg cctggtatca gcagaaacca       120
gggaaagccc ctaagctcct gatctataag gcgtctagtt tagaaagtgg ggtcccatca       180
aggttcagcg gcagtggatc tgggacagat tcactctca ccatcagcag cctgaggcct        240
gaagattttg caacttatta ctgccaacag tataatagtt accctctgac tttcggcgga      300
gggaccaagg tggagatcaa a                                                321

<210> SEQ ID NO 314
<211> LENGTH: 107
<212> TYPE: PRT
<213> ORGANISM: Artificial Sequence
<220> FEATURE:
<223> OTHER INFORMATION: Synthetic

<400> SEQUENCE: 314

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Arg Pro
65              70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
cagagtatta gtagctgg    18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

```
Gln Ser Ile Ser Ser Trp
1               5
```

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 aaggcgtct    9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

```
Lys Ala Ser
1
```

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
caacagtata atagttaccc tctgact 27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Gln Gln Tyr Asn Ser Tyr Pro Leu Thr
 1               5

<210> SEQ ID NO 321
<211> LENGTH: 345
<212> TYPE: DNA
<213> ORGANISM: Artificial Sequence
<220> FEATURE:
<223> OTHER INFORMATION: Synthetic

<400> SEQUENCE: 321
gaggtgcagc tggtggagtc tgggggaggc ttggtacagc ctggggggtc cctgagactc     60
tcctgtgcag cctctggatt caccttagc acctatgcca tgcactgggt ccgccaggct    120
ccagggaagg gctggagtg gtctcaagt attagtggtc gtggtcgtaa ctcagaccac    180
gcagactccg tgaagggccg gttcaccatc tccagagaca attccaagaa cacgctctat    240
ctacaaatga acagcctgag agccgaggac acggccgtat attactgtgc gaggaccgaa    300
tacttccacc actggggcca gggcaccctg gtcaccgtct cctca                    345

<210> SEQ ID NO 322
<211> LENGTH: 115
<212> TYPE: PRT
<213> ORGANISM: Artificial Sequence
<220> FEATURE:
<223> OTHER INFORMATION: Synthetic

<400> SEQUENCE: 322

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ser Ser Ile Ser Gly Arg Gly Arg Asn Ser Asp His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Glu Tyr Phe His His Trp Gly Gln Gly Thr Leu Val Thr
            100                 105                 110

Val Ser Ser
        115

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcacct ttagcaccta tgcc        24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Phe Thr Phe Ser Thr Tyr Ala
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
attagtggtc gtggtcgtaa ctca        24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Ser Gly Arg Gly Arg Asn Ser
1               5

<210> SEQ ID NO 327
<211> LENGTH: 24
<212> TYPE: DNA
<213> ORGANISM: Artificial Sequence
<220> FEATURE:
<223> OTHER INFORMATION: Synthetic

<400> SEQUENCE: 327
gcgaggaccg aatacttcca ccac        24

<210> SEQ ID NO 328
<211> LENGTH: 8
<212> TYPE: PRT
<213> ORGANISM: Artificial Sequence
<220> FEATURE:
<223> OTHER INFORMATION: Synthetic

<400> SEQUENCE: 328

Ala Arg Thr Glu Tyr Phe His His
1               5

<210> SEQ ID NO 329
<211> LENGTH: 321
<212> TYPE: DNA
<213> ORGANISM: Artificial Sequence
<220> FEATURE:
<223> OTHER INFORMATION: Synthetic

<400> SEQUENCE: 329

```
gacatccaga tgacccagtc tccatcctca ctgtctgcat ctgtaggaga cagaatcacc      60
atcacttgtc gggcgagtca ggacattaac aattatttag cctggtttca gcagaaacca     120
ggaaaagccc ctaagtccct gatctatggt gcatccagct tgcaaagtgg ggtcccatca     180
aagttcagcg gcagtggatc tgggacagat ttcactctca ccatcagcag cctgcagcct     240
gaagattttg caacttatta ctgccaacaa tatagttctt acccattcac tttcggccct     300
gggaccaaag tggatatcaa a                                                321
```

<210> SEQ ID NO 330
<211> LENGTH: 107
<212> TYPE: PRT
<213> ORGANISM: Artificial Sequence
<220> FEATURE:
<223> OTHER INFORMATION: Synthetic

<400> SEQUENCE: 330

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Gly Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Phe
                85                  90                  95

Thr Phe Gly Pro Gly Thr Lys Val Asp Ile Lys
            100                 105

<210> SEQ ID NO 331
<211> LENGTH: 18
<212> TYPE: DNA
<213> ORGANISM: Artificial Sequence
<220> FEATURE:
<223> OTHER INFORMATION: Synthetic

<400> SEQUENCE: 331
caggacatta acaattat                                                     18

<210> SEQ ID NO 332
<211> LENGTH: 6
<212> TYPE: PRT
<213> ORGANISM: Artificial Sequence
<220> FEATURE:
<223> OTHER INFORMATION: Synthetic

<400> SEQUENCE: 332

Gln Asp Ile Asn Asn Tyr
1               5

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333

```
ggtgcatcc                                                             9
```

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334

Gly Ala Ser
 1

<210> SEQ ID NO 335
<211> LENGTH: 27
<212> TYPE: DNA
<213> ORGANISM: Artificial Sequence
<220> FEATURE:
<223> OTHER INFORMATION: Synthetic

<400> SEQUENCE: 335

```
caacaatata gttcttaccc attcact                                        27
```

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

Gln Gln Tyr Ser Ser Tyr Pro Phe Thr
 1               5

<210> SEQ ID NO 337
<211> LENGTH: 348
<212> TYPE: DNA
<213> ORGANISM: Artificial Sequence
<220> FEATURE:
<223> OTHER INFORMATION: Synthetic

<400> SEQUENCE: 337

```
gaggtgcagc tggtggagtc tgggggaggc ttggtccagc ctggggggtc cctgagactc    60
tcctgtgcag cctctggatt catctttagt acctattgga tgaactgggt ccgccaggct   120
ccagggaagg ggctggagtg ggtggccaac gtgaaccatg atggaagtga ggaatactat   180
gtggactctg tgaagggccg attcaccatc tccagagaca acgccagaa ttcactgtat    240
ctgcaaatgg accgcctgag agccgaggac acggctatgt atttctgtgc gcgaagagcc   300
gggcttttg actcctgggg ccagggaacc ctggtcactg tctcctca                 348
```

<210> SEQ ID NO 338
<211> LENGTH: 116
<212> TYPE: PRT
<213> ORGANISM: Artificial Sequence
<220> FEATURE:
<223> OTHER INFORMATION: Synthetic

<400> SEQUENCE: 338

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ile Phe Ser Thr Tyr
            20                  25                  30

Trp Met Asn Trp Val Arg Gln Ala Pro Gly Lys Gly Leu Glu Trp Val

```
                35                  40                  45
Ala Asn Val Asn His Asp Gly Ser Glu Glu Tyr Tyr Val Asp Ser Val
         50                  55                  60

Lys Gly Arg Phe Thr Ile Ser Arg Asp Asn Ala Gln Asn Ser Leu Tyr
 65                  70                  75                  80

Leu Gln Met Asp Arg Leu Arg Ala Glu Asp Thr Ala Met Tyr Phe Cys
                 85                  90                  95

Ala Arg Arg Ala Gly Leu Phe Asp Ser Trp Gly Gln Gly Thr Leu Val
            100                 105                 110

Thr Val Ser Ser
        115

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggattcatct ttagtaccta ttgg                                          24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Phe Ile Phe Ser Thr Tyr Trp
 1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
gtgaaccatg atggaagtga ggaa                                          24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Val Asn His Asp Gly Ser Glu Glu
 1               5

<210> SEQ ID NO 343
<211> LENGTH: 27
<212> TYPE: DNA
<213> ORGANISM: Artificial Sequence
<220> FEATURE:
<223> OTHER INFORMATION: Synthetic

<400> SEQUENCE: 343
gcgcgaagag ccgggctttt tgactcc                                       27
```

```
<210> SEQ ID NO 344
<211> LENGTH: 9
<212> TYPE: PRT
<213> ORGANISM: Artificial Sequence
<220> FEATURE:
<223> OTHER INFORMATION: Synthetic

<400> SEQUENCE: 344

Ala Arg Arg Ala Gly Leu Phe Asp Ser
 1               5

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccatcttcc gtgtctgcat ctgtaggaga cagagtcacc    60
atcacttgtc gggcgagtca ggatattgac aactggttag cctggtatca gcagaaacca   120
gggaaagccc ctaaactcct gatctttact tcatccactt tgcaaagtgg ggtcccatca   180
aggttcagcg gcattggatc tggaacagat ttcactctca ccatcagcag cctacagcct   240
gaagattttg caacttacta ttgtcaacag gctaacagtt tcccgtggac gttcggccaa   300
gggaccaagg tggagatcaa a                                             321

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Asp Asn Trp
            20                  25                  30

Leu Ala Trp Tyr Gln Gln Lys Pro Gly Lys Ala Pro Lys Leu Leu Ile
        35                  40                  45

Phe Thr Ser Ser Thr Leu Gln Ser Gly Val Pro Ser Arg Phe Ser Gly
    50                  55                  60

Ile Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
caggatattg acaactgg                                                  18
```

```
<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Asp Ile Asp Asn Trp
 1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 acttcatcc                                                                  9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Thr Ser Ser
 1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacaggcta acagtttccc gtggacg                                             27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Ala Asn Ser Phe Pro Trp Thr
 1               5

<210> SEQ ID NO 353
<211> LENGTH: 375
<212> TYPE: DNA
<213> ORGANISM: Artificial Sequence
<220> FEATURE:
<223> OTHER INFORMATION: Synthetic

<400> SEQUENCE: 353
caggtgcagc tggtggagtc tgggggaggc gtggtcctgc ctggggaggtc cctgagactc          60 tcctgtgcag cgtctggatt caccttagt agttatctca tgtattgggt ccgccaggct          120
ccaggcaagg ggctgagtg gtggcagtt atatggtatg atggaagtaa taaattctat          180
ggagactccg tgaagggccg attcaccatc tccagagaca attccaagaa cacgttgtat          240
```

```
ctgcaaatga acagcctgag agccgaggac acggctgtgt attactgtgc gagagataat    300
gggaatagtg gttacgagga cagctggaat gcttttgata tatggggcca agggacaatg    360
gtcaccgtct cttca                                                     375
```

<210> SEQ ID NO 354
<211> LENGTH: 125
<212> TYPE: PRT
<213> ORGANISM: Artificial Sequence
<220> FEATURE:
<223> OTHER INFORMATION: Synthetic

<400> SEQUENCE: 354

```
Gln Val Gln Leu Val Glu Ser Gly Gly Gly Val Val Leu Pro Gly Arg
  1               5                  10                  15

Ser Leu Arg Leu Ser Cys Ala Ala Ser Gly Phe Thr Phe Ser Ser Tyr
             20                  25                  30

Leu Met Tyr Trp Val Arg Gln Ala Pro Gly Lys Gly Leu Glu Trp Val
         35                  40                  45

Ala Val Ile Trp Tyr Asp Gly Ser Asn Lys Phe Tyr Gly Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Asn Gly Asn Ser Gly Tyr Glu Asp Ser Trp Asn Ala Phe
            100                 105                 110

Asp Ile Trp Gly Gln Gly Thr Met Val Thr Val Ser Ser
        115                 120                 125
```

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355

```
ggattcacct ttagtagtta tctc                                            24
```

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

```
Gly Phe Thr Phe Ser Ser Tyr Leu
  1               5
```

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357

```
atatggtatg atggaagtaa taaa                                            24
```

-continued

```
<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

Ile Trp Tyr Asp Gly Ser Asn Lys
1               5

<210> SEQ ID NO 359
<211> LENGTH: 54
<212> TYPE: DNA
<213> ORGANISM: Artificial Sequence
<220> FEATURE:
<223> OTHER INFORMATION: Synthetic

<400> SEQUENCE: 359
gcgagagata atgggaatag tggttacgag gacagctgga atgcttttga tata          54

<210> SEQ ID NO 360
<211> LENGTH: 18
<212> TYPE: PRT
<213> ORGANISM: Artificial Sequence
<220> FEATURE:
<223> OTHER INFORMATION: Synthetic

<400> SEQUENCE: 360

Ala Arg Asp Asn Gly Asn Ser Gly Tyr Glu Asp Ser Trp Asn Ala Phe
1               5                   10                  15

Asp Ile

<210> SEQ ID NO 361
<211> LENGTH: 321
<212> TYPE: DNA
<213> ORGANISM: Artificial Sequence
<220> FEATURE:
<223> OTHER INFORMATION: Synthetic

<400> SEQUENCE: 361
gacatccaga tgacccagtc tccatcctca ctgtctgcat ctgtaggaga cagagtcacc    60
atcacttgtc gggcgagtca ggacatttac aattatttag cctggtttca gcagaaacca   120
gggaaagccc ctaagtccct gatctatgct gcatccagtt tgcaaactgg ggtcccatca   180
cagttcagcg gcagtggatc tgggacagat ttcactctca ccatcagcag cctccagcct   240
gaagattttg caacttatta ctgccaacag tataataatt acccattcac tttcggccct   300
gggaccaaag tggatatcaa a                                             321

<210> SEQ ID NO 362
<211> LENGTH: 107
<212> TYPE: PRT
<213> ORGANISM: Artificial Sequence
<220> FEATURE:
<223> OTHER INFORMATION: Synthetic

<400> SEQUENCE: 362

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Tyr Asn Tyr
                20                  25                  30

Leu Ala Trp Phe Gln Gln Lys Pro Gly Lys Ala Pro Lys Ser Leu Ile
            35                  40                  45
```

```
Tyr Ala Ala Ser Ser Leu Gln Thr Gly Val Pro Ser Gln Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Phe
                 85                  90                  95

Thr Phe Gly Pro Gly Thr Lys Val Asp Ile Lys
            100                 105
```

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363
caggacattt acaattat                                                18

<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364

```
Gln Asp Ile Tyr Asn Tyr
 1               5
```

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 gctgcatcc                                                           9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

```
Ala Ala Ser
 1
```

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
caacagtata ataattaccc attcact                                      27

<210> SEQ ID NO 368
<211> LENGTH: 9
<212> TYPE: PRT

```
<213> ORGANISM: Artificial Sequence
<220> FEATURE:
<223> OTHER INFORMATION: Synthetic

<400> SEQUENCE: 368

Gln Gln Tyr Asn Asn Tyr Pro Phe Thr
 1               5

<210> SEQ ID NO 369
<211> LENGTH: 360
<212> TYPE: DNA
<213> ORGANISM: Artificial Sequence
<220> FEATURE:
<223> OTHER INFORMATION: Synthetic

<400> SEQUENCE: 369
gaggtgcagc tggtggagtc tgggggaggc ttggcacagc ctggggggtc cctgagactc      60
tcctgtgcag cctctggatt cacctttaac aactatgcca tgacctgggt ccgccaggct     120
ccagggaagg gtctggactg ggtctcagct attagtgata gtggtcgtag cacattctcc     180
gcagactccg tgaagggccg gttcaccatc tccagagaca actccaagaa cacgctgtat     240
ctgcaaatgg acagcctgag agccgaggac acggccttat attactgtgc gaaacatagg     300
aactggaact atcccgtctt tgactactgg ggccaggaa ccctggtcac cgtctcctca      360

<210> SEQ ID NO 370
<211> LENGTH: 120
<212> TYPE: PRT
<213> ORGANISM: Artificial Sequence
<220> FEATURE:
<223> OTHER INFORMATION: Synthetic

<400> SEQUENCE: 370

Glu Val Gln Leu Val Glu Ser Gly Gly Gly Leu Ala Gln Pro Gly Gly
 1               5                  10                  15

Ser Leu Arg Leu Ser Cys Ala Ala Ser Gly Phe Thr Phe Asn Asn Tyr
             20                  25                  30

Ala Met Thr Trp Val Arg Gln Ala Pro Gly Lys Gly Leu Asp Trp Val
         35                  40                  45

Ser Ala Ile Ser Asp Ser Gly Arg Ser Thr Phe Ser Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Leu Tyr Tyr Cys
                 85                  90                  95

Ala Lys His Arg Asn Trp Asn Tyr Pro Val Phe Asp Tyr Trp Gly Gln
            100                 105                 110

Gly Thr Leu Val Thr Val Ser Ser
        115                 120

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
ggattcacct ttaacaacta tgcc                                             24

<210> SEQ ID NO 372
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 372

Gly Phe Thr Phe Asn Asn Tyr Ala
 1               5

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
attagtgata gtggtcgtag caca                                              24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Ile Ser Asp Ser Gly Arg Ser Thr
 1               5

<210> SEQ ID NO 375
<211> LENGTH: 39
<212> TYPE: DNA
<213> ORGANISM: Artificial Sequence
<220> FEATURE:
<223> OTHER INFORMATION: Synthetic

<400> SEQUENCE: 375
gcgaaacata ggaactggaa ctatcccgtc tttgactac                              39

<210> SEQ ID NO 376
<211> LENGTH: 13
<212> TYPE: PRT
<213> ORGANISM: Artificial Sequence
<220> FEATURE:
<223> OTHER INFORMATION: Synthetic

<400> SEQUENCE: 376

Ala Lys His Arg Asn Trp Asn Tyr Pro Val Phe Asp Tyr
 1               5                   10

<210> SEQ ID NO 377
<211> LENGTH: 321
<212> TYPE: DNA
<213> ORGANISM: Artificial Sequence
<220> FEATURE:
<223> OTHER INFORMATION: Synthetic

<400> SEQUENCE: 377
gacatccagt tgacccagtc tccatccttc ctgtctgcat ctgtgggaga cagagtcacc       60
atcacttgct gggccagtca gggcattagt agttatttag cctggtatca gcaaaaacca      120
gggaaagccc caagctcct gatctattct gcatccactt tacaaagtgg ggtcccatca       180
aggttcagcg gcagtggatc tgggacagaa ttcactctca caatcagcag cctgcagcct      240
```

```
gaagattttg caacttatta ctgtcaacaa cttaatagtt acccattcac tttcggccct    300
gggaccaaag tggatatcaa a                                              321
```

<210> SEQ ID NO 378
<211> LENGTH: 107
<212> TYPE: PRT
<213> ORGANISM: Artificial Sequence
<220> FEATURE:
<223> OTHER INFORMATION: Synthetic

<400> SEQUENCE: 378

```
Asp Ile Gln Leu Thr Gln Ser Pro Ser Phe Leu Ser Ala Ser Val Gly
  1               5                  10                  15

Asp Arg Val Thr Ile Thr Cys Trp Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ser Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Phe
                 85                  90                  95

Thr Phe Gly Pro Gly Thr Lys Val Asp Ile Lys
            100                 105
```

<210> SEQ ID NO 379
<211> LENGTH: 18
<212> TYPE: DNA
<213> ORGANISM: Artificial Sequence
<220> FEATURE:
<223> OTHER INFORMATION: Synthetic

<400> SEQUENCE: 379

```
cagggcatta gtagttat                                                   18
```

<210> SEQ ID NO 380
<211> LENGTH: 6
<212> TYPE: PRT
<213> ORGANISM: Artificial Sequence
<220> FEATURE:
<223> OTHER INFORMATION: Synthetic

<400> SEQUENCE: 380

```
Gln Gly Ile Ser Ser Tyr
  1               5
```

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381

```
tctgcatcc                                                              9
```

<210> SEQ ID NO 382
<211> LENGTH: 3
<212> TYPE: PRT
<213> ORGANISM: Artificial Sequence
<220> FEATURE:
<223> OTHER INFORMATION: Synthetic

<400> SEQUENCE: 382

Ser Ala Ser
 1

<210> SEQ ID NO 383
<211> LENGTH: 27
<212> TYPE: DNA
<213> ORGANISM: Artificial Sequence
<220> FEATURE:
<223> OTHER INFORMATION: Synthetic

<400> SEQUENCE: 383
caacaactta atagttaccc attcact              27

<210> SEQ ID NO 384
<211> LENGTH: 9
<212> TYPE: PRT
<213> ORGANISM: Artificial Sequence
<220> FEATURE:
<223> OTHER INFORMATION: Synthetic

<400> SEQUENCE: 384

Gln Gln Leu Asn Ser Tyr Pro Phe Thr
 1               5

<210> SEQ ID NO 385
<211> LENGTH: 190
<212> TYPE: PRT
<213> ORGANISM: Artificial Sequence
<220> FEATURE:
<223> OTHER INFORMATION: Synthetic

<400> SEQUENCE: 385

Val Lys Met Ala Glu Thr Cys Pro Ile Phe Tyr Asp Val Phe Phe Ala
 1               5                  10                  15

Val Ala Asn Gly Asn Glu Leu Leu Leu Asp Leu Ser Leu Thr Lys Val
             20                  25                  30

Asn Ala Thr Glu Pro Glu Arg Thr Ala Met Lys Lys Ile Gln Asp Cys
         35                  40                  45

Tyr Val Glu Asn Gly Leu Ile Ser Arg Val Leu Asp Gly Leu Val Met
     50                  55                  60

Thr Thr Ile Ser Ser Lys Asp Cys Met Gly Glu Ala Val Gln Asn
 65                  70                  75                  80

Thr Val Glu Asp Leu Lys Leu Asn Thr Leu Gly Arg Glu Ile Cys Pro
                 85                  90                  95

Ala Val Lys Arg Asp Val Asp Leu Phe Leu Thr Gly Thr Pro Asp Glu
            100                 105                 110

Tyr Val Glu Gln Val Ala Gln Tyr Lys Ala Leu Pro Val Val Leu Glu
        115                 120                 125

Asn Ala Arg Ile Leu Lys Asn Cys Val Asp Ala Lys Met Thr Glu Glu
    130                 135                 140

Asp Lys Glu Asn Ala Leu Ser Val Leu Asp Lys Ile Tyr Thr Ser Pro
145                 150                 155                 160

Leu Cys Glu Gln Lys Leu Ile Glu Glu Asp Leu Gly Gly Glu Gln
                165                 170                 175

Lys Leu Ile Ser Glu Glu Asp Leu His His His His His
            180                 185                 190

<210> SEQ ID NO 386

```
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe, Tyr or Gly
<220> FEATURE:
<221> NAME/KEY: VARIANT
<222> LOCATION: (3)...(3)
<223> OTHER INFORMATION: Xaa = Thr or Ser
<220> FEATURE:
<221> NAME/KEY: VARIANT
<222> LOCATION: (4)...(4)
<223> OTHER INFORMATION: Xaa = Phe or Ile
<220> FEATURE:
<221> NAME/KEY: VARIANT
<222> LOCATION: (5)...(5)
<223> OTHER INFORMATION: Xaa = Ser, Arg, Thr, or Asn
<220> FEATURE:
<221> NAME/KEY: VARIANT
<222> LOCATION: (6)...(6)
<223> OTHER INFORMATION: Xaa = Asn, Thr, Asp, or Ser
<220> FEATURE:
<221> NAME/KEY: VARIANT
<222> LOCATION: (7)...(7)
<223> OTHER INFORMATION: Xaa = Tyr
<220> FEATURE:
<221> NAME/KEY: VARIANT
<222> LOCATION: (8)...(8)
<223> OTHER INFORMATION: Xaa = Asn, Tyr, or Ala

<400> SEQUENCE: 386

Xaa Xaa Xaa Xaa Xaa Xaa Xaa Xaa
 1               5

<210> SEQ ID NO 387
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile
<220> FEATURE:
<221> NAME/KEY: VARIANT
<222> LOCATION: (2)...(2)
<223> OTHER INFORMATION: Xaa = Tyr, Ser, or Asn
<220> FEATURE:
<221> NAME/KEY: VARIANT
<222> LOCATION: (3)...(3)
<223> OTHER INFORMATION: Xaa = Tyr, Ser, Gly, Pro, or Asp
<220> FEATURE:
<221> NAME/KEY: VARIANT
<222> LOCATION: (4)...(4)
<223> OTHER INFORMATION: Xaa = Asp, Arg, or Ser
<220> FEATURE:
<221> NAME/KEY: VARIANT
<222> LOCATION: (5)...(5)
<223> OTHER INFORMATION: Xaa = Gly, Val, or Ser
<220> FEATURE:
<221> NAME/KEY: VARIANT
<222> LOCATION: (6)...(6)
<223> OTHER INFORMATION: Xaa = Ser, Gly, Arg, or Tyr
<220> FEATURE:
<221> NAME/KEY: VARIANT
<222> LOCATION: (7)...(7)
<223> OTHER INFORMATION: Xaa = Tyr, Arg, Thr, Ser, or Asn
<220> FEATURE:
```

<221> NAME/KEY: VARIANT
<222> LOCATION: (8)...(8)
<223> OTHER INFORMATION: Xaa = Ile, Thr, Ala, Ser, or absent

<400> SEQUENCE: 387

Xaa Xaa Xaa Xaa Xaa Xaa Xaa Xaa
 1               5

<210> SEQ ID NO 388
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala
<220> FEATURE:
<221> NAME/KEY: VARIANT
<222> LOCATION: (2)...(2)
<223> OTHER INFORMATION: Xaa = Lys or Arg
<220> FEATURE:
<221> NAME/KEY: VARIANT
<222> LOCATION: (3)...(3)
<223> OTHER INFORMATION: Xaa = Arg, Gly, His, Ser, Asp, Leu, or Thr
<220> FEATURE:
<221> NAME/KEY: VARIANT
<222> LOCATION: (4)...(4)
<223> OTHER INFORMATION: Xaa = Thr, Pro, Arg, Gly, or Glu
<220> FEATURE:
<221> NAME/KEY: VARIANT
<222> LOCATION: (5)...(5)
<223> OTHER INFORMATION: Xaa = Leu, Val, Gly, Lys, Tyr, or Asn
<220> FEATURE:
<221> NAME/KEY: VARIANT
<222> LOCATION: (6)...(6)
<223> OTHER INFORMATION: Xaa = Ser, Arg, Thr, Ala, Tyr, Phe, or Trp
<220> FEATURE:
<221> NAME/KEY: VARIANT
<222> LOCATION: (7)...(7)
<223> OTHER INFORMATION: Xaa = Tyr, Gly, Arg, Ala, Asn, Asp, His, or Asn
<220> FEATURE:
<221> NAME/KEY: VARIANT
<222> LOCATION: (8)...(8)
<223> OTHER INFORMATION: Xaa = Tyr, Thr, Ser, or His
<220> FEATURE:
<221> NAME/KEY: VARIANT
<222> LOCATION: (9)...(9)
<223> OTHER INFORMATION: Xaa = Val, Ser, Ala, Phe, Pro, or absent
<220> FEATURE:
<221> NAME/KEY: VARIANT
<222> LOCATION: (10)...(10)
<223> OTHER INFORMATION: Xaa = Met, Gly, Asp, Pro, Val, or absent
<220> FEATURE:
<221> NAME/KEY: VARIANT
<222> LOCATION: (11)...(11)
<223> OTHER INFORMATION: Xaa = Asp, Tyr, Ser, Gly, Phe, or absent
<220> FEATURE:
<221> NAME/KEY: VARIANT
<222> LOCATION: (12)...(12)
<223> OTHER INFORMATION: Xaa = Val, Asp, Phe, or absent
<220> FEATURE:
<221> NAME/KEY: VARIANT
<222> LOCATION: (13)...(13)
<223> OTHER INFORMATION: Xaa = Phe, Asp, or absent
<220> FEATURE:
<221> NAME/KEY: VARIANT
<222> LOCATION: (14)...(14)
<223> OTHER INFORMATION: Xaa = Phe, Tyr, or absent
<220> FEATURE:
<221> NAME/KEY: VARIANT
<222> LOCATION: (15)...(15)
<223> OTHER INFORMATION: Xaa = Asp or absent
<220> FEATURE:
<221> NAME/KEY: VARIANT
<222> LOCATION: (16)...(16)

```
<223> OTHER INFORMATION: Xaa = Tyr or absent

<400> SEQUENCE: 388

Xaa Xaa Xaa Xaa Xaa Xaa Xaa Xaa Xaa Xaa Xaa Xaa Xaa Xaa Xaa Xaa
1               5                   10                  15

<210> SEQ ID NO 389
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Gly, Ser, or Asp
<220> FEATURE:
<221> NAME/KEY: VARIANT
<222> LOCATION: (3)...(3)
<223> OTHER INFORMATION: Xaa = Ile or Val
<220> FEATURE:
<221> NAME/KEY: VARIANT
<222> LOCATION: (4)...(4)
<223> OTHER INFORMATION: Xaa = Ser, Leu, Asn, or Gly
<220> FEATURE:
<221> NAME/KEY: VARIANT
<222> LOCATION: (5)...(5)
<223> OTHER INFORMATION: Xaa = Asn, Tyr, Gly, or Ser
<220> FEATURE:
<221> NAME/KEY: VARIANT
<222> LOCATION: (6)...(6)
<223> OTHER INFORMATION: Xaa = Tyr, Ser, Phe, or Trp
<220> FEATURE:
<221> NAME/KEY: VARIANT
<222> LOCATION: (7)...(7)
<223> OTHER INFORMATION: Xaa = Ser or absent
<220> FEATURE:
<221> NAME/KEY: VARIANT
<222> LOCATION: (8)...(8)
<223> OTHER INFORMATION: Xaa = Asn or absent
<220> FEATURE:
<221> NAME/KEY: VARIANT
<222> LOCATION: (9)...(9)
<223> OTHER INFORMATION: Xaa = Asn or absent
<220> FEATURE:
<221> NAME/KEY: VARIANT
<222> LOCATION: (10)...(10)
<223> OTHER INFORMATION: Xaa = Lys or absent
<220> FEATURE:
<221> NAME/KEY: VARIANT
<222> LOCATION: (11)...(11)
<223> OTHER INFORMATION: Xaa = Gln or absent
<220> FEATURE:
<221> NAME/KEY: VARIANT
<222> LOCATION: (12)...(12)
<223> OTHER INFORMATION: Xaa = Tyr or absent

<400> SEQUENCE: 389

Xaa Xaa Xaa Xaa Xaa Xaa Xaa Xaa Xaa Xaa Xaa Xaa
1               5                   10

<210> SEQ ID NO 390
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala, Trp, Asp, Tyr, Lys, Gly, or Ser
```

```
<220> FEATURE:
<221> NAME/KEY: VARIANT
<222> LOCATION: (2)...(2)
<223> OTHER INFORMATION: Xaa = Ala or Thr
<220> FEATURE:
<221> NAME/KEY: VARIANT
<222> LOCATION: (3)...(3)
<223> OTHER INFORMATION: Xaa = Ser

<400> SEQUENCE: 390

Xaa Xaa Xaa
 1

<210> SEQ ID NO 391
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln, Leu, or His
<220> FEATURE:
<221> NAME/KEY: VARIANT
<222> LOCATION: (2)...(2)
<223> OTHER INFORMATION: Xaa = Lys, Gln, or His
<220> FEATURE:
<221> NAME/KEY: VARIANT
<222> LOCATION: (3)...(3)
<223> OTHER INFORMATION: Xaa = Tyr, Ser, or Leu
<220> FEATURE:
<221> NAME/KEY: VARIANT
<222> LOCATION: (4)...(4)
<223> OTHER INFORMATION: Xaa = Tyr, Asn, Gly, Asp, or Ser
<220> FEATURE:
<221> NAME/KEY: VARIANT
<222> LOCATION: (5)...(5)
<223> OTHER INFORMATION: Xaa = Ser, Asp, or Asn
<220> FEATURE:
<221> NAME/KEY: VARIANT
<222> LOCATION: (6)...(6)
<223> OTHER INFORMATION: Xaa = Leu, Ala, Tyr, Thr, or Phe
<220> FEATURE:
<221> NAME/KEY: VARIANT
<222> LOCATION: (7)...(7)
<223> OTHER INFORMATION: Xaa = Pro or Arg
<220> FEATURE:
<221> NAME/KEY: VARIANT
<222> LOCATION: (8)...(8)
<223> OTHER INFORMATION: Xaa = Leu, Phe, Tyr, or Thr
<220> FEATURE:
<221> NAME/KEY: VARIANT
<222> LOCATION: (9)...(9)
<223> OTHER INFORMATION: Xaa = Thr or absent

<400> SEQUENCE: 391

Xaa Xaa Xaa Xaa Xaa Xaa Xaa Xaa Xaa
 1               5

<210> SEQ ID NO 392
<211> LENGTH: 70
<212> TYPE: PRT
<213> ORGANISM: Artificial Sequence
<220> FEATURE:
<223> OTHER INFORMATION: Synthetic

<400> SEQUENCE: 392

Glu Ile Cys Pro Ala Val Lys Arg Asp Val Asp Leu Phe Leu Thr Gly
 1               5                  10                  15

Thr Pro Asp Glu Tyr Val Glu Gln Val Ala Gln Tyr Lys Ala Leu Pro
             20                  25                  30
```

```
Val Val Leu Glu Asn Ala Arg Ile Leu Lys Asn Cys Val Asp Ala Lys
         35                  40                  45

Met Thr Glu Glu Asp Lys Glu Asn Ala Leu Ser Leu Leu Asp Lys Ile
 50                  55                  60

Tyr Thr Ser Pro Leu Cys
 65                  70
```

<210> SEQ ID NO 393
<211> LENGTH: 92
<212> TYPE: PRT
<213> ORGANISM: Artificial Sequence
<220> FEATURE:
<223> OTHER INFORMATION: Synthetic

<400> SEQUENCE: 393

```
Val Lys Met Ala Glu Thr Cys Pro Ile Phe Tyr Asp Val Phe Phe Ala
 1               5                  10                  15

Val Ala Asn Gly Asn Glu Leu Leu Asp Leu Ser Leu Thr Lys Val
             20                  25                  30

Asn Ala Thr Glu Pro Glu Arg Thr Ala Met Lys Lys Ile Gln Asp Cys
         35                  40                  45

Tyr Val Glu Asn Gly Leu Ile Ser Arg Val Leu Asp Gly Leu Val Met
 50                  55                  60

Thr Thr Ile Ser Ser Lys Asp Cys Met Gly Glu Ala Val Gln Asn
 65                  70                  75                  80

Thr Val Glu Asp Leu Lys Leu Asn Thr Leu Gly Arg
                 85                  90
```

<210> SEQ ID NO 394
<211> LENGTH: 398
<212> TYPE: PRT
<213> ORGANISM: Artificial Sequence
<220> FEATURE:
<223> OTHER INFORMATION: Synthetic

<400> SEQUENCE: 394

```
Val Lys Met Ala Glu Thr Cys Pro Ile Phe Tyr Asp Val Phe Phe Ala
 1               5                  10                  15

Val Ala Asn Gly Asn Glu Leu Leu Leu Asp Leu Ser Leu Thr Lys Val
             20                  25                  30

Asn Ala Thr Glu Pro Glu Arg Thr Ala Met Lys Lys Ile Gln Asp Cys
         35                  40                  45

Tyr Val Glu Asn Gly Leu Ile Ser Arg Val Leu Asp Gly Leu Val Met
 50                  55                  60

Thr Thr Ile Ser Ser Lys Asp Cys Met Gly Glu Ala Val Gln Asn
 65                  70                  75                  80

Thr Val Glu Asp Leu Lys Leu Asn Thr Leu Gly Arg Glu Ile Cys Pro
                 85                  90                  95

Ala Val Lys Arg Asp Val Asp Leu Phe Leu Thr Gly Thr Pro Asp Glu
                100                 105                 110

Tyr Val Glu Gln Val Ala Gln Tyr Lys Ala Leu Pro Val Val Leu Glu
            115                 120                 125

Asn Ala Arg Ile Leu Lys Asn Cys Val Asp Ala Lys Met Thr Glu Glu
        130                 135                 140

Asp Lys Glu Asn Ala Leu Ser Leu Leu Asp Lys Ile Tyr Thr Ser Pro
145                 150                 155                 160

Leu Cys Leu Ile Asn Glu Pro Arg Gly Pro Thr Ile Lys Pro Cys Pro
                165                 170                 175
```

```
Pro Cys Lys Cys Pro Ala Pro Asn Leu Leu Gly Gly Pro Ser Val Phe
            180                 185                 190

Ile Phe Pro Pro Lys Ile Lys Asp Val Leu Met Ile Ser Leu Ser Pro
        195                 200                 205

Ile Val Thr Cys Val Val Val Asp Val Ser Glu Asp Pro Asp Val
    210                 215                 220

Gln Ile Ser Trp Phe Val Asn Asn Val Glu Val His Thr Ala Gln Thr
225                 230                 235                 240

Gln Thr His Arg Glu Asp Tyr Asn Ser Thr Leu Arg Val Val Ser Ala
                245                 250                 255

Leu Pro Ile Gln His Gln Asp Trp Met Ser Gly Lys Glu Phe Lys Cys
            260                 265                 270

Lys Val Asn Asn Lys Asp Leu Pro Ala Pro Ile Glu Arg Thr Ile Ser
        275                 280                 285

Lys Pro Lys Gly Ser Val Arg Ala Pro Gln Val Tyr Val Leu Pro Pro
    290                 295                 300

Pro Glu Glu Glu Met Thr Lys Lys Gln Val Thr Leu Thr Cys Met Val
305                 310                 315                 320

Thr Asp Phe Met Pro Glu Asp Ile Tyr Val Glu Trp Thr Asn Asn Gly
                325                 330                 335

Lys Thr Glu Leu Asn Tyr Lys Asn Thr Glu Pro Val Leu Asp Ser Asp
            340                 345                 350

Gly Ser Tyr Phe Met Tyr Ser Lys Leu Arg Val Glu Lys Lys Asn Trp
        355                 360                 365

Val Glu Arg Asn Ser Tyr Ser Cys Ser Val Val His Glu Gly Leu His
    370                 375                 380

Asn His His Thr Thr Lys Ser Phe Ser Arg Thr Pro Gly Lys
385                 390                 395

<210> SEQ ID NO 395
<211> LENGTH: 413
<212> TYPE: PRT
<213> ORGANISM: Artificial Sequence
<220> FEATURE:
<223> OTHER INFORMATION: Synthetic

<400> SEQUENCE: 395

Glu Ile Cys Pro Ala Val Lys Arg Asp Val Asp Leu Phe Leu Thr Gly
  1               5                  10                  15

Thr Pro Asp Glu Tyr Val Glu Gln Val Ala Gln Tyr Lys Ala Leu Pro
             20                  25                  30

Val Val Leu Glu Asn Ala Arg Ile Leu Lys Asn Cys Val Asp Ala Lys
         35                  40                  45

Met Thr Glu Glu Asp Lys Glu Asn Ala Leu Ser Leu Leu Asp Lys Ile
     50                  55                  60

Tyr Thr Ser Pro Leu Cys Gly Gly Gly Ser Gly Gly Gly Gly Ser
 65                  70                  75                  80

Gly Gly Gly Gly Ser Val Lys Met Ala Glu Thr Cys Pro Ile Phe Tyr
                 85                  90                  95

Asp Val Phe Phe Ala Val Ala Asn Gly Asn Glu Leu Leu Leu Asp Leu
            100                 105                 110

Ser Leu Thr Lys Val Asn Ala Thr Glu Pro Glu Arg Thr Ala Met Lys
        115                 120                 125

Lys Ile Gln Asp Cys Tyr Val Glu Asn Gly Leu Ile Ser Arg Val Leu
    130                 135                 140
```

Asp Gly Leu Val Met Thr Thr Ile Ser Ser Lys Asp Cys Met Gly
145                 150                 155                 160

Glu Ala Val Gln Asn Thr Val Glu Asp Leu Lys Leu Asn Thr Leu Gly
                165                 170                 175

Arg Leu Ile Asn Glu Pro Arg Gly Pro Thr Ile Lys Pro Cys Pro Pro
            180                 185                 190

Cys Lys Cys Pro Ala Pro Asn Leu Leu Gly Gly Pro Ser Val Phe Ile
        195                 200                 205

Phe Pro Pro Lys Ile Lys Asp Val Leu Met Ile Ser Leu Ser Pro Ile
    210                 215                 220

Val Thr Cys Val Val Asp Val Ser Glu Asp Pro Asp Val Gln
225                 230                 235                 240

Ile Ser Trp Phe Val Asn Asn Val Glu Val His Thr Ala Gln Thr Gln
                245                 250                 255

Thr His Arg Glu Asp Tyr Asn Ser Thr Leu Arg Val Val Ser Ala Leu
            260                 265                 270

Pro Ile Gln His Gln Asp Trp Met Ser Gly Lys Glu Phe Lys Cys Lys
        275                 280                 285

Val Asn Asn Lys Asp Leu Pro Ala Pro Ile Glu Arg Thr Ile Ser Lys
    290                 295                 300

Pro Lys Gly Ser Val Arg Ala Pro Gln Val Tyr Val Leu Pro Pro Pro
305                 310                 315                 320

Glu Glu Glu Met Thr Lys Lys Gln Val Thr Leu Thr Cys Met Val Thr
                325                 330                 335

Asp Phe Met Pro Glu Asp Ile Tyr Val Glu Trp Thr Asn Asn Gly Lys
            340                 345                 350

Thr Glu Leu Asn Tyr Lys Asn Thr Glu Pro Val Leu Asp Ser Asp Gly
        355                 360                 365

Ser Tyr Phe Met Tyr Ser Lys Leu Arg Val Glu Lys Lys Asn Trp Val
    370                 375                 380

Glu Arg Asn Ser Tyr Ser Cys Ser Val Val His Glu Gly Leu His Asn
385                 390                 395                 400

His His Thr Thr Lys Ser Phe Ser Arg Thr Pro Gly Lys
                405                 410

<210> SEQ ID NO 396
<211> LENGTH: 199
<212> TYPE: PRT
<213> ORGANISM: Artificial Sequence
<220> FEATURE:
<223> OTHER INFORMATION: Synthetic

<400> SEQUENCE: 396

Val Lys Met Ala Glu Thr Cys Pro Ile Phe Tyr Asp Val Phe Phe Ala
 1               5                  10                  15

Val Ala Asn Gly Asn Glu Leu Leu Leu Asp Leu Ser Leu Thr Lys Val
                20                  25                  30

Asn Ala Thr Glu Pro Glu Arg Thr Ala Met Lys Lys Ile Gln Asp Cys
            35                  40                  45

Tyr Val Glu Asn Gly Leu Ile Ser Arg Val Leu Asp Gly Leu Val Met
        50                  55                  60

Thr Thr Ile Ser Ser Ser Lys Asp Cys Met Gly Glu Ala Val Gln Asn
65                  70                  75                  80

Thr Val Glu Asp Leu Lys Leu Asn Thr Leu Gly Arg Glu Ile Cys Pro
                85                  90                  95

Ala Val Lys Arg Gly Val Asp Leu Phe Leu Thr Gly Thr Pro Asp Glu
            100                 105                 110

Tyr Val Glu Gln Val Ala Gln Tyr Lys Ala Leu Pro Val Val Leu Glu
            115                 120                 125

Asn Ala Arg Ile Leu Lys Asn Cys Val Asp Ala Lys Met Thr Glu Glu
            130                 135                 140

Asp Lys Glu Asn Ala Leu Ser Leu Leu Asp Lys Ile Tyr Thr Ser Pro
145                 150                 155                 160

Leu Cys Gly Pro Gly Gly Gln Lys Leu Ile Ser Glu Glu Asp Leu
            165                 170                 175

Gly Gly Glu Gln Lys Leu Ile Ser Glu Glu Asp Leu Ser Gly His His
            180                 185                 190

His His His His Ser Ser Gly
            195

<210> SEQ ID NO 397
<211> LENGTH: 214
<212> TYPE: PRT
<213> ORGANISM: Artificial Sequence
<220> FEATURE:
<223> OTHER INFORMATION: Synthetic

<400> SEQUENCE: 397

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Leu Glu Asn Ala Arg Ile Leu Lys Asn Cys Val Asp Ala Lys
            35                  40                  45

Met Thr Glu Glu Asp Lys Glu Asn Ala Leu Ser Leu Leu Asp Lys Ile
        50                  55                  60

Tyr Thr Ser Pro Leu Cys Gly Gly Gly Ser Gly Gly Gly Ser
65                  70                  75                  80

Gly Gly Gly Gly Ser Val Lys Met Ala Glu Thr Cys Pro Ile Phe Tyr
            85                  90                  95

Asp Val Phe Phe Ala Val Ala Asn Gly Asn Glu Leu Leu Leu Asp Leu
            100                 105                 110

Ser Leu Thr Lys Val Asn Ala Thr Glu Pro Glu Arg Thr Ala Met Lys
            115                 120                 125

Lys Ile Gln Asp Cys Tyr Val Glu Asn Gly Leu Ile Ser Arg Val Leu
        130                 135                 140

Asp Gly Leu Val Met Thr Thr Ile Ser Ser Lys Asp Cys Met Gly
145                 150                 155                 160

Glu Ala Val Gln Asn Thr Val Glu Asp Leu Lys Leu Asn Thr Leu Gly
            165                 170                 175

Arg Gly Pro Gly Gly Glu Gln Lys Leu Ile Ser Glu Glu Asp Leu Gly
            180                 185                 190

Gly Glu Gln Lys Leu Ile Ser Glu Glu Asp Leu Ser Gly His His His
            195                 200                 205

His His His Ser Ser Gly
        210

<210> SEQ ID NO 398
<211> LENGTH: 11
<212> TYPE: PRT
<213> ORGANISM: Artificial Sequence

```
<220> FEATURE:
<223> OTHER INFORMATION: Synthetic

<400> SEQUENCE: 398

Val Lys Met Ala Glu Thr Cys Pro Ile Phe Tyr
1               5                   10

<210> SEQ ID NO 399
<211> LENGTH: 7
<212> TYPE: PRT
<213> ORGANISM: Artificial Sequence
<220> FEATURE:
<223> OTHER INFORMATION: Synthetic

<400> SEQUENCE: 399

Ile Ser Arg Val Leu Asp Gly
1               5

<210> SEQ ID NO 400
<211> LENGTH: 8
<212> TYPE: PRT
<213> ORGANISM: Artificial Sequence
<220> FEATURE:
<223> OTHER INFORMATION: Synthetic

<400> SEQUENCE: 400

Ile Ser Arg Val Leu Asp Gly Leu
1               5

<210> SEQ ID NO 401
<211> LENGTH: 10
<212> TYPE: PRT
<213> ORGANISM: Artificial Sequence
<220> FEATURE:
<223> OTHER INFORMATION: Synthetic

<400> SEQUENCE: 401

Ile Ser Arg Val Leu Asp Gly Leu Val Met
1               5                   10

<210> SEQ ID NO 402
<211> LENGTH: 19
<212> TYPE: PRT
<213> ORGANISM: Artificial Sequence
<220> FEATURE:
<223> OTHER INFORMATION: Synthetic

<400> SEQUENCE: 402

Leu Lys Leu Asn Thr Leu Gly Arg Glu Ile Cys Pro Ala Val Lys Arg
1               5                   10                  15

Gly Val Asp

<210> SEQ ID NO 403
<211> LENGTH: 20
<212> TYPE: PRT
<213> ORGANISM: Artificial Sequence
<220> FEATURE:
<223> OTHER INFORMATION: Synthetic

<400> SEQUENCE: 403

Leu Lys Leu Asn Thr Leu Gly Arg Glu Ile Cys Pro Ala Val Lys Arg
1               5                   10                  15

Gly Val Asp Leu
            20
```

```
<210> SEQ ID NO 404
<211> LENGTH: 15
<212> TYPE: PRT
<213> ORGANISM: Artificial Sequence
<220> FEATURE:
<223> OTHER INFORMATION: Synthetic

<400> SEQUENCE: 404

Tyr Val Glu Gln Val Ala Gln Tyr Lys Ala Leu Pro Val Val Leu
1               5                   10                  15

<210> SEQ ID NO 405
<211> LENGTH: 11
<212> TYPE: PRT
<213> ORGANISM: Artificial Sequence
<220> FEATURE:
<223> OTHER INFORMATION: Synthetic

<400> SEQUENCE: 405

Val Ala Gln Tyr Lys Ala Leu Pro Val Val Leu
1               5                   10

<210> SEQ ID NO 406
<211> LENGTH: 14
<212> TYPE: PRT
<213> ORGANISM: Artificial Sequence
<220> FEATURE:
<223> OTHER INFORMATION: Synthetic

<400> SEQUENCE: 406

Glu Asn Ala Arg Ile Leu Lys Asn Cys Val Asp Ala Lys Met
1               5                   10

<210> SEQ ID NO 407
<211> LENGTH: 18
<212> TYPE: PRT
<213> ORGANISM: Artificial Sequence
<220> FEATURE:
<223> OTHER INFORMATION: Synthetic

<400> SEQUENCE: 407

Leu Asp Lys Ile Tyr Thr Ser Pro Leu Cys Gly Pro Gly Gly Glu Gln
1               5                   10                  15

Lys Leu

<210> SEQ ID NO 408
<211> LENGTH: 14
<212> TYPE: PRT
<213> ORGANISM: Artificial Sequence
<220> FEATURE:
<223> OTHER INFORMATION: Synthetic

<400> SEQUENCE: 408

Ile Ser Glu Glu Asp Leu Ser Gly His His His His His His
1               5                   10

<210> SEQ ID NO 409
<211> LENGTH: 17
<212> TYPE: PRT
<213> ORGANISM: Artificial Sequence
<220> FEATURE:
<223> OTHER INFORMATION: Synthetic

<400> SEQUENCE: 409

Ile Ser Glu Glu Asp Leu Ser Gly His His His His His His Ser Ser
1               5                   10                  15
```

```
Gly

<210> SEQ ID NO 410
<211> LENGTH: 14
<212> TYPE: PRT
<213> ORGANISM: Artificial Sequence
<220> FEATURE:
<223> OTHER INFORMATION: Synthetic

<400> SEQUENCE: 410

Glu Asp Leu Ser Gly His His His His His His Ser Ser Gly
 1               5                  10

<210> SEQ ID NO 411
<211> LENGTH: 11
<212> TYPE: PRT
<213> ORGANISM: Artificial Sequence
<220> FEATURE:
<223> OTHER INFORMATION: Synthetic

<400> SEQUENCE: 411

Val Lys Met Ala Glu Thr Cys Pro Ile Phe Tyr
 1               5                  10

<210> SEQ ID NO 412
<211> LENGTH: 10
<212> TYPE: PRT
<213> ORGANISM: Artificial Sequence
<220> FEATURE:
<223> OTHER INFORMATION: Synthetic

<400> SEQUENCE: 412

Phe Ala Val Ala Asn Gly Asn Glu Leu Leu
 1               5                  10

<210> SEQ ID NO 413
<211> LENGTH: 7
<212> TYPE: PRT
<213> ORGANISM: Artificial Sequence
<220> FEATURE:
<223> OTHER INFORMATION: Synthetic

<400> SEQUENCE: 413

Ile Ser Arg Val Leu Asp Gly
 1               5

<210> SEQ ID NO 414
<211> LENGTH: 8
<212> TYPE: PRT
<213> ORGANISM: Artificial Sequence
<220> FEATURE:
<223> OTHER INFORMATION: Synthetic

<400> SEQUENCE: 414

Ile Ser Arg Val Leu Asp Gly Leu
 1               5

<210> SEQ ID NO 415
<211> LENGTH: 10
<212> TYPE: PRT
<213> ORGANISM: Artificial Sequence
<220> FEATURE:
<223> OTHER INFORMATION: Synthetic

<400> SEQUENCE: 415

Ile Ser Arg Val Leu Asp Gly Leu Val Met
 1               5                  10
```

<210> SEQ ID NO 416
<211> LENGTH: 19
<212> TYPE: PRT
<213> ORGANISM: Artificial Sequence
<220> FEATURE:
<223> OTHER INFORMATION: Synthetic

<400> SEQUENCE: 416

Leu Lys Leu Asn Thr Leu Gly Arg Glu Ile Cys Pro Ala Val Lys Arg
 1               5                  10                  15

Gly Val Asp

<210> SEQ ID NO 417
<211> LENGTH: 20
<212> TYPE: PRT
<213> ORGANISM: Artificial Sequence
<220> FEATURE:
<223> OTHER INFORMATION: Synthetic

<400> SEQUENCE: 417

Leu Lys Leu Asn Thr Leu Gly Arg Glu Ile Cys Pro Ala Val Lys Arg
 1               5                  10                  15

Gly Val Asp Leu
            20

<210> SEQ ID NO 418
<211> LENGTH: 15
<212> TYPE: PRT
<213> ORGANISM: Artificial Sequence
<220> FEATURE:
<223> OTHER INFORMATION: Synthetic

<400> SEQUENCE: 418

Tyr Val Glu Gln Val Ala Gln Tyr Lys Ala Leu Pro Val Val Leu
 1               5                  10                  15

<210> SEQ ID NO 419
<211> LENGTH: 11
<212> TYPE: PRT
<213> ORGANISM: Artificial Sequence
<220> FEATURE:
<223> OTHER INFORMATION: Synthetic

<400> SEQUENCE: 419

Val Ala Gln Tyr Lys Ala Leu Pro Val Val Leu
 1               5                  10

<210> SEQ ID NO 420
<211> LENGTH: 8
<212> TYPE: PRT
<213> ORGANISM: Artificial Sequence
<220> FEATURE:
<223> OTHER INFORMATION: Synthetic

<400> SEQUENCE: 420

Tyr Lys Ala Leu Pro Val Val Leu
 1               5

<210> SEQ ID NO 421
<211> LENGTH: 14
<212> TYPE: PRT
<213> ORGANISM: Artificial Sequence
<220> FEATURE:
<223> OTHER INFORMATION: Synthetic

```
<400> SEQUENCE: 421

Glu Asn Ala Arg Ile Leu Lys Asn Cys Val Asp Ala Lys Met
1               5                   10

<210> SEQ ID NO 422
<211> LENGTH: 18
<212> TYPE: PRT
<213> ORGANISM: Artificial Sequence
<220> FEATURE:
<223> OTHER INFORMATION: Synthetic

<400> SEQUENCE: 422

Leu Asp Lys Ile Tyr Thr Ser Pro Leu Cys Gly Pro Gly Gly Glu Gln
1               5                   10                  15

Lys Leu

<210> SEQ ID NO 423
<211> LENGTH: 14
<212> TYPE: PRT
<213> ORGANISM: Artificial Sequence
<220> FEATURE:
<223> OTHER INFORMATION: Synthetic

<400> SEQUENCE: 423

Ile Ser Glu Glu Asp Leu Ser Gly His His His His His His
1               5                   10

<210> SEQ ID NO 424
<211> LENGTH: 17
<212> TYPE: PRT
<213> ORGANISM: Artificial Sequence
<220> FEATURE:
<223> OTHER INFORMATION: Synthetic

<400> SEQUENCE: 424

Ile Ser Glu Glu Asp Leu Ser Gly His His His His His His Ser Ser
1               5                   10                  15

Gly

<210> SEQ ID NO 425
<211> LENGTH: 14
<212> TYPE: PRT
<213> ORGANISM: Artificial Sequence
<220> FEATURE:
<223> OTHER INFORMATION: Synthetic

<400> SEQUENCE: 425

Glu Asp Leu Ser Gly His His His His His His Ser Ser Gly
1               5                   10

<210> SEQ ID NO 426
<211> LENGTH: 4
<212> TYPE: PRT
<213> ORGANISM: Artificial Sequence
<220> FEATURE:
<223> OTHER INFORMATION: Synthetic

<400> SEQUENCE: 426

Tyr Val Glu Gln
1

<210> SEQ ID NO 427
<211> LENGTH: 363
<212> TYPE: DNA
<213> ORGANISM: Artificial Sequence
```

<220> FEATURE:
<223> OTHER INFORMATION: Synthetic

<400> SEQUENCE: 427
gaggtgcagc tggtggagtc gggcccagga ctggtgaacc cttcggagac cctgtccctc    60
acctgctctg tctctggtgg ctccatcagc agtgttaatt actactgggg ctggatccgc    120
cagtccccag ggaagggact ggagtggatt gggagtatct attatactgg gagtaccgac    180
tacaacccgt ccctcaagaa tcgagtcacc atatccgtag acacgtccaa gaaccagttc    240
tccctgaagc agacttctgt gaccgccgca gacacggctg tctattactg tgcgagacat    300
gtggcactgg ctgggggggct tttgatagtc tggggccagg ggacaatggt caccgtctct    360
tca    363

<210> SEQ ID NO 428
<211> LENGTH: 121
<212> TYPE: PRT
<213> ORGANISM: Artificial Sequence
<220> FEATURE:
<223> OTHER INFORMATION: Synthetic

<400> SEQUENCE: 428

Glu Val Gln Leu Val Glu Ser Gly Pro Gly Leu Val Asn Pro Ser Glu
1               5                   10                  15
Thr Leu Ser Leu Thr Cys Ser Val Ser Gly Gly Ser Ile Ser Ser Val
            20                  25                  30
Asn Tyr Tyr Trp Gly Trp Ile Arg Gln Ser Pro Gly Lys Gly Leu Glu
        35                  40                  45
Trp Ile Gly Ser Ile Tyr Tyr Thr Gly Ser Thr Asp Tyr Asn Pro Ser
    50                  55                  60
Leu Lys Asn Arg Val Thr Ile Ser Val Asp Thr Ser Lys Asn Gln Phe
65                  70                  75                  80
Ser Leu Lys Gln Thr Ser Val Thr Ala Ala Asp Thr Ala Val Tyr Tyr
                85                  90                  95
Cys Ala Arg His Val Ala Leu Ala Gly Gly Leu Leu Ile Val Trp Gly
            100                 105                 110
Gln Gly Thr Met Val Thr Val Ser Ser
        115                 120

<210> SEQ ID NO 429
<211> LENGTH: 30
<212> TYPE: DNA
<213> ORGANISM: Artificial Sequence
<220> FEATURE:
<223> OTHER INFORMATION: Synthetic

<400> SEQUENCE: 429
ggtggctcca tcagcagtgt taattactac    30

<210> SEQ ID NO 430
<211> LENGTH: 10
<212> TYPE: PRT
<213> ORGANISM: Artificial Sequence
<220> FEATURE:
<223> OTHER INFORMATION: Synthetic

<400> SEQUENCE: 430

Gly Gly Ser Ile Ser Ser Val Asn Tyr Tyr
1               5                   10

```
<210> SEQ ID NO 431
<211> LENGTH: 21
<212> TYPE: DNA
<213> ORGANISM: Artificial Sequence
<220> FEATURE:
<223> OTHER INFORMATION: Synthetic

<400> SEQUENCE: 431
atctattata ctgggagtac c                                              21

<210> SEQ ID NO 432
<211> LENGTH: 7
<212> TYPE: PRT
<213> ORGANISM: Artificial Sequence
<220> FEATURE:
<223> OTHER INFORMATION: Synthetic

<400> SEQUENCE: 432

Ile Tyr Tyr Thr Gly Ser Thr
1               5

<210> SEQ ID NO 433
<211> LENGTH: 39
<212> TYPE: DNA
<213> ORGANISM: Artificial Sequence
<220> FEATURE:
<223> OTHER INFORMATION: Synthetic

<400> SEQUENCE: 433
gcgagacatg tggcactggc tgggggctt ttgatagtc                            39

<210> SEQ ID NO 434
<211> LENGTH: 13
<212> TYPE: PRT
<213> ORGANISM: Artificial Sequence
<220> FEATURE:
<223> OTHER INFORMATION: Synthetic

<400> SEQUENCE: 434

Ala Arg His Val Ala Leu Ala Gly Gly Leu Leu Ile Val
1               5                   10

<210> SEQ ID NO 435
<211> LENGTH: 342
<212> TYPE: DNA
<213> ORGANISM: Artificial Sequence
<220> FEATURE:
<223> OTHER INFORMATION: Synthetic

<400> SEQUENCE: 435
gacatccaga tgacccagtc tccagactcc ctggctgtgt ctctgggcgc gagggccacc    60
atcaactgca gtccagcca aagtgtttta ttcagctcca acaataagaa cttcttagcc    120
tggtaccagc agaaaccagg acagcctcct accctgctca tttcctgggc atctacccgg    180
gaatccgggg tccctgaccg attcagtggg agcgggtctg ggacagattt cactctcacc    240
atcagcagcc tgcaggctga agatgtggca gtttatttct gtcaacaata ttataatagt    300
cctccacttt tcggccaggg gaccaaggtg gagatcaaac ga                      342

<210> SEQ ID NO 436
<211> LENGTH: 114
<212> TYPE: PRT
<213> ORGANISM: Artificial Sequence
<220> FEATURE:
<223> OTHER INFORMATION: Synthetic
```

<400> SEQUENCE: 436

Asp Ile Gln Met Thr Gln Ser Pro Asp Ser Leu Ala Val Ser Leu Gly
1               5                   10                  15

Ala Arg Ala Thr Ile Asn Cys Lys Ser Ser Gln Ser Val Leu Phe Ser
            20                  25                  30

Ser Asn Asn Lys Asn Phe Leu Ala Trp Tyr Gln Gln Lys Pro Gly Gln
        35                  40                  45

Pro Pro Thr Leu Leu Ile Ser Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Asn Ser Pro Pro Leu Phe Gly Gln Gly Thr Lys Val Glu Ile
            100                 105                 110

Lys Arg

<210> SEQ ID NO 437
<211> LENGTH: 36
<212> TYPE: DNA
<213> ORGANISM: Artificial Sequence
<220> FEATURE:
<223> OTHER INFORMATION: Synthetic

<400> SEQUENCE: 437
caaagtgttt tattcagctc caacaataag aacttc                              36

<210> SEQ ID NO 438
<211> LENGTH: 12
<212> TYPE: PRT
<213> ORGANISM: Artificial Sequence
<220> FEATURE:
<223> OTHER INFORMATION: Synthetic

<400> SEQUENCE: 438

Gln Ser Val Leu Phe Ser Ser Asn Asn Lys Asn Phe
1               5                   10

<210> SEQ ID NO 439
<211> LENGTH: 9
<212> TYPE: DNA
<213> ORGANISM: Artificial Sequence
<220> FEATURE:
<223> OTHER INFORMATION: Synthetic

<400> SEQUENCE: 439 tgggcatct                                                            9

<210> SEQ ID NO 440
<211> LENGTH: 3
<212> TYPE: PRT
<213> ORGANISM: Artificial Sequence
<220> FEATURE:
<223> OTHER INFORMATION: Synthetic

<400> SEQUENCE: 440

Trp Ala Ser
1

<210> SEQ ID NO 441
<211> LENGTH: 27
<212> TYPE: DNA

```
<213> ORGANISM: Artificial Sequence
<220> FEATURE:
<223> OTHER INFORMATION: Synthetic

<400> SEQUENCE: 441
caacaatatt ataatagtcc tccactt                                            27

<210> SEQ ID NO 442
<211> LENGTH: 9
<212> TYPE: PRT
<213> ORGANISM: Artificial Sequence
<220> FEATURE:
<223> OTHER INFORMATION: Synthetic

<400> SEQUENCE: 442

Gln Gln Tyr Tyr Asn Ser Pro Pro Leu
 1               5

<210> SEQ ID NO 443
<211> LENGTH: 360
<212> TYPE: DNA
<213> ORGANISM: Artificial Sequence
<220> FEATURE:
<223> OTHER INFORMATION: Synthetic

<400> SEQUENCE: 443
gaggtgcagc tggtggagtc tgggggaggc ttggtacagc ctgggggttc cctgagactc        60
tcctgtgcag tctctggatt cacctttagc aactatgcca tgaactgggt ccgccaggct       120
ccagggaagg gctggagtg gtctcagtt attagcgaca gtggtcgtag cacctactac         180
gcagactccg tgaagggccg gttcaccatc tccagagaca attccaagaa cacgctatat       240
ctgcaaatga acagcctgag agccgaggac acggccgtat atttctgtgc gaaaaggtat       300
aactggaact acactacttt tgactactgg ggccagggaa ccacggtcac cgtctcctca       360

<210> SEQ ID NO 444
<211> LENGTH: 120
<212> TYPE: PRT
<213> ORGANISM: Artificial Sequence
<220> FEATURE:
<223> OTHER INFORMATION: Synthetic

<400> SEQUENCE: 444

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Val Ile Ser Asp Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Arg Tyr Asn Trp Asn Leu His Tyr Phe Asp Tyr Trp Gly Gln
            100                 105                 110

Gly Thr Thr Val Thr Val Ser Ser
        115                 120

<210> SEQ ID NO 445
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 445
ggattcacct ttagcaacta tgcc                                           24

<210> SEQ ID NO 446
<211> LENGTH: 8
<212> TYPE: PRT
<213> ORGANISM: Artificial Sequence
<220> FEATURE:
<223> OTHER INFORMATION: Synthetic

<400> SEQUENCE: 446

Gly Phe Thr Phe Ser Asn Tyr Ala
 1               5

<210> SEQ ID NO 447
<211> LENGTH: 24
<212> TYPE: DNA
<213> ORGANISM: Artificial Sequence
<220> FEATURE:
<223> OTHER INFORMATION: Synthetic

<400> SEQUENCE: 447
attagcgaca gtggtcgtag cacc                                           24

<210> SEQ ID NO 448
<211> LENGTH: 8
<212> TYPE: PRT
<213> ORGANISM: Artificial Sequence
<220> FEATURE:
<223> OTHER INFORMATION: Synthetic

<400> SEQUENCE: 448

Ile Ser Asp Ser Gly Arg Ser Thr
 1               5

<210> SEQ ID NO 449
<211> LENGTH: 39
<212> TYPE: DNA
<213> ORGANISM: Artificial Sequence
<220> FEATURE:
<223> OTHER INFORMATION: Synthetic

<400> SEQUENCE: 449
gcgaaaaggt ataactggaa cttacactac tttgactac                           39

<210> SEQ ID NO 450
<211> LENGTH: 13
<212> TYPE: PRT
<213> ORGANISM: Artificial Sequence
<220> FEATURE:
<223> OTHER INFORMATION: Synthetic

<400> SEQUENCE: 450

Ala Lys Arg Tyr Asn Trp Asn Leu His Tyr Phe Asp Tyr
 1               5                  10

<210> SEQ ID NO 451
<211> LENGTH: 321
<212> TYPE: DNA
<213> ORGANISM: Artificial Sequence
<220> FEATURE:
```

<223> OTHER INFORMATION: Synthetic

<400> SEQUENCE: 451

```
gaaattgtgt tgacgcagtc tccagacttt cagtctgtga ctccaaagga gaaagtcacc    60
atcacctgcc gggccagtca gagcattggt ggtagcttac actggtacca gcagaaacca   120
gatcagtctc caaagctcct catcaagtat gcttcccagt ccttctcagg ggtcccctcg   180
aggttcagtg gcagtggatc tgggacagat ttcacccctca ccatcaatag cctggaagct   240
gaagatgctg caacgtatta ctgtcttcag agtagtagtt tacggacgtt cggccaaggg   300
accaaggtgg agatcaaacg a                                              321
```

<210> SEQ ID NO 452
<211> LENGTH: 107
<212> TYPE: PRT
<213> ORGANISM: Artificial Sequence
<220> FEATURE:
<223> OTHER INFORMATION: Synthetic

<400> SEQUENCE: 452

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Gly Ser
             20                  25                  30

Leu His Trp Tyr Gln Gln Lys Pro Asp Gln Ser Pro Lys Leu Leu Ile
         35                  40                  45

Lys Tyr Ala Ser Gln Ser Phe Ser Gly Val Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Leu Gln Ser Ser Ser Leu Arg Thr
                 85                  90                  95

Phe Gly Gln Gly Thr Lys Val Glu Ile Lys Arg
            100                 105
```

<210> SEQ ID NO 453
<211> LENGTH: 18
<212> TYPE: DNA
<213> ORGANISM: Artificial Sequence
<220> FEATURE:
<223> OTHER INFORMATION: Synthetic

<400> SEQUENCE: 453

```
cagagcattg gtggtagc                                                   18
```

<210> SEQ ID NO 454
<211> LENGTH: 6
<212> TYPE: PRT
<213> ORGANISM: Artificial Sequence
<220> FEATURE:
<223> OTHER INFORMATION: Synthetic

<400> SEQUENCE: 454

```
Gln Ser Ile Gly Gly Ser
 1               5
```

<210> SEQ ID NO 455
<211> LENGTH: 9
<212> TYPE: DNA
<213> ORGANISM: Artificial Sequence
<220> FEATURE:
<223> OTHER INFORMATION: Synthetic

<400> SEQUENCE: 455 tatgcttcc                                                                9

<210> SEQ ID NO 456
<211> LENGTH: 3
<212> TYPE: PRT
<213> ORGANISM: Artificial Sequence
<220> FEATURE:
<223> OTHER INFORMATION: Synthetic

<400> SEQUENCE: 456

Tyr Ala Ser
 1

<210> SEQ ID NO 457
<211> LENGTH: 24
<212> TYPE: DNA
<213> ORGANISM: Artificial Sequence
<220> FEATURE:
<223> OTHER INFORMATION: Synthetic

<400> SEQUENCE: 457
cttcagagta gtagtttacg gacg                                              24

<210> SEQ ID NO 458
<211> LENGTH: 8
<212> TYPE: PRT
<213> ORGANISM: Artificial Sequence
<220> FEATURE:
<223> OTHER INFORMATION: Synthetic

<400> SEQUENCE: 458

Leu Gln Ser Ser Ser Leu Arg Thr
 1               5

<210> SEQ ID NO 459
<211> LENGTH: 345
<212> TYPE: DNA
<213> ORGANISM: Artificial Sequence
<220> FEATURE:
<223> OTHER INFORMATION: Synthetic

<400> SEQUENCE: 459
gaggtgcagc tggtggagtc tgggggaggc ttggtacagc ctggggggtc cctgagactc        60
tcctgtgcag cctctggatt cacctttagc agttatgcca tgagctgggt ccgccaggct       120
ccagggaagg ggctggagtg gtctcagct attagtggtc gtggttataa cgcagactac       180
gcagactccg tgaagggccg gttcaccatc tccagagaca attccaagaa cacgctgtat       240
ctgcaaatga acagcctgag agccgaagac acggccgtat attactgtgc gaaattggaa       300
tactttgact actggggcca gggaaccacg gtcaccgtct cctca                      345

<210> SEQ ID NO 460
<211> LENGTH: 115
<212> TYPE: PRT
<213> ORGANISM: Artificial Sequence
<220> FEATURE:
<223> OTHER INFORMATION: Synthetic

<400> SEQUENCE: 460

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr

```
                20                  25                  30
Ala Met Ser Trp Val Arg Gln Ala Pro Gly Lys Gly Leu Glu Trp Val
            35                  40                  45

Ser Ala Ile Ser Gly Arg Gly Tyr Asn Ala Asp Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Leu Glu Tyr Phe Asp Tyr Trp Gly Gln Gly Thr Thr Val Thr
            100                 105                 110

Val Ser Ser
        115

<210> SEQ ID NO 461
<211> LENGTH: 24
<212> TYPE: DNA
<213> ORGANISM: Artificial Sequence
<220> FEATURE:
<223> OTHER INFORMATION: Synthetic

<400> SEQUENCE: 461
ggattcacct ttagcagtta tgcc                                            24

<210> SEQ ID NO 462
<211> LENGTH: 8
<212> TYPE: PRT
<213> ORGANISM: Artificial Sequence
<220> FEATURE:
<223> OTHER INFORMATION: Synthetic

<400> SEQUENCE: 462

Gly Phe Thr Phe Ser Ser Tyr Ala
 1               5

<210> SEQ ID NO 463
<211> LENGTH: 24
<212> TYPE: DNA
<213> ORGANISM: Artificial Sequence
<220> FEATURE:
<223> OTHER INFORMATION: Synthetic

<400> SEQUENCE: 463
attagtggtc gtggttataa cgca                                            24

<210> SEQ ID NO 464
<211> LENGTH: 8
<212> TYPE: PRT
<213> ORGANISM: Artificial Sequence
<220> FEATURE:
<223> OTHER INFORMATION: Synthetic

<400> SEQUENCE: 464

Ile Ser Gly Arg Gly Tyr Asn Ala
 1               5

<210> SEQ ID NO 465
<211> LENGTH: 24
<212> TYPE: DNA
<213> ORGANISM: Artificial Sequence
<220> FEATURE:
<223> OTHER INFORMATION: Synthetic

<400> SEQUENCE: 465
```
gcgaaattgg aatactttga ctac        24

<210> SEQ ID NO 466
<211> LENGTH: 8
<212> TYPE: PRT
<213> ORGANISM: Artificial Sequence
<220> FEATURE:
<223> OTHER INFORMATION: Synthetic

<400> SEQUENCE: 466

Ala Lys Leu Glu Tyr Phe Asp Tyr
1               5

<210> SEQ ID NO 467
<211> LENGTH: 324
<212> TYPE: DNA
<213> ORGANISM: Artificial Sequence
<220> FEATURE:
<223> OTHER INFORMATION: Synthetic

<400> SEQUENCE: 467
gacatccagt tgacccagtc tccttccacc ctgtctgcat ctgtaggaga cagagtcacc        60
atcacttgcc gggccagtca gagtattagt agctggttgg cctggtatca gcagaaacca       120
gggaaagccc ctaagctcct gatctataag gcgtctagtt tagaaagtgg ggtcccatca       180
aggttcagcg gcagtggatc tgggacagat ttcactctca ccatcagcag cctgaggcct       240
gaagattttg caacttatta ctgccaacag tataatagtt accctctgac tttcggcgga       300
gggaccaagg tggaaatcaa acga                                              324

<210> SEQ ID NO 468
<211> LENGTH: 108
<212> TYPE: PRT
<213> ORGANISM: Artificial Sequence
<220> FEATURE:
<223> OTHER INFORMATION: Synthetic

<400> SEQUENCE: 468

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Arg Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 469
<211> LENGTH: 18
<212> TYPE: DNA
<213> ORGANISM: Artificial Sequence
<220> FEATURE:
<223> OTHER INFORMATION: Synthetic

<400> SEQUENCE: 469
cagagtatta gtagctgg                                                     18

<210> SEQ ID NO 470
<211> LENGTH: 6
<212> TYPE: PRT
<213> ORGANISM: Artificial Sequence
<220> FEATURE:
<223> OTHER INFORMATION: Synthetic

<400> SEQUENCE: 470

Gln Ser Ile Ser Ser Trp
 1               5

<210> SEQ ID NO 471
<211> LENGTH: 9
<212> TYPE: DNA
<213> ORGANISM: Artificial Sequence
<220> FEATURE:
<223> OTHER INFORMATION: Synthetic

<400> SEQUENCE: 471 aaggcgtct                                                                9

<210> SEQ ID NO 472
<211> LENGTH: 3
<212> TYPE: PRT
<213> ORGANISM: Artificial Sequence
<220> FEATURE:
<223> OTHER INFORMATION: Synthetic

<400> SEQUENCE: 472

Lys Ala Ser
 1

<210> SEQ ID NO 473
<211> LENGTH: 27
<212> TYPE: DNA
<213> ORGANISM: Artificial Sequence
<220> FEATURE:
<223> OTHER INFORMATION: Synthetic

<400> SEQUENCE: 473
caacagtata atagttaccc tctgact                                           27

<210> SEQ ID NO 474
<211> LENGTH: 9
<212> TYPE: PRT
<213> ORGANISM: Artificial Sequence
<220> FEATURE:
<223> OTHER INFORMATION: Synthetic

<400> SEQUENCE: 474

Gln Gln Tyr Asn Ser Tyr Pro Leu Thr
 1               5

<210> SEQ ID NO 475
<211> LENGTH: 345
<212> TYPE: DNA
<213> ORGANISM: Artificial Sequence
<220> FEATURE:
<223> OTHER INFORMATION: Synthetic

<400> SEQUENCE: 475
gaggtgcagc tggtggagtc tgggggaggc ttggtacagc ctggggggtc cctgagactc        60
tcctgtgcag cctctggatt cacctttagc acctatgcca tgcactgggt ccgccaggct       120

```
ccagggaagg ggctggagtg ggtctcaagt attagtggtc gtggtcgtaa ctcagaccac      180
gcagactccg tgaagggccg gttcaccatc tccagagaca attccaagaa cacgctctat      240
ctacaaatga acagcctgag agccgaggac acggccgtat attactgtgc gaggaccgaa      300
tacttccacc actggggcca gggcaccacg gtcaccgtct cctca                     345
```

```
<210> SEQ ID NO 476
<211> LENGTH: 115
<212> TYPE: PRT
<213> ORGANISM: Artificial Sequence
<220> FEATURE:
<223> OTHER INFORMATION: Synthetic

<400> SEQUENCE: 476
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ser Ser Ile Ser Gly Arg Gly Arg Asn Ser Asp His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Glu Tyr Phe His His Trp Gly Gln Gly Thr Thr Val Thr
            100                 105                 110

Val Ser Ser
        115

```
<210> SEQ ID NO 477
<211> LENGTH: 24
<212> TYPE: DNA
<213> ORGANISM: Artificial Sequence
<220> FEATURE:
<223> OTHER INFORMATION: Synthetic

<400> SEQUENCE: 477
ggattcacct ttagcaccta tgcc                                             24
```

```
<210> SEQ ID NO 478
<211> LENGTH: 8
<212> TYPE: PRT
<213> ORGANISM: Artificial Sequence
<220> FEATURE:
<223> OTHER INFORMATION: Synthetic

<400> SEQUENCE: 478
```

Gly Phe Thr Phe Ser Thr Tyr Ala
1               5

```
<210> SEQ ID NO 479
<211> LENGTH: 24
<212> TYPE: DNA
<213> ORGANISM: Artificial Sequence
<220> FEATURE:
<223> OTHER INFORMATION: Synthetic

<400> SEQUENCE: 479
attagtggtc gtggtcgtaa ctca                                             24
```

<210> SEQ ID NO 480
<211> LENGTH: 8
<212> TYPE: PRT
<213> ORGANISM: Artificial Sequence
<220> FEATURE:
<223> OTHER INFORMATION: Synthetic

<400> SEQUENCE: 480

Ile Ser Gly Arg Gly Arg Asn Ser
1               5

<210> SEQ ID NO 481
<211> LENGTH: 24
<212> TYPE: DNA
<213> ORGANISM: Artificial Sequence
<220> FEATURE:
<223> OTHER INFORMATION: Synthetic

<400> SEQUENCE: 481
gcgaggaccg aatacttcca ccac                                          24

<210> SEQ ID NO 482
<211> LENGTH: 8
<212> TYPE: PRT
<213> ORGANISM: Artificial Sequence
<220> FEATURE:
<223> OTHER INFORMATION: Synthetic

<400> SEQUENCE: 482

Ala Arg Thr Glu Tyr Phe His His
1               5

<210> SEQ ID NO 483
<211> LENGTH: 324
<212> TYPE: DNA
<213> ORGANISM: Artificial Sequence
<220> FEATURE:
<223> OTHER INFORMATION: Synthetic

<400> SEQUENCE: 483
gacatcgtga tgacccagtc tccatcctca ctgtctgcat ctgtaggaga cagaatcacc      60
atcacttgtc gggcgagtca ggacattaac aattatttag cctggtttca gcagaaacca     120
ggaaaagccc ctaagtccct gatctatggt gcatccagct tgcaaagtgg ggtcccatca     180
aagttcagcg gcagtggatc tgggacagat ttcactctca ccatcagcag cctgcagcct     240
gaagattttg caacttatta ctgccaacaa tatacgttct taccattcac tttcggccct     300
gggaccaagg tgaaaatcaa acga                                          324

<210> SEQ ID NO 484
<211> LENGTH: 108
<212> TYPE: PRT
<213> ORGANISM: Artificial Sequence
<220> FEATURE:
<223> OTHER INFORMATION: Synthetic

<400> SEQUENCE: 484

Asp Ile Val Met Thr Gln Ser Pro Ser Ser Leu Ser Ala Ser Val Gly
1               5                   10                  15

Asp Arg Ile Thr Ile Thr Cys Arg Ala Ser Gln Asp Ile Asn Asn Tyr
                20                  25                  30

Leu Ala Trp Phe Gln Gln Lys Pro Gly Lys Ala Pro Lys Ser Leu Ile
            35                  40                  45

-continued

```
Tyr Gly Ala Ser Ser Leu Gln Ser Gly Val Pro Ser Lys Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Thr Phe Leu Pro Phe
                 85                  90                  95
Thr Phe Gly Pro Gly Thr Lys Val Lys Ile Lys Arg
            100                 105
```

<210> SEQ ID NO 485
<211> LENGTH: 18
<212> TYPE: DNA
<213> ORGANISM: Artificial Sequence
<220> FEATURE:
<223> OTHER INFORMATION: Synthetic

<400> SEQUENCE: 485
caggacatta acaattat                                                    18

<210> SEQ ID NO 486
<211> LENGTH: 6
<212> TYPE: PRT
<213> ORGANISM: Artificial Sequence
<220> FEATURE:
<223> OTHER INFORMATION: Synthetic

<400> SEQUENCE: 486

```
Gln Asp Ile Asn Asn Tyr
 1               5
```

<210> SEQ ID NO 487
<211> LENGTH: 9
<212> TYPE: DNA
<213> ORGANISM: Artificial Sequence
<220> FEATURE:
<223> OTHER INFORMATION: Synthetic

<400> SEQUENCE: 487 ggtgcatcc                                                               9

<210> SEQ ID NO 488
<211> LENGTH: 3
<212> TYPE: PRT
<213> ORGANISM: Artificial Sequence
<220> FEATURE:
<223> OTHER INFORMATION: Synthetic

<400> SEQUENCE: 488

```
Gly Ala Ser
 1
```

<210> SEQ ID NO 489
<211> LENGTH: 27
<212> TYPE: DNA
<213> ORGANISM: Artificial Sequence
<220> FEATURE:
<223> OTHER INFORMATION: Synthetic

<400> SEQUENCE: 489
caacaatata cgttcttacc attcact                                          27

<210> SEQ ID NO 490
<211> LENGTH: 9
<212> TYPE: PRT
<213> ORGANISM: Artificial Sequence

```
<220> FEATURE:
<223> OTHER INFORMATION: Synthetic

<400> SEQUENCE: 490

Gln Gln Tyr Thr Phe Leu Pro Phe Thr
1               5
```

HUMAN ANTIBODIES TO FEL D1 AND METHODS OF USE THEREOF

CROSS-REFERENCE TO RELATED APPLICATIONS

This application is a divisional of U.S. patent application Ser. No. 14/732,578, filed Jun. 5, 2015, which is a divisional of U.S. patent application Ser. No. 13/875,401 filed May 2, 2013, now U.S. Pat. No. 9,079,948, which claims the benefit under 35 U.S.C § 119(e) of U.S. Provisional Application Ser. Nos. 61/642,083, filed May 3, 2012; 61/718,044, filed Oct. 24, 2012, and 61/783,312, filed Mar. 14, 2013, all of which are herein specifically incorporated by reference in their entirety.

FIELD OF THE INVENTION

The present invention is related to human antibodies and antigen-binding fragments of human antibodies that specifically bind to the cat allergen Fel d1, therapeutic compositions comprising the antibodies and methods of using those antibodies.

STATEMENT OF RELATED ART

The Fel d1 protein is a secreted cat protein, which belongs to the secretoglobin family of small disulfide linked heterodimeric proteins found only in mammals (Klug, J. et al. (2000), Ann. N.Y. Acad. Sci. 923:348-354). It is the major cause of cat allergies in humans (Platts-Mills, T. A., et al. (1997), J. Allergy Clin. Immunol. 100:S2-S24). About 90-95% of patients allergic to cats have an IgE response to the Fel d 1 protein (van Ree, et al. (1999), J. Allergy Clin. Immunol. 104:1223-1230). The symptoms in a patient who experiences an allergic response to Fel d1 can range from mild rhinitis and conjunctivitis to life-threatening asthmatic responses. Fel d1 is produced by sebaceous glands and squamous glands and squamous epithelial cells and is transferred to the pelt by licking and grooming (Bartholome, K. et al. (1985), J. Allergy Clin. Immunol. 76:503-506; Charpin, C. et al. (1991), J. Allergy Clin. Immunol. 88:77-82; Dabrowski, A. J. (1990), et al. J. Allergy Clin. Immunol. 86:462-465). It is also present in the salivary, perianal and lachrymal glands (Andersen, M. C., et al. (1985), J. Allergy Clin. Immunol. 76:563-569; van Milligen, F. J. (1992), et al., Int. Arch. Allergy Appl. Immunol. 92(4):375-378) and the principal reservoirs appear to be the skin and the fur (Mata, P. et al. (1992), Ann. Allergy 69(4):321-322).

Natural Fel d1 is an approximately 18 kDa heterodimeric glycoprotein. Each heterodimer comprises two polypeptide chains, which are covalently linked by three inter-chain disulfide bonds and which are encoded by two separate genes (Duffort, O A, et al., (1991), Mol. Immunol. 28:301-309; Morgenstern, J P, et al., (1991), PNAS 88:9690-9694; Griffith, I. J., et al. (1992), Gene 113:263-268; Kristensen, A. K. et al. (1997), Biol. Chem. 378:899-908). Chain 1 comprises 70 amino acid residues and chain 2 comprises about 90-92 amino acid residues. Structurally the two chains are similar, but have only 10-15% sequence identity (Kaiser, L. et al. (2003), J. Biol. Chem. 278(39):37730-37735). Although each chain is sometimes individually referred to as Fel d1, both chains are needed for the full protein allergen.

The Fel d1 protein is of an unknown function to the animal but causes an IgG or IgE reaction in sensitive humans (either as an allergic or asthmatic response). Although other cat allergens are known, including Fel d2 (albumin) and Fel d3 (cystatin), 60% to 90% of the anti-cat IgE produced is directed against Fel d1 (Leitermann, K. et al., (1984), J Allergy Clin. Immunol. 74:147-153; Lowenstein, H. et al., (1985), Allergy 40:430-441; van Ree, R. et al., (1999), J. Allergy Clin. Immunol. 104:1223-1230; Ichikawa, K. et al., (2011), Clin. Exp. Allergy, 31:1279-1286).

Immunoglobulin E (IgE) is responsible for type 1 hypersensitivity, which manifests itself in allergic rhinitis, allergic conjunctivitis, hay fever, allergic asthma, bee venom allergy, and food allergies. IgE circulates in the blood and binds to high-affinity FcεR1α receptors for IgE on basophils and mast cells. In most allergic responses, the allergens enter the body through inhalation, ingestion, or through the skin. The allergen then binds to preformed IgE already bound to the high affinity receptor on the surfaces of mast cells and basophils, resulting in cross-linking of several IgE molecules and triggering the release of histamine and other inflammatory mediators causing the various allergic symptoms.

The treatment for allergies includes steroids for suppressing the immune activity and bronchial dilators for relieving asthma symptoms. Desensitization therapy is also used for severely allergic patients. Peptide vaccine combinations have been tested for desensitizing individuals to particular allergens, e.g. Fel d1 (See US2010/0239599A1 and EP2380591A2). Antibodies have been proposed as a treatment for allergies, since they may be able to block the entry of allergenic molecules into the mucosal tissues, or may bind the allergen before it has the opportunity to bind to the IgE bound to the high affinity receptor on mast cells or basophils, thus preventing the release of histamine and other inflammatory mediators from these cells.

U.S. Pat. No. 5,670,626 describes the use of monoclonal antibodies for the treatment of IgE-mediated allergic diseases such as allergic rhinitis, allergic asthma, and allergic conjunctivitis by blocking the binding of allergens to the mucosal tissue. U.S. Pat. No. 6,849,259 describes the use of allergen-specific antibodies to inhibit allergic inflammation in an in vivo mouse model of allergy. Milk-based and egg-based antibody systems have been described. For example, US20030003133A1 discloses using milk as a carrier for allergens for inducing oral tolerance to cat dander and other allergens. Compositions and methods for reducing an allergic response in an animal to an allergen in the environment through use of a molecule that inhibits the ability of the allergen to bind to mast cells was described in US2010/0143266. Other antibodies to Fel d1 were described by de Groot et. al. (de Groot et. al., (1988), J. Allergy Clin. Immunol. 82:778-786).

BRIEF SUMMARY OF THE INVENTION

The invention provides fully human monoclonal antibodies (mAbs) and antigen-binding fragments thereof that bind specifically to the cat allergen, Fel d1. Such antibodies may be useful to bind the Fel d1 allergen in vivo following exposure of a sensitized patient to the cat allergen, and as such, may act to either promote clearance of Fel d1 or to block the binding of the allergen to pre-formed IgE on the surface of mast cells or basophils. By doing so, the antibodies of the invention may prevent the release of histamine or other inflammatory mediators from mast cells or basophils, thereby preventing or diminishing the untoward effects observed in patients sensitized to the cat allergen. In certain embodiments, the antibodies may be capable of reducing, minimizing, or preventing at least one symptom in a patient sensitive to the Fel d1 cat allergen, such as sneezing, congestion, nasal blockage, coughing, wheezing, bronchoconstriction, rhinitis, or conjunctivitis. In certain embodiments, the antibodies may be capable of preventing even more serious in vivo complications associated with exposure to the cat allergen in sensitized individuals, such as asthmatic responses, anaphylaxis, or even death.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., (2000), J. Immunol. 164:1925-1933).

A first aspect of the invention provides an isolated human monoclonal antibody or antigen-binding fragment thereof that binds specifically to Fel d1.

In one embodiment, the antibody or antigen binding fragment thereof is an isotype other than an IgA isotype.

In one embodiment, the isolated human antibody or antigen-binding fragment thereof has an isotype selected from the group consisting of an IgG1, an IgG2 and an IgG4.

In one embodiment, the isolated human antibody or antigen-binding fragment thereof binds specifically to Fel d1 with a $K_D$ equal to or less than $10^{-6}$ M. In one embodiment, the isolated human antibody or antigen-binding fragment thereof binds specifically to Fel d1 with a $K_D$ equal to or less than 1.8 nM.

In one embodiment, the isolated human antibody or antigen-binding fragment thereof comprises the three heavy chain CDRs (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370 and 460; and the three light chain CDRs (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378 and 468. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997), *J. Mol. Biol.* 273:927-948; and Martin et al., (1989), *Proc. Natl. Acad. Sci. USA* 86:9268-9272. Public databases are also available for identifying CDR sequences within an antibody.

In one embodiment, the isolated human antibody or antigen-binding fragment thereof comprises the three heavy chain CDRs (HCDR1, HCDR2 and HCDR3) contained within any one of the heavy chain variable region (HCVR) sequences selected from the group consisting of SEQ ID NOs: 18, 66, 130, 162, 242, 306, 322, 370 and 460; and the three light chain CDRs (LCDR1, LCDR2 and LCDR3) contained within any one of the light chain variable region (LCVR) sequences selected from the group consisting of SEQ ID NOs: 26, 74, 138, 170, 250, 314, 330, 378 and 468.

In one embodiment, the isolated human antibody or antigen-binding fragment thereof comprises a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370 and 460.

In one embodiment, the isolated human antibody or antigen-binding fragment thereof comprises a HCVR having an amino acid sequence selected from the group consisting of SEQ ID NOs: 18, 66, 130, 162, 242, 306, 322, 370 and 460.

In one embodiment, the isolated human antibody or antigen-binding fragment thereof comprises a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378 and 468.

In one embodiment, the isolated human antibody or antigen-binding fragment thereof comprises a LCVR having an amino acid sequence selected from the group consisting of SEQ ID NOs: 26, 74, 138, 170, 250, 314, 330, 378 and 468.

In one embodiment, the isolated human antibody or antigen-binding fragment thereof comprises: (a) a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370 and 460; and (b) a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378 and 468.

In one embodiment, the isolated human antibody or antigen-binding fragment thereof comprises: (a) a HCVR having an amino acid sequence selected from the group consisting of SEQ ID NOs: 18, 66, 130, 162, 242, 306, 322, 370 and 460; and (b) a LCVR having an amino acid sequence selected from the group consisting of SEQ ID NO: 26, 74, 138, 170, 250, 314, 330, 378 and 468.

In one embodiment, the isolated human antibody or antigen-binding fragment thereof comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 372 and 462;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326, 342, 358, 374 and 464;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, 344, 360, 376 and 466;

(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 380 and 470;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 382 and 472; and (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336, 352, 368, 384 and 474.

In one embodiment, the isolated human antibody or antigen-binding fragment thereof comprises:
(a) a HCDR1 domain having an amino acid sequence selected from the group consisting of SEQ ID NOs: 20, 68, 132, 164, 244, 308, 324, 372 and 462;
(b) a HCDR2 domain having an amino acid sequence selected from the group consisting of SEQ ID NOs: 22, 70, 134, 166, 246, 310, 326, 374 and 464;
(c) a HCDR3 domain having an amino acid sequence selected from the group consisting of SEQ ID NOs: 24, 72, 136, 168, 248, 312, 328, 376 and 466;
(d) a LCDR1 domain having an amino acid sequence selected from the group consisting of SEQ ID NOs: 28, 76, 140, 172, 252, 316, 332, 380 and 470;
(e) a LCDR2 domain having an amino acid sequence selected from the group consisting of SEQ ID NOs: 30, 78, 142, 174, 254, 318, 334, 382 and 472; and
(f) a LCDR3 domain having an amino acid sequence selected from the group consisting of SEQ ID NOs: 32, 80, 144, 176, 256, 320, 336, 384 and 474.

In one embodiment, the isolated human antibody or antigen-binding fragment thereof comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378 and 460/468.

In one embodiment, the isolated human antibody or antigen-binding fragment thereof comprises a HCVR/LCVR amino acid sequence pair selected from the group consisting of SEQ ID NOs: 18/26, 66/74, 130/138, 162/170, 242/250, 306/314, 322/330, 370/378 and 460/468.

In one embodiment, the isolated human antibody or antigen-binding fragment thereof which binds to Fel d1 comprises a HCVR/LCVR amino acid sequence pair selected from the group consisting of SEQ ID NOs: 18/26, 66/74, 130/138 and 162/170.

In one embodiment, the isolated human antibody or antigen-binding fragment thereof which binds to Fel d1 comprises the HCVR/LCVR amino acid sequence pair selected from the group consisting of SEQ ID NOs: 18/26 and 322/330.

In one embodiment, the isolated human antibody or antigen-binding fragment thereof which binds to Fel d1 comprises the HCVR/LCVR amino acid sequence pair selected from the group consisting of SEQ ID NOs: 18/26 and 306/314.

In one embodiment, the isolated human antibody or antigen-binding fragment thereof which binds to Fel d1 comprises the HCVR/LCVR amino acid sequence pair selected from the group consisting of SEQ ID NOs: 18/26 and 370/378.

In one embodiment, the isolated human antibody or antigen-binding fragment thereof which binds to Fel d1 comprises the HCVR/LCVR amino acid sequence pair selected from the group consisting of SEQ ID NOs: 242/250 and 306/314.

In one embodiment, the isolated human antibody or antigen-binding fragment thereof which binds to Fel d1 comprises the HCVR/LCVR amino acid sequence pair selected from the group consisting of SEQ ID NOs: 242/250 and 322/330.

In one embodiment, the isolated human antibody or antigen-binding fragment thereof which binds specifically to Fel d1 interacts with at least one amino acid sequence selected from the group consisting of amino acid residues ranging from about position 15 to about position 24 of SEQ ID NO: 396; amino acid residues ranging from about position 85 to about position 103 of SEQ ID NO: 396; amino acid residues ranging from about position 85 to about position 104 of SEQ ID NO: 396; and amino acid residues ranging from about position 113 to about position 116 of SEQ ID NO: 396.

In one embodiment, the isolated human antibody or antigen-binding fragment thereof which binds to Fel d1 interacts with amino acid residues ranging from about position 15 to about position 24 of SEQ ID NO: 396.

In one embodiment, the isolated human antibody or antigen-binding fragment thereof which binds to Fel d1 interacts with amino acid residues ranging from about position 85 to about position 103 of SEQ ID NO: 396.

In one embodiment, the isolated human antibody or antigen-binding fragment thereof which binds to Fel d1 interacts with amino acid residues ranging from about position 85 to about position 104 of SEQ ID NO: 396.

In one embodiment, the isolated human antibody or antigen-binding fragment thereof which binds to Fel d1 interacts with amino acid residues ranging from about position 113 to about position 116 of SEQ ID NO: 396.

In one embodiment, the isolated human antibody or antigen-binding fragment thereof which binds to Fel d1 interacts with at least one amino acid sequence selected from the group consisting of SEQ ID NO: 402, 403, 404 and 412.

In one embodiment, the isolated human antibody or antigen-binding fragment thereof which binds to Fel d1 interacts with SEQ ID NO: 402.

In one embodiment, the isolated human antibody or antigen-binding fragment thereof which binds to Fel d1 interacts with SEQ ID NO: 403.

In one embodiment, the isolated human antibody or antigen-binding fragment thereof which binds to Fel d1 interacts with SEQ ID NO: 404.

In one embodiment, the isolated human antibody or antigen-binding fragment thereof which binds to Fel d1 interacts with SEQ ID NO: 426.

In one embodiment, the isolated human antibody or antigen-binding fragment thereof which binds to Fel d1 interacts with SEQ ID NO: 412.

In one embodiment, the isolated human antibody or antigen binding fragment thereof that interacts with SEQ ID NOs: 402, 403, 404 and/or 426, comprises the three HCDRs contained in the heavy chain variable region of SEQ ID NO: 18 and the three LCDRs contained in the light chain variable region of SEQ ID NO: 26.

In one embodiment, the isolated human antibody or antigen binding fragment thereof that interacts with SEQ ID NOs: 402, 403, 404 and/or 426, comprises a HCDR1 of SEQ ID NO: 20; a HCDR2 of SEQ ID NO: 22; a HCDR3 of SEQ ID NO: 24; a LCDR1 of SEQ ID NO: 28; a LCDR2 of SEQ ID NO: 30 and a LCDR3 of SEQ ID NO: 32.

In one embodiment, the isolated human antibody or antigen binding fragment thereof that interacts with SEQ ID NO: 412 comprises the three HCDRs contained in the heavy chain variable region of SEQ ID NO: 306 and the three LCDRs contained in the light chain variable region of SEQ ID NO: 314.

In one embodiment, the isolated human antibody or antigen binding fragment thereof that interacts with SEQ ID NO: 412 comprises a HCDR1 of SEQ ID NO: 308; a HCDR2 of SEQ ID NO: 310; a HCDR3 of SEQ ID NO: 312; a LCDR1 of SEQ ID NO: 316; a LCDR2 of SEQ ID NO: 318 and a LCDR3 of SEQ ID NO: 320.

In one embodiment, the human antibody or antigen binding fragment thereof that binds Fel d1 comprises the HCDR1, HCDR2 and HCDR3 amino acid sequences of SEQ ID NO: 20, 22 and 24, respectively and LCDR1, LCDR2 and LCDR3 amino acid sequences of SEQ ID NO: 28, 30 and 32, respectively.

In one embodiment, the human antibody or antigen binding fragment thereof that binds to Fel d1 comprises the HCDR1, HCDR2 and HCDR3 amino acid sequences of SEQ ID NO: 68, 70 and 72, respectively and LCDR1, LCDR2 and LCDR3 amino acid sequences of SEQ ID NO: 76, 78 and 80, respectively.

In one embodiment, the human antibody or antigen binding fragment thereof that binds to Fel d1 comprises the HCDR1, HCDR2 and HCDR3 amino acid sequences of SEQ ID NO: 132, 134 and 136, respectively and LCDR1, LCDR2 and LCDR3 amino acid sequences of SEQ ID NO: 140, 142 and 144, respectively.

In one embodiment, the human antibody or antigen binding fragment thereof that binds to Fel d1 comprises the HCDR1, HCDR2 and HCDR3 amino acid sequences of SEQ ID NO: 164, 166 and 168, respectively and LCDR1, LCDR2 and LCDR3 amino acid sequences of SEQ ID NO: 172, 174 and 176, respectively.

In one embodiment, the human antibody or antigen binding fragment thereof that binds to Fel d1 comprises the HCDR1, HCDR2 and HCDR3 amino acid sequences of SEQ ID NO: 244, 246 and 248, respectively and LCDR1, LCDR2 and LCDR3 amino acid sequences of SEQ ID NO: 252, 254 and 256, respectively.

In one embodiment, the human antibody or antigen binding fragment thereof that binds to Fel d1 comprises the HCDR1, HCDR2 and HCDR3 amino acid sequences of SEQ ID NO: 308, 310 and 312, respectively and LCDR1, LCDR2 and LCDR3 amino acid sequences of SEQ ID NO: 316, 318 and 320, respectively.

In one embodiment, the human antibody or antigen binding fragment thereof that binds to Fel d1 comprises the HCDR1, HCDR2 and HCDR3 amino acid sequences of SEQ ID NO: 324, 326 and 328, respectively and LCDR1, LCDR2 and LCDR3 amino acid sequences of SEQ ID NO: 332, 334 and 336, respectively.

In one embodiment, the human antibody or antigen binding fragment thereof that binds to Fel d1 comprises the HCDR1, HCDR2 and HCDR3 amino acid sequences of SEQ ID NO: 372, 374 and 376 respectively and LCDR1, LCDR2 and LCDR3 amino acid sequences of SEQ ID NO: 380, 382 and 384, respectively.

In one embodiment, the invention provides a fully human monoclonal antibody or antigen-binding fragment thereof that binds to Fel d1, wherein the antibody or fragment thereof exhibits one or more of the following characteristics: (i) comprises a HCVR having an amino acid sequence selected from the group consisting of SEQ ID NO: 18, 66, 130, 162, 242, 306, 322, 370 and 460, or a substantially similar sequence thereof having at least 90%, at least 95%, at least 98% or at least 99% sequence identity; (ii) comprises a LCVR having an amino acid sequence selected from the group consisting of SEQ ID NO: 26, 74, 138, 170, 250, 314, 330, 378 and 468, or a substantially similar sequence thereof having at least 90%, at least 95%, at least 98% or at least 99% sequence identity; (iii) comprises a HCDR3 domain having an amino acid sequence selected from the group consisting of SEQ ID NO: 24, 72, 136, 168, 248, 312, 328, 376 and 466, or a substantially similar sequence thereof having at least 90%, at least 95%, at least 98% or at least 99% sequence identity; and a LCDR3 domain having an amino acid sequence selected from the group consisting of SEQ ID NO: 32, 80, 144, 176, 256, 320, 336, 384 and 474, or a substantially similar sequence thereof having at least 90%, at least 95%, at least 98% or at least 99% sequence identity; (iv) comprises a HCDR1 domain having an amino acid sequence selected from the group consisting of SEQ ID NO: 20, 68, 132, 164, 244, 308, 324, 372 and 462, or a substantially similar sequence thereof having at least 90%, at least 95%, at least 98% or at least 99% sequence identity; a HCDR2 domain having an amino acid sequence selected from the group consisting of SEQ ID NO: 22, 70, 134, 166, 246, 310, 326, 374 and 464, or a substantially similar sequence thereof having at least 90%, at least 95%, at least 98% or at least 99% sequence identity; a LCDR1 domain having an amino acid sequence selected from the group consisting of SEQ ID NO: 28, 76, 140, 172, 252, 316, 332, 380 and 470, or a substantially similar sequence thereof having at least 90%, at least 95%, at least 98% or at least 99% sequence identity; and a LCDR2 domain having an amino acid sequence selected from the group consisting of SEQ ID NO: 30, 78, 142, 174, 254, 318, 334, 382 and 472, or a substantially similar sequence thereof having at least 90%, at least 95%, at least 98% or at least 99% sequence identity; (v) binds to Fel d1 with a $K_D$ equal to or less than $10^{-6}$ and preferably equal to or less than $10^{-9}$; (vi) demonstrates efficacy in at least one animal model of anaphylaxis or inflammation; or (vii) competes with a reference antibody for binding to Fel d1.

In one embodiment, a "reference antibody" may include, for example, antibodies having a combination of heavy chain and light chain amino acid sequence pairs selected from the group consisting of 18/26, 66/74, 130/138, 162/170, 242/250, 306/314, 322/330, 370/378 and 460/468.

In one embodiment, the fully human monoclonal antibody or antigen binding fragment thereof that binds to Fel d1 comprises a HCDR1 sequence comprising the formula $X^1-X^2-X^3-X^4-X^5-X^6-X^7-X^8$ (SEQ ID NO:386) wherein $X^1$ is Gly, $X^2$ is Phe, Tyr or Gly, $X^3$ is Thr or Ser, $X^4$ is Phe or Ile, $X^5$ is Ser, Arg, Thr, or Asn, $X^6$ is Asn, Thr, Asp, or Ser, $X^7$ is Tyr, and $X^8$ is Asn, Tyr, or Ala; a HCDR2 sequence comprising the formula $X^1-X^2-X^3-X^4-X^5-X^6-X^7-X^8$ (SEQ ID NO: 387), wherein $X^1$ is Ile, $X^2$ is Tyr, Ser, or Asn, $X^3$ is Tyr, Ser, Gly, Pro, or Asp, $X^4$ is Asp, Arg, or Ser, $X^5$ is Gly, Val, or Ser, $X^6$ is Ser, Gly, Arg, or Tyr, $X^7$ is Tyr, Arg, Thr, Ser, or Asn, and $X^8$ is Ile, Thr, Ala, Ser, or absent; a HCDR3 sequence comprising the formula $X^1-X^2-X^3-X^4-X^5-X^6-X^7-X^8-X^9-X^{10}-X^{11}-X^{12}-X^{13}-X^{14}-X^{15}-X^{16}$ (SEQ ID NO: 388), wherein $X^1$ is Ala, $X^2$ is Lys or Arg, $X^3$ is Arg, Gly, His, Ser, Asp, Leu, or Thr, $X^4$ is Thr, Pro, Arg, Gly, or Glu, $X^5$ is Leu, Val, Gly, Lys, Tyr, or Asn, $X^6$ is Ser, Arg, Thr, Ala, Tyr, Phe, or Trp, $X^7$ is Tyr, Gly, Arg, Ala, Asn, Asp, His, or Asn, $X^8$ is Tyr, Thr, Ser, or His, $X^9$ is Val, Ser, Ala, Phe, Pro, or absent, $X^{10}$ is Met, Gly, Asp, Pro, Val, or absent, $X^{11}$ is Asp, Tyr, Ser, Gly, Phe, or absent, $X^{12}$ is Val, Asp, Phe, or absent, $X^{13}$ is Phe, Asp, or absent, $X^{14}$ is Phe, Tyr, or absent, $X^{15}$ is Asp or absent, $X^{16}$ is Tyr or absent; a LCDR1 sequence comprising the formula $X^1-X^2-X^3-X^4-X^5-X^6-X^7-X^8-X^9-X^{10}-X^{11}-X^{12}$ (SEQ ID NO: 389), wherein $X^1$ is Gln, $X^2$ is Gly, Ser, or Asp, $X^3$ is Ile or Val, $X^4$ is Ser, Leu, Asn, or Gly, $X^5$ is Asn, Tyr, Gly, or Ser, $X^6$ is Tyr, Ser, Phe, or Trp, $X^7$ is Ser or absent, $X^8$ is Asn or absent, $X^9$ is Asn or absent, $X^{10}$ is Lys or absent, $X^{11}$ is Gln or absent, $X^{12}$ is Tyr or absent; a LCDR2 sequence comprising the formula $X^1-X^2-X^3$ (SEQ ID NO: 390), wherein $X^1$ is Ala, Trp, Asp, Tyr, Lys, Gly, or Ser, $X^2$ is Ala or Thr, and $X^3$ is Ser; and a LCDR3 sequence comprising the formula $X^1$-$X^2$-$X^3$-$X^4$-$X^5$-$X^6$-$X^7$-$X^8$-$X^9$ (SEQ ID NO: 391), wherein $X^1$ is Gln, Leu, or His, $X^2$ is Lys, Gln, or His, $X^3$ is Tyr, Ser, or Leu, $X^4$ is Tyr, Asn, Gly, Asp, or Ser, $X^5$ is Ser, Asp, or Asn, $X^6$ is Leu, Ala, Tyr, Thr, or Phe, $X^7$ is Pro or Arg, $X^8$ is Leu, Phe, Tyr, or Thr and $X^9$ is Thr or absent.

In one embodiment, the invention features a human antibody or antigen-binding fragment specific for Fel d1, comprising a HCVR encoded by nucleotide sequence segments derived from $V_H$, $D_H$ and $J_H$ germline sequences, and a LCVR encoded by nucleotide sequence segments derived from $V_K$ and $J_K$ germline sequences, with combinations as shown in Table 2.

The invention encompasses antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

A second aspect provides an isolated antibody or antigen-binding fragment thereof that competes for specific binding to Fel d1 with an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370 and 460; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378 and 468.

One embodiment provides an isolated antibody or antigen-binding fragment thereof that competes for specific binding to Fel d1 with an antibody or antigen-binding fragment comprising the complementarity determining regions (CDRs) of a heavy chain variable region (HCVR), wherein the HCVR has an amino acid sequence selected from the group consisting of SEQ ID NOs: 18, 66, 130, 162, 242, 306, 322, 370 and 460; and the CDRs of a light chain variable region (LCVR), wherein the LCVR has an amino acid sequence selected from the group consisting of SEQ ID NOs: 26, 74, 138, 170, 250, 314, 330, 378 and 468.

In a related embodiment, the invention provides an isolated antibody or antigen-binding fragment thereof that competes for specific binding to Fel d1 with an antibody or antigen-binding fragment comprising the heavy and light chain CDRs contained within heavy and light chain sequence pairs selected from the group consisting of SEQ ID NOs: 18/26, 66/74, 130/138, 162/170, 242/250, 306/314, 322/330, 370/378 and 460/468.

A third aspect provides an isolated antibody or antigen-binding fragment thereof that binds the same epitope on Feld 1 as an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370 and 460; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378 and 468.

One embodiment provides an isolated antibody or antigen-binding fragment thereof that binds the same epitope on Fel d1 as an antibody or antigen-binding fragment comprising the complementarity determining regions (CDRs) of a heavy chain variable region (HCVR), wherein the HCVR has an amino acid sequence selected from the group consisting of SEQ ID NOs: 18, 66, 130, 162, 242, 306, 322, 370 and 460; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378 and 468.

In a related embodiment, the invention provides an isolated antibody or antigen-binding fragment thereof that binds the same epitope on Fel d1 as an antibody or antigen-binding fragment comprising the heavy and light chain CDRs contained within heavy and light chain sequence pairs selected from the group consisting of SEQ ID NOs: 18/26, 66/74, 130/138, 162/170, 242/250, 306/314, 322/330, 370/378 and 460/468.

A fourth aspect provides for a bi-specific antigen-binding molecule that specifically binds Fel d1, which comprises two antigen-binding domains (two arms) that comprise an HCVR amino acid sequence and a LCVR amino acid sequence from any two or more antibodies described herein.

In one embodiment, the bi-specific antigen-binding molecule comprises a first antigen-binding domain that comprises a HCVR amino acid sequence as set forth in SEQ ID NO: 370 and a LCVR amino acid sequence as set forth in SEQ ID NO: 378, and a second antigen-binding domain that comprises a HCVR amino acid sequence as set forth in SEQ ID NO: 18 and a LCVR amino acid sequence as set forth in SEQ ID NO: 378.

In one embodiment, the bi-specific antigen-binding molecule comprises a first antigen-binding domain that comprises three heavy chain complementarity determining regions (HCDR1, HCDR2 and HCDR3) consisting of the amino acid sequences as set forth in SEQ ID NOs: 372, 374 and 376, respectively, and three light chain complementarity determining regions (LCDR1, LCDR2 and LCDR3) consisting of the amino acid sequences as set forth in SEQ ID NOs: 380, 382 and 384, respectively; and wherein the second antigen-binding domain comprises three heavy chain complementarity determining regions (HCDR1, HCDR2 and HCDR3) consisting of the amino acid sequences as set forth in SEQ ID NOs: 20, 22 and 24, respectively, and three light chain complementarity determining regions (LCDR1, LCDR2 and LCDR3) consisting of the amino acid sequences as set forth in SEQ ID NOs: 380, 382 and 384, respectively.

In one embodiment, the bi-specific antigen-binding molecule comprises a first antigen-binding domain that comprises a HCVR amino acid sequence as set forth in SEQ ID NO: 306 and a LCVR amino acid sequence as set forth in SEQ ID NO: 314, and a second antigen-binding domain that comprises a HCVR amino acid sequence as set forth in SEQ ID NO: 18 and a LCVR amino acid sequence as set forth in SEQ ID NO: 314.

In one embodiment, the bi-specific antigen-binding molecule comprises three heavy chain complementarity determining regions (HCDR1, HCDR2 and HCDR3) consisting of the amino acid sequences as set forth in SEQ ID NOs: 308, 310 and 312, respectively, and three light chain complementarity determining regions (LCDR1, LCDR2 and LCDR3) consisting of the amino acid sequences as set forth in SEQ ID NOs: 316, 318 and 320, respectively; and wherein the second antigen-binding domain comprises three heavy chain complementarity determining regions (HCDR1, HCDR2 and HCDR3) consisting of the amino acid sequences as set forth in SEQ ID NOs: 20, 22 and 24, respectively, and three light chain complementarity determining regions (LCDR1, LCDR2 and LCDR3) consisting of the amino acid sequences as set forth in SEQ ID NOs: 316, 318 and 320, respectively.

In one embodiment, the invention provides for an isolated antibody specific for Fel d1, or an antigen-binding fragment thereof that competes for binding to Fel d1 with any one of the bi-specific antigen-binding molecules of the invention.

In one embodiment, the invention provides for an isolated antibody specific for Fel d1, or an antigen-binding fragment thereof that binds to the same epitope on Fel d1 as any of the bi-specific antigen-binding molecules of the invention.

In one embodiment, the bi-specific antigen-binding molecule is an isolated human monoclonal antibody that binds specifically to Fel d1.

In one embodiment, the bi-specific antigen-binding molecule is an isolated human monoclonal antibody that binds specifically to Fel d1, wherein the human monoclonal antibody is a mono-specific antibody or a bi-specific antibody.

In one embodiment, the invention provides for a pharmaceutical composition comprising at least one bi-specific antigen-binding molecule as described herein and a pharmaceutically acceptable carrier or diluent.

In one embodiment, the invention provides for a method for treating a patient who demonstrates a sensitivity to, or an allergic reaction against, a cat, cat dander, cat hair or an extract thereof, or to Fel d1 protein, or for treating at least one symptom or complication associated with a sensitivity to, or an allergic reaction against, a cat, cat dander, cat hair or an extract thereof, or to Fel d1 protein, comprising administering an effective amount of one or more of the bi-specific antigen-binding molecules of the invention, or a pharmaceutical composition comprising an effective amount of one or more of the bi-specific antigen-binding molecules of the invention, to a patient in need thereof, wherein the patient demonstrates a reduced sensitivity to, or a diminished allergic reaction against a cat, cat dander, cat hair or an extract thereof, or to Fel d1 protein, or does not experience any sensitivity to, or allergic reaction to a cat, cat dander, cat hair or an extract thereof, or to Fel d1 protein, or wherein the patient demonstrates a reduction in at least one symptom or complication associated with a sensitivity to, or an allergic reaction against, a cat, cat dander, cat hair or an extract thereof, or to Fel d1 protein, or a reduction in the frequency and/or duration of at least one symptom or complication associated with a sensitivity to, or an allergic reaction against, a cat, cat dander, cat hair or an extract thereof, or to Fel d1 protein following administration of the bi-specific antigen-binding molecules or a composition comprising the bi-specific antigen-binding molecules of the invention.

In one embodiment, the invention provides for administering an effective amount of a second therapeutic agent along with at least one bi-specific antigen-binding molecule of the invention useful for diminishing an allergic reaction to a cat, cat dander, or to Fel d1 protein. The second therapeutic agent may be selected from the group consisting of a corticosteroid, a bronchial dilator, an antihistamine, epinephrine, a decongestant, a corticosteroid, another different antibody to Fel d1 and a peptide vaccine.

In one embodiment, the treatment with one or more bi-specific antigen-binding molecules of the invention alone, or in combination with a second therapeutic agent, may result in a reduction in allergic rhinitis, allergic conjunctivitis, allergic asthma, or an anaphylactic response following exposure of the patient to a cat, cat dander or to Fel d1 protein.

In a fifth aspect, the invention provides nucleic acid molecules encoding Fel d1 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, 321, 337, 353, 369 and 459, or a substantially identical sequence having at least 90%, at least 95%, at least 98%, or at least 99% homology thereof.

In one embodiment, the HCVR is encoded by a nucleic acid sequence selected from the group consisting of SEQ ID NO: 17, 65, 129, 161, 241, 305, 321, 369 and 459.

In one embodiment, the antibody or fragment thereof further comprises a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, 345, 361, 377 and 467 or a substantially identical sequence having at least 90%, at least 95%, at least 98%, or at least 99% homology thereof.

In one embodiment, the LCVR is encoded by a nucleic acid sequence selected from the group consisting of SEQ ID NO: 25, 73, 137, 169, 249, 313, 329, 377 and 467.

In one embodiment, the invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, 343, 359, 375 and 465, or a substantially similar sequence thereof having at least 90%, at least 95%, at least 98% or at least 99% sequence identity; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351, 367, 383 and 473, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339, 355, 371 and 461, or a substantially similar sequence thereof having at least 90%, at least 95%, at least 98% or at least 99% sequence identity; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, 341, 357, 373 and 463, or a substantially similar sequence thereof having at least 90%, at least 95%, at least 98% or at least 99% sequence identity; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347, 363, 379 and 469, or a substantially similar sequence thereof having at least 90%, at least 95%, at least 98% or at least 99% sequence identity; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, 349, 365, 381 and 471, or a substantially similar sequence thereof having at least 90%, at least 95%, at least 98% or at least 99% sequence identity.

A sixth aspect provides a pharmaceutical composition comprising a therapeutically effective amount of one or more isolated human antibodies or antigen-binding fragments thereof that specifically bind Fel d1, together with one or more pharmaceutically acceptable excipients.

In one embodiment, the pharmaceutical composition comprises a therapeutically effective amount of two or more isolated human antibodies or antigen-binding fragments thereof that specifically bind Fel d1 together with one or more pharmaceutically acceptable excipients.

In one embodiment, the pharmaceutical composition comprises:
a) an isolated first fully human monoclonal antibody, or antigen-binding fragment thereof that specifically binds Fel d1, which comprises a HCVR having an amino acid sequence as set forth is SEQ ID NO: 18; and a LCVR having an amino acid sequence as set forth is SEQ ID NO: 26; and
b) an isolated second fully human monoclonal antibody, or antigen-binding fragment thereof that specifically binds Fel d1, which comprises a HCVR having an amino acid sequence selected from the group consisting of SEQ ID NOs: 66, 130, 162, 306, 322, 370 and 460; and a LCVR having an amino acid sequence selected from the group consisting of SEQ ID NOs: 74, 138, 170, 314, 330, 378 and 468.

In one embodiment, the pharmaceutical composition comprises:
a) an isolated first fully human monoclonal antibody, or antigen-binding fragment thereof that specifically binds Fel d1, which comprises a HCVR having an amino acid sequence as set forth is SEQ ID NO: 242; and a LCVR having an amino acid sequence as set forth is SEQ ID NO: 250; and
b) an isolated second fully human monoclonal antibody, or antigen-binding fragment thereof that specifically binds Fel d1, which comprises a HCVR having an amino acid sequence selected from the group consisting of SEQ ID NOs: 306, 322 and 460; and a LCVR having an amino acid sequence selected from the group consisting of SEQ ID NOs: 314, 330 and 468.

In one embodiment, the pharmaceutical composition comprises:
a) an isolated first fully human monoclonal antibody or antigen-binding fragment thereof that specifically binds Fel d1, comprising a HCVR/LCVR amino acid sequence pair consisting of SEQ ID NOs: 18/26; and
b) an isolated second fully human monoclonal antibody or antigen-binding fragment thereof that specifically binds Fel d1, comprising a HCVR/LCVR amino acid sequence pair selected from the group consisting of SEQ ID NOs: 66/74, 130/138, 162/170, 306/314, 322/330 370/378 and 460/468.

In one embodiment, the pharmaceutical composition comprises:
a) an isolated first human monoclonal antibody or antigen-binding fragment thereof that binds specifically to Fel d1, comprising a HCVR/LCVR amino acid sequence pair consisting of SEQ ID NOs: 18/26; and
b) an isolated second human monoclonal antibody or antigen-binding fragment thereof that binds specifically to Fel d1, comprising a HCVR/LCVR amino acid sequence pair consisting of SEQ ID NOs: 130/138.

In one embodiment, the pharmaceutical composition comprises:
a) an isolated first human monoclonal antibody or antigen-binding fragment thereof that binds specifically to Fel d1, comprising a HCVR/LCVR amino acid sequence pair consisting of SEQ ID NOs: 18/26; and
b) an isolated second human monoclonal antibody or antigen-binding fragment thereof that binds specifically to Fel d1, comprising a HCVR/LCVR amino acid sequence pair consisting of SEQ ID NOs: 322/330.

In one embodiment, the pharmaceutical composition comprises:
a) an isolated first human monoclonal antibody or antigen-binding fragment thereof that binds specifically to Fel d1, comprising a HCVR/LCVR amino acid sequence pair consisting of SEQ ID NOs: 18/26; and
b) an isolated second human monoclonal antibody or antigen-binding fragment thereof that binds specifically to Fel d1, comprising a HCVR/LCVR amino acid sequence pair consisting of SEQ ID NOs: 306/314.

In one embodiment, the pharmaceutical composition comprises:
a) an isolated first human monoclonal antibody or antigen-binding fragment thereof that binds specifically to Fel d1, comprising a HCVR/LCVR amino acid sequence pair consisting of SEQ ID NOs: 18/26; and
b) an isolated second human monoclonal antibody or antigen-binding fragment thereof that binds specifically to Fel d1, comprising a HCVR/LCVR amino acid sequence pair consisting of SEQ ID NOs: 370/378.

In one embodiment, the pharmaceutical composition comprises:
a) an isolated first fully human monoclonal antibody or antigen-binding fragment thereof that specifically binds Fel d1, comprising a HCVR/LCVR amino acid sequence pair consisting of SEQ ID NOs: 242/250; and
b) an isolated second fully human monoclonal antibody or antigen-binding fragment thereof that specifically binds Fel d1, comprising a HCVR/LCVR amino acid sequence pair selected from the group consisting of SEQ ID NOs: 306/314 and 322/330.

In one embodiment, the pharmaceutical composition comprises
a) an isolated first human monoclonal antibody or antigen-binding fragment thereof that binds specifically to Fel d1, comprising a HCVR/LCVR amino acid sequence pair consisting of SEQ ID NOs: 242/250; and
b) an isolated second human monoclonal antibody or antigen-binding fragment thereof that binds specifically to Fel d1, comprising a HCVR/LCVR amino acid sequence pair consisting of SEQ ID NOs: 306/314.

In one embodiment, the pharmaceutical composition comprises
a) an isolated first human monoclonal antibody or antigen-binding fragment thereof that binds specifically to Fel d1, comprising a HCVR/LCVR amino acid sequence pair consisting of SEQ ID NOs: 242/250; and
b) an isolated second human monoclonal antibody or antigen-binding fragment thereof that binds specifically to Fel d1, comprising a HCVR/LCVR amino acid sequence pair consisting of SEQ ID NOs: 322/330.

In one embodiment, the pharmaceutical composition comprises two or more isolated human monoclonal antibodies that bind specifically to Fel d1, or antigen-binding fragments thereof, comprising HCVR/LCVR amino acid sequence pairs selected from the group consisting of SEQ ID NOs: 18/26, 66/74, 130/138, 162/170, 242/250, 306/314, 322/330, 370/378 and 460/468.

In one embodiment, the pharmaceutical composition comprises four isolated human monoclonal antibodies that bind specifically to Fel d1, or antigen-binding fragments thereof, wherein the human antibodies or antigen-binding fragments thereof comprise the HCVR/LCVR amino acid sequence pairs of SEQ ID NOs: 18/26, 66/74, 130/138 and 162/170.

In one embodiment, the invention features a composition, which is a combination of a therapeutically effective amount of one or more anti-Fel d1 antibodies or antigen-binding fragments thereof of the invention, and a therapeutically effective amount of a second therapeutic agent.

The second therapeutic agent may be a small molecule drug, a protein/polypeptide, an antibody, a nucleic acid molecule, such as an anti-sense molecule, or a siRNA. The second therapeutic agent may be synthetic or naturally derived.

The second therapeutic agent may be any agent that is advantageously combined with an antibody or fragment thereof of the invention, for example, a second antibody other than those described herein that is capable of blocking the binding of Fel d1 to IgE present on mast cells or basophils. A second therapeutic agent may also be any agent that is used as standard of care in treating an allergic response to any allergen. Such second therapeutic agent may be an antihistamine, epinephrine, a decongestant, a corticosteroid, or a peptide vaccine.

In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

When multiple therapeutics are co-administered, dosages may be adjusted accordingly, as is recognized in the pertinent art.

A seventh aspect provides a method for treating a patient who demonstrates a sensitivity to, or an allergic reaction against, a cat, cat dander, cat hair extract, or to Fel d1 protein, or for treating at least one symptom or complication associated with a sensitivity to, or allergic reaction against a cat, cat dander, cat hair extract, or to Fel d1 protein, comprising administering an effective amount of one or more isolated human monoclonal antibodies or antigen-binding fragments thereof that bind specifically to Fel d1, or a pharmaceutical composition comprising an effective amount of one or more isolated human monoclonal antibodies or fragments thereof that binds specifically to Fel d1, or an effective amount of one or more of the bi-specific antigen-binding molecules that specifically binds Fel d1, or a pharmaceutical composition comprising an effective amount of one or more of the bi-specific antigen-binding molecules that specifically binds to Fel d1, to a patient in need thereof, wherein the sensitivity to, or an allergic reaction against, a cat, cat dander, cat hair extract, or to Fel d1 protein is either prevented, or lessened in severity and/or duration, or at least one symptom or complication associated with the sensitivity to, or allergic reaction against, a cat, cat dander, cat hair extract, or to Fel d1 protein is prevented, or ameliorated, or that the frequency and/or duration of, or the severity of the sensitivity to or allergic reaction against, a cat, cat dander, cat hair extract, or to Fel d1 protein is reduced following administration of one or more of the isolated human monoclonal antibodies or fragments thereof that bind specifically to Fel d1, or following administration of one or more of the bi-specific antigen-binding molecules that specifically binds Fel d1, or following administration of a composition comprising any one or more of the foregoing antibodies or bi-specific antigen-binding molecules.

In one embodiment, the invention provides a pharmaceutical composition comprising one or more of the antibodies of the invention, or one or more of the bi-specific antigen-binding molecules that binds specifically to Fel d1 for use in treating a patient who demonstrates a sensitivity to, or an allergic reaction against, a cat, cat dander, cat hair extract, or to Fel d1 protein, or for treating at least one symptom or complication associated with a sensitivity to, or allergic reaction against a cat, cat dander, cat hair extract, or to Fel d1 protein, wherein the sensitivity to, or an allergic reaction against, a cat, cat dander, cat hair extract, or to Fel d1 protein is either prevented, or lessened in severity and/or duration, or at least one symptom or complication associated with the sensitivity to, or allergic reaction against, a cat, cat dander, cat hair extract, or to Fel d1 protein is prevented, or ameliorated, or that the frequency and/or duration of, or the severity of the sensitivity to or allergic reaction against, a cat, cat dander, cat hair extract, or to Fel d1 protein is reduced.

In one embodiment, the invention provides for use of a pharmaceutical composition comprising one or more of the antibodies of the invention, or one or more of the bi-specific antigen-binding molecules that binds specifically to Fel d1 in the manufacture of a medicament for use in treating a patient who demonstrates a sensitivity to, or an allergic reaction against, a cat, cat dander, cat hair extract, or to Fel d1 protein, or for treating at least one symptom or complication associated with a sensitivity to, or allergic reaction against a cat, cat dander, cat hair extract, or to Fel d1 protein, wherein the sensitivity to, or an allergic reaction against, a cat, cat dander, cat hair extract, or to Fel d1 protein is either prevented, or lessened in severity and/or duration, or at least one symptom or complication associated with the sensitivity to, or allergic reaction against, a cat, cat dander, cat hair extract, or to Fel d1 protein is prevented, or ameliorated, or that the frequency and/or duration of, or the severity of the sensitivity to or allergic reaction against, a cat, cat dander, cat hair extract, or to Fel d1 protein is reduced.

In one embodiment, the invention provides use of a pharmaceutical composition as described above, wherein the composition is administered in combination with a second therapeutic agent useful for diminishing an allergic reaction to a cat, cat dander, cat hair extract, or to Fel d1 protein. In one embodiment, the invention provides for use of the pharmaceutical composition as described above, wherein the second therapeutic agent is selected from a corticosteroid, a bronchial dilator, an antihistamine, epinephrine, a decongestant, another different antibody to Fel d1 and a peptide vaccine.

In certain embodiments, the antibodies of the invention, or the bi-specific antigen-binding molecules that bind specifically to Fel d1 may be capable of reducing, minimizing, or preventing at least one symptom in a patient sensitive to the Fel d1 cat allergen, such as sneezing, congestion, nasal blockage, coughing, wheezing, bronchoconstriction, rhinitis, or conjunctivitis.

In one embodiment, the antibodies of the invention, or the bi-specific antigen-binding molecules that bind specifically to Fel d1, or a composition comprising one or more antibodies of the invention or one or more of the antigen-binding molecules that bind specifically to Fel d1 may be used to prevent more serious in vivo complications associated with an allergy to Fel d1, including asthmatic responses, anaphylactic shock, or even death resulting from anaphylaxis.

In one embodiment, the pharmaceutical composition is administered to the patient in combination with a second therapeutic agent.

In another embodiment, the second therapeutic agent is selected from the group consisting of an antihistamine, epinephrine, a decongestant, a corticosteroid, another different antibody to Fel d1, a peptide vaccine and any other palliative therapy useful for reducing the severity of the allergic reaction or for ameliorating at least one symptom associated with the allergic reaction.

Other embodiments will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described. All publications mentioned herein are incorporated herein by reference in their entirety.
Definitions The term "Fel d1" or "FELD1", as used herein, refers to at least one Fel d1 protein, either in natural/native form, or recombinantly produced. The Fel d1 protein comprises, or alternatively consists of, chain 1 (also referred to as chain A) of Fel d1 (SEQ ID NO: 392) and chain 2 (also referred to as chain B) of Fel d1 (SEQ ID NO: 393). The natural Fel d1 protein is an approximately 18 kDa heterodimeric glycoprotein composed of two chains derived from two independent genes (See Duffort, O. A. et al., (1991), Mol. Immunol. 28:301-309; Kristensen, A. K. et al., (1997), Biol. Chem. 378:899-908; Kaiser L. et al. (2003), J. Biol. Chem. 278 (39):37730-37735). A recombinantly produced Fel d1 protein is also shown as SEQ ID NO: 396, wherein this sequence contains amino acid residues 18 through 109 of Fel d1 chain B from GenBank accession number NP_001041619.1 (without the signal sequence) fused in line with amino acid residues 19-88 of chain A of Fel d1 from GenBank accession number NP_001041618.1 (without the signal sequence and with a D27G mutation, which corresponds to the glycine at position 101 of SEQ ID NO: 396). Other recombinantly produced Fel d1 constructs of the invention are exemplified in SEQ ID NOs: 385, 394, 395 and 397.

"Chain 1", or "chain A" of Fel d1 is a polypeptide comprising, or alternatively consisting of, an amino acid sequence of SEQ ID NO: 392, or a homologous sequence thereof. The term homologous sequence of SEQ ID NO:392, as used herein, refers to a polypeptide that has an identity to SEQ ID NO:392 which is greater than 70%, preferably greater than 80%, more preferably greater than 90%, and even more preferably greater than 95%. The amino acid sequence of chain 1 of Fel d1 is also provided in GenBank as accession number P30438, or as accession number NP_001041618.1, which also include the signal peptide which is removed in the mature protein.

"Chain 2", or "chain B" of Fel d1 is a polypeptide comprising, or alternatively consisting of, an amino acid sequence of SEQ ID NO: 393, or a homologous sequence thereof. The term homologous sequence of SEQ ID NO: 393, as used herein, refers to a polypeptide that has an identity to SEQ ID NO:393 which is greater than 70%, preferably greater than 80%, more preferably greater than 90%, and even more preferably greater than 95%. The amino acid sequence of chain 2 of Fel d1 is also provided in GenBank as accession number P30440, or as accession number NP_001041619.1, which include the signal peptide which is removed in the mature protein.

The term "Fel d1 fragment" as used herein, refers to a polypeptide comprising or alternatively consisting of, at least one antigenic site of Fel d1. In one embodiment, the term "Fel d1 fragment" as used herein, refers to a polypeptide comprising or alternatively consisting of at least two antigenic sites of Fel d1. In one embodiment, the antigenic sites are covalently linked. In one embodiment, the antigenic sites are linked by at least one peptide bond. In one embodiment, the two antigenic sites are linked by at least one peptide bond and a spacer between the antigenic sites. In one embodiment, the at least two antigenic sites derive from both chain 1 of Fel d1 and from chain 2 of Fel d1. In one embodiment, the at least two antigenic sites comprise amino acid sequences 23-92 of GenBank accession number P30438 and amino acid sequences 18-109 of GenBank accession number P30440. In one embodiment, the at least two antigenic sites derive from both chain 1 of Fel d1 and from chain 2 of Fel d1. In one embodiment, the at least two antigenic sites comprise amino acid sequences 19-88 of GenBank accession number NP_001041618.1 and amino acid sequences 18-109 of GenBank accession number NP_001041619.1. In one embodiment, the at least two antigenic sites comprise an amino acid sequence within any of SEQ ID NOs: 385, 394, 395, 396 or 397. In one embodiment, any of the Fel d1 fragments are capable of inducing the production of antibodies in vivo that specifically bind to naturally occurring Fel d1, or to recombinantly produced Fel d1.

The term "antibody", as used herein, means any antigen-binding molecule or molecular complex comprising at least one complementarity determining region (CDR) that specifically binds to or interacts with a particular antigen (e.g., Fel d1). The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. (2002), J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human monoclonal antibodies that specifically bind to Fel d1, as disclosed herein, may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human monoclonal antibodies comprising variants of any of the HCVR, LCVR, and/or CDR amino acid sequences disclosed herein having one or more conservative substitutions. For example, the present invention includes antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bi-specific antigen-binding molecule" means a protein, polypeptide or molecular complex comprising at least a first antigen-binding domain and a second antigen-binding domain (i.e. two arms). Each antigen-binding domain within the bi-specific antigen-binding molecule comprises at least one CDR that alone, or in combination with one or more additional CDRs and/or FRs, specifically binds to a particular antigen. In the context of the present invention, the first antigen-binding domain specifically binds a first antigen on Fel d1 and the second antigen-binding domain specifically binds a second, distinct antigen on Fel d1.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to Fel d1. Moreover, multi-specific antibodies that bind to Fel d1 and one or more additional antigens or a bi-specific that binds to two different regions of Fel d1 (for example, chain 1 and/or chain 2 of Fel d1) are nonetheless considered antibodies that "specifically bind", as used herein.

The term "high affinity" antibody refers to those mAbs having a binding affinity to Fel d1, expressed as $K_D$, of at least $10^{-8}$ M; preferably $10^{-9}$M; more preferably $10^{-10}$M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from Fel d1, with a rate constant of $1 \times 10^{-3}$ s$^{-1}$ or less, preferably $1 \times 10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to bind to Fel d1.

The specific embodiments, antibody or antibody fragments of the invention may be conjugated to a therapeutic moiety ("immunoconjugate"), such as a corticosteroid, a second anti-Fel d1 antibody, or epinephrine, a vaccine, or any other therapeutic moiety useful for treating an allergic response to Fel d1.

An "isolated antibody", as used herein, is intended to refer to an antibody that is substantially free of other antibodies (Abs) having different antigenic specificities (e.g., an isolated antibody that specifically binds Fel d1, or a fragment thereof, is substantially free of Abs that specifically bind antigens other than Fel d1.

A "blocking antibody" or a "neutralizing antibody", as used herein (or an "antibody that neutralizes Fel d1 activity"), is intended to refer to an antibody, or an antigen binding portion thereof, whose binding to Fel d1 results in inhibition of at least one biological activity of Fel d1. For example, an antibody of the invention may aid in preventing the primary allergic response to Fel d1. Alternatively, an antibody of the invention may demonstrate the ability to prevent a secondary allergic response to Fel d1, or at least one symptom of an allergic response to Fel d1, including sneezing, coughing, an asthmatic condition, or an anaphylactic response caused by Fel d1. This inhibition of the biological activity of Fel d1 can be assessed by measuring one or more indicators of Fel d1 biological activity by one or more of several standard in vitro or in vivo assays (such as a passive cutaneous anaphylaxis assay, as described herein) or other in vivo assays known in the art (for example, other animal models to look at protection from challenge with Fel d1 following administration of one or more of the antibodies described herein).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be either linear or conformational. A linear epitope is one produced by adjacent amino acid residues in a polypeptide chain. A conformational epitope is produced by spatially juxtaposed amino acids from different segments of the linear polypeptide chain. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes may also be defined as structural or functional. Functional epitopes are generally a subset of the structural epitopes and have those residues that directly contribute to the affinity of the interaction. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

In specific embodiments, the antibody or antibody fragment for use in the method of the invention may be monospecific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The antibodies of the invention may be used to "desensitize" a cat-sensitive individual. The term to "desensitize" is defined herein as to decrease the allergic-reactivity of a cat-sensitive individual to exposure to cats, cat dander or products thereof, e.g. Fel d1 (to a level less than that which the cat-sensitive individual would otherwise experience).

General Description

The domestic cat is a source of many indoor allergens and the severity of the symptoms in individuals who demonstrate a sensitivity to cat allergens ranges from a relatively mild rhinitis and conjunctivitis to a potentially life-threatening asthmatic condition (Lau, S. et al. (2000), Lancet 356:1392-1397). While patients who demonstrate such a sensitivity to cats appear to be responsive to different molecules found in cat dander and pelts, the major allergen appears to be Fel d1 (*Felis domesticus* allergen 1). It has been shown that greater than 80% of patients who are allergic to cats have IgE antibodies to this allergen (van Ree, R. et al. (1999), J. Allergy Clin. Immunol 104:1223-1230).

The Fel d1 protein is an approximately 18 kDa heterodimeric acidic glycoprotein that contains about 10-20% of N-linked carbohydrates. Each heterodimer comprises two polypeptide chains that are encoded by two separate genes (Duffort, O A, et al., (1991), Mol. Immunol. 28:301-309; Morgenstern, J P, et al., (1991), PNAS 88:9690-9694; Griffith, I. J., et al. (1992), Gene 113:263-268). Chain 1 comprises about 70 amino acid residues and chain 2 comprises about 90-92 amino acid residues. Three interchain disulfide bonds linking the two chains in natural Fel d1 have been proposed (Kristensen, A. K. et al. (1997), Biol. Chem. 378:899-908) and confirmed for recombinant Fel d1 in the crystal structure (Kaiser, L. et al. (2003), J. Biol. Chem. 278:37730-37735; Kaiser, L. et al., (2007), J. Mol. Biol. 370:714-727). Although each chain is sometimes individually referred to as "Fel d 1", both chains are needed for the full protein allergen.

Fel d1 is produced by sebaceous glands, squamous glands and squamous epithelial cells and is transferred to the pelt by licking and grooming (Bartholome, K. et al. (1985), J. Allergy Clin. Immunol. 76:503-506; Charpin, C. et al. (1991), J. Allergy Clin. Immunol. 88:77-82; Dabrowski, A. J. (1990), et al. J. Allergy Clin. Immunol. 86:462-465). It is also present in the salivary, perianal and lachrymal glands (Andersen, M. C., et al. (1985), J. Allergy Clin. Immunol. 76:563-569; van Milligen, F. J. et al., (1992), Int. Arch. Allergy Appl. Immunol. 92:375-378) and the principal reservoirs appear to be the skin and the fur (Mata, P. et al. (1992), Ann. Allergy 69(4):321-322).

The Fel d1 protein is of an unknown function to the animal but causes an IgG or IgE reaction in sensitive humans (either as an allergic or asthmatic response). Although other cat allergens are known, including Fel d2 (albumin) and Fel d3 (cystatin), 60% to 90% of the anti-cat IgE produced is directed against Fel d1 (Leitermann, K. et al., (1984), J Allergy Clin. Immunol. 74:147-153; Lowenstein, H. et al., (1985), Allergy 40:430-441; van Ree, R. et al., (1999), J. Allergy Clin. Immunol. 104:1223-1230; Ichikawa, K. et al., (2011), Clin. Exp. Allergy, 31:1279-1286).

Immunoglobulin E (IgE) is responsible for type 1 hypersensitivity, which manifests itself in allergic rhinitis, allergic conjunctivitis, hay fever, allergic asthma, bee venom allergy, and food allergies. IgE circulates in the blood and binds to high-affinity Fc receptors for IgE on basophils and mast cells. In most allergic responses, the allergens enter the body through inhalation, ingestion, or through the skin. The allergen then binds to preformed IgE already bound to the high affinity receptor on the surfaces of mast cells and basophils, resulting in cross-linking of several IgE molecules and triggering the release of histamine and other inflammatory mediators causing the various allergic symptoms.

The treatment for cat allergies includes desensitization therapy, which involves repeated injections with increasing dosages of either a crude cat dander extract, or short peptides derived from Fel d1. Using the crude extract of cat dander, Lilja et. al. demonstrated that after three years of such treatment, patients allergic to cats still exhibited systemic symptoms (Lilja, Q. et al. (1989), J. Allergy Clin. Immunol. 83:37-44 and Hedlin, et al. (1991), J. Allergy Clin. Immunol. 87:955-964). Using short peptides derived from Fel d1 for desensitization resulted in a non-significant difference between the peptide group and the placebo control group (Oldfield, W. L. et al., (2002), Lancet, 360:47-53). Efficacy was only observed when large amounts (750 ug) of the short peptide were administered to patients (Norman, P. S. et al. (1996), Am. J. Respir. Crit. Care Med. 154:1623-1628). Furthermore, asthmatic reactions have been reported in patients given both crude extracts from cat dander, as well as in patients given short Fel d1 peptide treatment. Accordingly, there is a need in the field of cat allergy treatment for alternative strategies for treating patients sensitive to cat allergens, in particular Fel d1.

Antibodies have been proposed as a general treatment strategy for allergies, since they may be able to block the entry of allergenic molecules into the mucosal tissues, or may bind the allergen before it has the opportunity to bind to the IgE bound to the high affinity receptor on mast cells or basophils, thus preventing the release of histamine and other inflammatory mediators from these cells. U.S. Pat. No. 5,670,626 describes the use of monoclonal antibodies for the treatment of IgE-mediated allergic diseases such as allergic rhinitis, allergic asthma, and allergic conjunctivitis by blocking the binding of allergens to the mucosal tissue. U.S. Pat. No. 6,849,259 describes the use of allergen-specific antibodies to inhibit allergic inflammation in an in vivo mouse model of allergy. Milk-based and egg-based antibody systems have been described. For example, US20030003133A1 discloses using milk as a carrier for allergens for inducing oral tolerance to cat dander and other allergens. Compositions and methods for reducing an allergic response in an animal to an allergen in the environment through use of a molecule that inhibits the ability of the allergen to bind to mast cells was described in US2010/0143266. Other antibodies to Fel d1 were described by de Groot et. al. (de Groot et. al., (1988), J. Allergy Clin. Immunol. 82:778-786).

The fully human antibodies described herein demonstrate specific binding to Fel d1 and may be useful for treating patients suffering from cat allergies, in particular, in patients who demonstrate sensitivity to the Fel d1 allergen. The use of such antibodies may be an effective means of treating patients suffering from allergies to cat dander, or they may be used to prevent a heightened response to Fel d1 upon secondary exposure, or the accompanying symptoms associated with the allergy, or may be used to lessen the severity and/or the duration of the allergic response associated with a primary exposure to a cat harboring the Fel d1 allergen or with the recurrence of the symptoms upon secondary exposure. They may be used alone or as adjunct therapy with other therapeutic moieties or modalities known in the art for treating such allergies, such as, but not limited to, treatment with corticosteroids or epinephrine. They may be used in conjunction with a second or third different antibody specific for Fel d1. They may be used with allergen-specific immunotherapy (SIT).

In certain embodiments, the antibodies of the invention are obtained from mice immunized with a primary immunogen, such as natural Fel d1, which may be purchased commercially (See, for example, Indoor Biotech, #NA-FD1-2), or may be produced recombinantly. In certain embodiments, the immunogen may be either chain 1 of Fel d1, or chain 2 of Fel d1, or may be a combination of both chain 1 and chain 2 administered sequentially, or concurrently. The full-length amino acid sequence of chain 1 (also referred to as FELD1 A) is shown as SEQ ID NO: 392. Full-length amino acid sequences for chain 1 may also be found in GenBank accession numbers P30438 and NP_001041618.1. The full-length amino acid sequence of chain 2 (also referred to as FELD1 B) is shown as SEQ ID NO: 393. Full-length amino acid sequences for chain 2 may also be found in GenBank accession numbers PP30440 and NP_001041619.1.

In certain embodiments, the recombinantly produced Fel d1 immunogen may be made by direct fusion of the two chains of Fel d1, as described in Kaiser et. al., to produce a fusion product that has a similar refolding pattern to that of natural Fel d1 (Kaiser, L. et al., (2003), J. Biol. Chem. 278(39):37730-37735). In certain embodiments, the immunogen may be a fusion protein such as that shown in the constructs of SEQ ID NOs: 385, 394, 395, 396 or 397, followed by immunization with a secondary immunogen, or with an immunogenically active fragment of the natural or recombinantly produced Fel d1.

The immunogen may be a biologically active and/or immunogenic fragment of natural or recombinantly produced Fel d1, or DNA encoding the active fragment thereof. The fragment may be derived from either the N-terminal or C-terminal of either chain 1 or chain 2, or from the N terminal or the C terminal of both chain 1 and chain 2. Fragments may be obtained from any site within chain 1 or chain 2 to be used as an immunogen for preparing antibodies to Fel d1.

In certain embodiments, the immunogen may be a fusion protein comprising any one or more of the following: i) amino acid residues 18-109 of chain 2 of Fel d1 (See GenBank accession number P30440 and also SEQ ID NO: 393) fused via the C terminus directly with the N terminus of amino acid residues 23-92 of chain 1 of Fel d1 (See GenBank accession number P30438 and also SEQ ID NO: 392); ii) amino acid residues 23-92 of chain 1 of Fel d1 (See GenBank accession number P30438 and also SEQ ID NO: 392) fused via the C terminus to the N terminus of amino acid residues 18-109 of chain 2 of Fel d1 (See GenBank accession number P30440 and also SEQ ID NO: 393); iii) amino acid residues 18-109 of chain 2 of Fel d1 (See GenBank accession number NP_001041619.1) fused via the C terminus directly with the N terminus of amino acid residues 19-88 of chain 1 of Fel d1 (See GenBank accession number NP_001041618.1), such as the construct shown in SEQ ID NO: 394 or 396; iv) amino acid residues 19-88 of chain 1 of Fel d1 (See GenBank accession number NP_001041618.1) fused via the C terminus to the N terminus of amino acid residues 18-109 of chain 2 of Fel d1 (See GenBank accession number NP_001041619.1). See also SEQ ID NO: 395. In certain embodiments, the fusion protein may have a tag at the C terminal end of the construct, such as a myc-myc-hexahistidine tag (See SEQ ID NOs: 385, 396 or 397 for such constructs.). In related embodiments, the fusion protein may have a mouse antibody Fc region coupled at the C terminal end of the construct (See SEQ ID NOs: 394 or 395 for such constructs.). In certain embodiments, chains 1 and 2 are coupled via a linker known to those skilled in the art, e.g. $(G_4S)_3$ (See SEQ ID NOs: 395 and 397 for such a construct.).

In certain embodiments, antibodies that bind specifically to Fel d1 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation Fel d1 specific antibodies. In certain embodiments, any one or more of the above-noted regions of Fel d1, or fragments thereof may be used for preparing monospecific, bispecific, or multispecific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to either chain 1 and/or chain 2 of Fel d1. An antibody fragment may include a Fab fragment, a $F(ab')_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; $V_H$-$C_H2$; $V_H$-$C_H3$; (iv) $V_H$-$C_H1$-$C_H2$, (v) $V_H$-$C_H1$-$C_H2$-$C_H3$, (vi) $V_H$-$C_H2$-$C_H3$; (vii) $V_H$-$C_L$; $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to Fel d1.

Using VELOCIMMUNE™ technology (see, for example, U.S. Pat. No. 6,596,541, Regeneron Pharmaceuticals, VELOCIMMUNE®) or any other known method for generating monoclonal antibodies, high affinity chimeric antibodies to Fel d1 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-Fel d1 antibodies and antibody fragments of the present invention encompass proteins having amino acid sequences that vary from those of the described antibodies, but that retain the ability to bind Fel d1. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Biological Characteristics of the Antibodies

In general, the antibodies of the present invention may function by binding to either chain 1 or to chain 2 of Fel d1, or to both chain 1 and chain 2 of Fel d1 or to a fragment of either chain 1 or chain 2.

In certain embodiments, the antibodies of the present invention may bind to an epitope located in at least the C-terminal region of either chain 1 or chain 2 of Fel d1. In one embodiment, the antibodies may bind to an epitope within the N-terminal region of either chain 1 or chain 2 of Fel d1.

In certain embodiments, the antibodies of the present invention may function by blocking or inhibiting the binding of IgE to mast cells or basophils in a patient sensitive to the fel d1 allergen.

In certain embodiments, the antibodies of the present invention may function by binding to any other region or fragment of the full length chain 1 or chain 2 of the natural Fel d1 protein, the amino acid sequence of which is shown in SEQ ID NO: 392 (chain 1) and SEQ ID NO: 393 (chain 2).

In certain embodiments, the antibodies of the present invention may be bi-specific antibodies. The bi-specific antibodies of the invention may bind one epitope in chain 1 and may also bind one epitope in chain 2. In certain embodiments, the bi-specific antibodies of the invention may bind two different epitopes in chain 1. In certain embodiments, the bi-specific antibodies of the invention may bind two different epitopes in chain 2. In certain embodiments, the bi-specific antibodies of the invention may bind to two different sites within the same helix on either one of chain 1 or chain 2, or may bind to the same helix on both chain 1 and chain 2. The structure of Fel d1 is described in greater detail in Kaiser et. al. (Kaiser, L. et. al. (2003), J. Biol. Chem. 278 (39):37730-37735), whereby the authors note that Fel d1 consists of eight helices, H1-H4 and H5-H8, which correspond to chains 2 and 1, respectively, in natural Fel d1.

In one embodiment, the invention provides a fully human monoclonal antibody or antigen-binding fragment thereof that binds to chain 1 and/or chain 2 of Fel d1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354 and 370, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362 and 378, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360 and 376, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368 and 384, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356 and 372, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358 and 374, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364 and 380, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366 and 382, or a substantially similar sequence thereof having at least 90%, at least 95%, at least 98% or at least 99% sequence identity; (v) binds to chain 1 and/or chain 2 of Fel d1 with a $K_D$ equal to or less than $10^{-9}$; (vi) does not cross-react with, or bind to, uteroglobin; or (vii) blocks dye extravasation in vivo in a passive cutaneous anaphylaxis (PCA) mouse model using Fel d1 specific mouse IgE.

In one embodiment, the invention provides for the use of a combination of two or more fully human antibodies of the invention, or fragments thereof, for preparation of a composition, wherein the antibodies bind to chain 1 and/or chain 2 of Fel d1, and wherein each antibody or fragment thereof contained within the composition exhibits one or more of the following characteristics: (i) comprise a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354 and 370, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362 and 378, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360 and 376, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368 and 384, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356 and 372, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358 and 374, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364 and 380, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366 and 382, or a substantially similar sequence thereof having at least 90%, at least 95%, at least 98% or at least 99% sequence identity; (v) binds to chain 1 and/or chain 2 of Fel d1 with a $K_D$ equal to or less than $10^{-9}$; (vi) does not cross-react with, or bind to, uteroglobin; (vii) blocks dye extravasation in vivo in a passive cutaneous anaphylaxis (PCA) mouse model using Fel d1 specific mouse IgE; or (viii) when combined with a second antibody or antigen binding fragment thereof of the invention, decreases the frequency of mucous secreting cells in the lungs of Fel d1 challenged animals.

Certain Fel d1 antibodies of the present invention, when used alone, or in combination, are able to bind to and neutralize at least one biological effect of Fel d1, as determined by in vitro or in vivo assays. The ability of the antibodies of the invention to bind to and neutralize the activity of Fel d1 may be measured using any standard method known to those skilled in the art, including binding assays, or neutralization of activity (e.g., protection from anaphylaxis) assays, as described herein.

Non-limiting, exemplary in vitro assays for measuring binding activity are illustrated in Examples 4, herein. In Examples 4, the binding affinities and kinetic constants of human anti-Fel d1 antibodies were determined by surface plasmon resonance and the measurements were conducted on a T200 Biacore instrument.

The Fel d1 proteins or peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization. The antibodies specific for Fel d1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Epitope Mapping and Related Technologies

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The present invention includes anti-Fel d1 antibodies which interact with one or more amino acids found within one or more regions of chain 1 or chain 2 of the Fel d1 molecule including, e.g., chain 1 (chain A) as shown in SEQ ID NO: 392, or chain 2 (chain B) as shown in SEQ ID NO: 393, or within comparable regions of a recombinantly produced Fel d1 protein, as shown in any one of SEQ ID NOs: 385, 394, 395, 396 or 397. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned regions or segments of the Fel d1 molecule (e.g. a linear epitope in either chain 1 or chain 2, or in a region that spans both chain 1 and chain 2). Alternatively, the epitope may consist of a plurality of non-contiguous amino acids (or amino acid sequences) located within either or both of the aforementioned regions or segments of the Fel d1 molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in *Antibodies*, Harlow and Lane (Cold Spring Harbor Press, Cold Spring Harb., N.Y.). Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-Fel d1 antibodies or antigen-binding fragments thereof bind an epitope within any one or more of the regions exemplified in chain 1 or chain 2 of Fel d1, either in natural form, as exemplified in SEQ ID NO: 392 (chain 1) and SEQ ID NO: 393 (chain 2), or recombinantly produced, as exemplified in any of SEQ ID NOS: 385, 394, 395, 396, and 397, or to a fragment thereof. In certain embodiments, the antibodies of the invention, as shown in Table 1, interact with at least one amino acid sequence selected from the group consisting of amino acid residues ranging from about position 15 to about position 24 of SEQ ID NO: 396; amino acid residues ranging from about position 85 to about position 103 of SEQ ID NO: 396; amino acid residues ranging from about position 85 to about position 104 of SEQ ID NO: 396; amino acid residues ranging from about position 113 to about position 116 of SEQ ID NO: 396. These regions are further exemplified in SEQ ID NOs: 402, 403, 404, 412 and 426.

The present invention also includes anti-Fel d1 antibodies that bind to the same epitope, or a portion of the epitope, as any of the specific exemplary antibodies described herein in Table 1, or an antibody having the CDR sequences of any of the exemplary antibodies described in Table 1. Likewise, the present invention also includes anti-Fel d1 antibodies that compete for binding to Fel d1 or a Fel d1 fragment with any of the specific exemplary antibodies described herein in Table 1, or an antibody having the CDR sequences of any of the exemplary antibodies described in Table 1.

One can easily determine whether an antibody binds to the same epitope as, or competes for binding with, a reference anti-Fel d1 antibody by using routine methods known in the art. For example, to determine if a test antibody binds to the same epitope as a reference anti-Fel d1 antibody of the invention, the reference antibody is allowed to bind to a Fel d1 protein or peptide under saturating conditions. Next, the ability of a test antibody to bind to the Fel d1 molecule is assessed. If the test antibody is able to bind to Fel d1 following saturation binding with the reference anti-Fel d1 antibody, it can be concluded that the test antibody binds to a different epitope than the reference anti-Fel d1 antibody. On the other hand, if the test antibody is not able to bind to the Fel d1 molecule following saturation binding with the reference anti-Fel d1 antibody, then the test antibody may bind to the same epitope as the epitope bound by the reference anti-Fel d1 antibody of the invention.

To determine if an antibody competes for binding with a reference anti-Fel d1 antibody, the above-described binding methodology is performed in two orientations: In a first orientation, the reference antibody is allowed to bind to a Fel d1 molecule under saturating conditions followed by assessment of binding of the test antibody to the Fel d1 molecule. In a second orientation, the test antibody is allowed to bind to a Fel d1 molecule under saturating conditions followed by assessment of binding of the reference antibody to the Fel d1 molecule. If, in both orientations, only the first (saturating) antibody is capable of binding to the Fel d1 molecule, then it is concluded that the test antibody and the reference antibody compete for binding to Fel d1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-Fel d1 monoclonal antibody conjugated to a therapeutic moiety ("immunoconjugate"), such as an agent that is capable of reducing the severity of an allergic response to the Fel d1 allergen present in cat dander or on cats, or in an area of the environment where cats may reside, or to ameliorate at least one symptom associated with exposure to cats, cat dander or to the Fel d1 allergen, including rhinitis, conjunctivitis, or breathing difficulties, or the severity thereof. Such an agent may be a corticosteroid, a second different antibody to Fel d1, or a vaccine. The type of therapeutic moiety that may be conjugated to the Fel d1 antibody will take into account the condition to be treated and the desired therapeutic effect to be achieved. Alternatively, if the desired therapeutic effect is to treat the sequelae or symptoms associated with exposure to the Fel d1 allergen, or any other condition resulting from such exposure, such as, but not limited to, rhinitis or conjunctivitis, it may be advantageous to conjugate an agent appropriate to treat the sequelae or symptoms of the condition, or to alleviate any side effects of the antibodies of the invention. Examples of suitable agents for forming immunoconjugates are known in the art, see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin may be specific for chain 1 of Fel d1, or a fragment thereof, and the other arm of the immunoglobulin may be specific for chain 2 of Fel d1, or a second therapeutic target, or may be conjugated to a therapeutic moiety.

Certain exemplary embodiments of the present invention include a bi-specific antigen-binding molecule, which is a bi-specific antibody. Each antigen-binding domain of a bi-specific antibody comprises a heavy chain variable domain (HCVR) and a light chain variable domain (LCVR). The HCVR may also be referred to as a $V_H$ region, and the LCVR may also be referred to as a $V_L$ region. Typically, each HCVR and LCVR comprises three CDRs interspersed with four FRs, arranged from amino-terminus to carboxy-terminus in the following order: FR1, CDR1, FR2, CDR2, FR3, CDR3, FR4. The three CDRs within an HCVR may be referred to herein as HCDR1, HCDR2 and HCDR3; while the three CDRs within an LCVR may be referred to herein as LCDR1, LCDR2 and LCDR3.

In the bi-specific antigen-binding molecules of the present invention, each antigen-binding domain may comprise or consist of a full antibody molecule or an antigen-binding fragment of an antibody. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments that may be included in the bi-specific antigen-binding molecules of the present invention include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of a bi-specific antigen-binding molecule may contain at least one variable domain covalently linked to at least one constant domain. Non-limiting, exemplary configurations of variable and constant domains that may be found within an antigen-binding domain of a bi-specific antigen-binding molecule may include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; $V_L$-$C_H1$; (ix) $V_L$-$C_H2$; (X) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding domain of a bi-specific antigen-binding molecule may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The first antigen-binding domain and the second antigen-binding domain may be directly or indirectly connected to one another to form a bi-specific antigen-binding molecule. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing domain may be an Fc fragment or an amino acid sequence of 1 to about 200 amino acids in length containing at least one cysteine residues. In other embodiments, the multimerizing domain may be a cysteine residue, or a short cysteine-containing peptide. Other multimerizing domains include peptides or polypeptides comprising or consisting of a leucine zipper, a helix-loop motif, or a coiled-coil motif.

Any bi-specific antibody format or technology may be used to make the bi-specific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bi-specific antigen-binding molecule.

An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise a Y96F modification (by IMGT; Y436F by EU). Further modifications that may be found within the second $C_{H3}$ include: D16E, L18M, N44S, K52N, V57M, and V82I (by IMGT; D356E, L358E, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bi-specific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bi-specific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-Fel d1 antibodies or antigen-binding fragments thereof of the present invention. The administration of therapeutic compositions in accordance with the invention will be administered via a suitable route including, but not limited to, intravenously, subcutaneously, intramuscularly, intranasally, with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody of the present invention is used for treating the rhinitis or conjunctivitis associated with exposure to a cat, or to cat dander in an individual having a sensitivity to Fel d1, or for preventing an anaphylactic response to the cat allergen, or for lessening the severity of the allergic response, it is advantageous to intravenously administer the antibody of the present invention normally at a single dose of about 0.01 to about 30 mg/kg body weight, more preferably about 0.02 to about 7, about 0.03 to about 5, or about 0.05 to about 3 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousands Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

Due to their interaction with Fel d1, the present antibodies are useful for treating the primary response following exposure of an individual to a cat, cat dander or to an environment containing the Fel d1 protein, or at least one symptom associated with the allergic response, such as itchy eyes, conjunctivitis, rhinitis, wheezing, breathing difficulties, or for preventing a secondary response to the Fel d1 allergen, including a more serious anaphylactic response, or for lessening the severity, duration, and/or frequency of symptoms following reexposure to the cat allergen. Accordingly, it is envisioned that the antibodies of the present invention may be used prophylactically or therapeutically.

In yet a further embodiment of the invention the present antibodies are used for the preparation of a pharmaceutical composition for treating patients suffering from a sensitivity to cats, cat dander, cat hair or an extract thereof, and/or the Fel d1 protein. In yet another embodiment of the invention the present antibodies are used for the preparation of a pharmaceutical composition for reducing the severity of primary exposure to Fel d1, or for reducing the severity, duration of, and/or number of allergic responses to Fel d1.

In a further embodiment of the invention the present antibodies are used as adjunct therapy with any other agent useful for treating cat allergens, including corticosteroids, vaccines, allergen specific immunotherapy (SIT), or any other palliative therapy known to those skilled in the art.

Combination Therapies

Combination therapies may include an anti-Fel d1 antibody of the invention and any additional therapeutic agent that may be advantageously combined with an antibody of the invention, or with a biologically active fragment of an antibody of the invention.

For example, a second therapeutic agent may be employed to aid in reducing the allergic symptoms following exposure to a cat, cat dander, cat hair or an extract thereof, or Fel d1, or being exposed to an environment in which a cat resides, such as a corticosteroid. The antibodies may also be used in conjunction with other therapies, such as a vaccine specific for the Fel d1 allergen. The additional therapeutically active component(s) may be administered prior to, concurrent with, or after the administration of the anti-Fel d1 antibody of the present invention. For purposes of the present disclosure, such administration regimens are considered the administration of an anti-Fel d1 antibody "in combination with" a second therapeutically active component.

Administration Regimens

According to certain embodiments of the present invention, multiple doses of one or more anti-Fel d1 antibodies (an antibody combination) or a bi-specific antigen-binding molecule may be administered to a subject over a defined time course. The methods according to this aspect of the invention comprise sequentially administering to a subject multiple doses of an antibody, antibody combination, or a bi-specific antigen-binding molecule of the invention. As used herein, "sequentially administering" means that each dose of an antibody, antibody combination, or a bi-specific antigen-binding molecule is administered to the subject at a different point in time, e.g., on different days separated by a predetermined interval (e.g., hours, days, weeks or months). The present invention includes methods, which comprise sequentially administering to the patient a single initial dose of an antibody, antibody combination, or a bi-specific antigen-binding molecule, followed by one or more secondary doses of the antibody, and optionally followed by one or more tertiary doses of the antibody.

The terms "initial dose," "secondary doses," and "tertiary doses," refer to the temporal sequence of administration of an antibody, antibody combination, or a bi-specific antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of an antibody, antibody combination, or a bi-specific antigen-binding molecule, but generally may differ from one another in terms of frequency of administration. In certain embodiments, however, the amount of an antibody, antibody combination, or a bi-specific antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of an antibody, antibody combination, or a bi-specific antigen-binding molecule, which is administered to a patient prior to the administration of the very next dose in the sequence with no intervening doses.

The methods according to this aspect of the invention may comprise administering to a patient any number of secondary and/or tertiary doses of an antibody, antibody combination, or a bi-specific antigen-binding molecule that specifically binds Fel d1. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-Fel d1 antibodies of the present invention may also be used to detect and/or measure Fel d1 in a sample, e.g., for diagnostic purposes. It is envisioned that confirmation of an allergic response thought to be caused by Fel d1 may be made by measuring the presence of either Fel d1 through use of any one or more of the antibodies of the invention. Exemplary diagnostic assays for Fel d1 may comprise, e.g., contacting a sample, obtained from a patient, with an anti-Fel d1 antibody of the invention, wherein the anti-Fel d1 antibody is labeled with a detectable label or reporter molecule or used as a capture ligand to selectively isolate Fel d1 protein from patient samples. Alternatively, an unlabeled anti-Fel d1 antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure Fel d1 in a sample include enzyme-linked immunosorbent assay (ELISA), radioimmunoassay (RIA), and fluorescence-activated cell sorting (FACS).

Samples that can be used in Fel d1 diagnostic assays according to the present invention include any tissue or fluid sample obtainable from a patient, which contains detectable quantities of Fel d1 protein, or fragments thereof, under normal or pathological conditions. Generally, levels of Fel d1 in a particular sample obtained from a healthy/non-allergic patient (e.g., a patient not afflicted with a sensitivity associated with the presence of Fel d1) will be measured to initially establish a baseline, or standard, level of Fel d1. This baseline level of Fel d1 can then be compared against the levels of Fel d1 measured in samples obtained from individuals suspected of having a sensitivity to Fel d1 in cat dander, or symptoms associated with such condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Fel d1

An immunogen comprising any one of the following can be used to generate antibodies to Fel d1. In certain embodiments, the antibodies of the invention are obtained from mice immunized with a primary immunogen, such as full length natural Fel d1 (nFel d1), which may be purchased commercially (e.g., from Indoor Biotechnologies, # LTN-FD1-1), or isolated from cat hair or dander by multi-step column chromatography (See, for example, Chapman M D, et al. (1988), J. Immunol. 140:812-818), or which may be produced recombinantly (See GenBank accession numbers P30438, or NP_001041618.1 for the full length amino acid sequence of chain 1 of Fel d1 (also referred to as chain A or FELD1 A; also see SEQ ID NO: 392) and GenBank accession number P30440, or NP_001041619.1 for the full length amino acid sequence of chain 2 of Fel d1 (also referred to as chain B or FELD B; also see SEQ ID NO: 393), or fragments of either chain 1 or chain 2, or fragments from both chain 1 and chain 2 of the Fel d1 protein, followed by immunization with a secondary immunogen, or with an immunogenically active fragment of the natural protein. Animals may be immunized with either chain 1 protein alone or chain 2 protein alone, or with both chain 1 and chain 2 proteins, administered sequentially, or concurrently. Various constructs may be prepared using portions of chain 1 and chain 2 along with various linking or spacer strategies known to those skilled in the art. These constructs may be used alone, or in various combinations to elicit antibody responses in vivo. For example, recombinant Fel d1 constructs, such as those exemplified in SEQ ID NOs: 385, 394, 395, 396 or 397, or fragments thereof, may be used as immunogens.

In certain embodiments, the antibodies of the invention are obtained from mice immunized with a primary immunogen, such as a biologically active and/or immunogenic fragment of natural Fel d1, or DNA encoding the active fragment thereof. The fragment may be derived from the N-terminal or C-terminal domain of either chain 1 and/or chain 2 of Fel d1.

In certain embodiments, the recombinantly produced Fel d1 immunogen may be made by direct fusion of the two chains of Fel d1, as described in Kaiser et. al., to produce a fusion product that has a similar refolding pattern to that of natural Fel d1 (Kaiser, L. et al., (2003), J. Biol. Chem. 278(39):37730-37735). In certain embodiments, the immunogen may be a fusion protein such as that shown in the constructs of SEQ ID NOs: 385, 394, 395, 396 or 397, followed by immunization with a secondary immunogen, or with an immunogenically active fragment of the natural or recombinantly produced Fel d1.

In certain embodiments, the recombinant Fel d1 protein constructs used in the studies described herein are comprised of either i) Fel d1 B chain (chain 2) and Fel d1 A chain (chain 1) linked as a continuous, in-line fusion (with Fel d1 B chain at the N-terminus) or ii) a continuous, in-line fusion with Fel d1 A chain at the N-terminus followed by a flexible linker [(Gly4Ser)$_3$] followed by Fel d1 B. These constructs may also include a C-terminal tag (myc-myc-His6 or mouse IgG2a Fc region), as indicated below. The proteins were expressed in Chinese hamster ovary (CHO) cells. An exogenous signal sequence used to promote expression in CHO cells is not included in the sequence listings.

In certain embodiments, the immunogen may be a fusion protein comprising any one or more of the following: i) amino acid residues 18-109 of chain 2 of Fel d1 (See GenBank accession number P30440 and also SEQ ID NO: 393) fused via the C terminus directly with the N terminus of amino acid residues 23-92 of chain 1 of Fel d1 (See GenBank accession number P30438 and also SEQ ID NO: 392); ii) amino acid residues 23-92 of chain 1 of Fel d1 (See GenBank accession number P30438 and also SEQ ID NO: 392) fused via the C terminus to the N terminus of amino acid residues 18-109 of chain 2 of Fel d1 (See GenBank accession number P30440 and also SEQ ID NO: 393); iii) amino acid residues 18-109 of chain 2 of Fel d1 (See GenBank accession number NP_001041619.1) fused via the C terminus directly with the N terminus of amino acid residues 19-88 of chain 1 of Fel d1 (See GenBank accession number NP_001041618), such as the construct shown in SEQ ID NO: 394 or 396; iv) amino acid residues 19-88 of chain 1 of Fel d1 (See GenBank accession number NP_001041618.1) fused via the C terminus to the N terminus of amino acid residues 18-109 of chain 2 of Fel d1 (See GenBank accession number NP_001041619.1). See also SEQ ID NO: 395). In certain embodiments, the fusion protein may have a tag at the C terminal end of the construct, such as a myc-myc-hexahistidine tag (See SEQ ID NOs: 385, 396 or 397 for such constructs.). In related embodiments, the fusion protein may have a mouse Fc coupled at the C terminal end of the construct (See SEQ ID NOs: 394 or 395 for such constructs.). In certain embodiments, chains 1 and 2 are coupled via a linker known to those skilled in the art, e.g. (G$_4$S)$_3$ (See SEQ ID NOs: 395 and 397 for such a construct.).

In certain embodiments, antibodies that bind specifically to Fel d1 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of Fel d1 specific antibodies. In certain embodiments, any one or more of the above-noted regions of Fel d1, or fragments thereof may be used for preparing monospecific, bispecific, or multispecific antibodies.

The full length proteins, or fragments thereof, that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a Fel d1-specific immunoassay. When a desired immune response was achieved splenocytes were harvested and fused with mouse myeloma cells to preserve their viability and form hybridoma cell lines. The hybridoma cell lines were screened and selected to identify cell lines that produce Fel d1 specific antibodies. Using this technique, and the various immunogens described above, several anti-Fel d1, chimeric antibodies (i.e., antibodies possessing human variable domains and mouse constant domains) were obtained; certain exemplary antibodies generated in this manner were designated as H1M1230N, H1M1234N, H1M1241N, H2M1233N, H2M1236N, H2M1237N, and H2M1242N.

Anti-Fel d1 antibodies were also isolated directly from antigen-positive B cells without fusion to myeloma cells, as described in U.S. 2007/0280945A1, herein specifically incorporated by reference in its entirety. Using this method, several fully human anti-Fel d1 antibodies (i.e., antibodies possessing human variable domains and human constant domains) were obtained; exemplary antibodies generated in this manner were designated as follows: H4H2574P, H4H2590S, H4H2592B, H4H2594S, H4H2597P, H4H2606B, H4H2607B, H4H2608B, H4H2636P, H4H2645P, H4H2793P, H4H2797P and H4H2864P.

The biological properties of the exemplary antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected antibodies specific for Fel d1 and their corresponding antibody identifiers. Antibodies are typically referred to herein according to the following nomenclature: Fc prefix (e.g. "H4H", "H1M, "H2M"), followed by a numerical identifier (e.g. "1232" as shown in Table 1), followed by a "P" or "N" suffix. Thus, according to this nomenclature, an antibody may be referred to as, e.g. "H1M1232N". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs), which are indicated by the numerical identifiers shown in Table 1, will remain the same. Antibodies having the same numerical antibody designation, but differing by a letter suffix of N, B, S or P refer to antibodies having heavy and light chains with identical CDR sequences but with sequence variations in regions that fall outside of the CDR sequences (i.e., in the framework regions). Thus, N, B, S and P variants of a particular antibody have identical CDR sequences within their heavy and light chain variable regions but differ from one another within their framework regions.

TABLE 1

| Antibody Designation | AMINO ACID SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M1230N | 2 | 4 | 6 | 8 | 10 | 12 | 14 | 16 |
| H4H1232N | 18 | 20 | 22 | 24 | 26 | 28 | 30 | 32 |
| H1M1234N | 34 | 36 | 38 | 40 | 42 | 44 | 46 | 48 |
| H1M1241N | 50 | 52 | 54 | 56 | 58 | 60 | 62 | 64 |
| H4H1300N | 66 | 68 | 70 | 72 | 74 | 76 | 78 | 80 |
| H2M1233N | 82 | 84 | 86 | 88 | 90 | 92 | 94 | 96 |
| H2M1236N | 98 | 100 | 102 | 104 | 106 | 108 | 110 | 112 |
| H2M1237N | 114 | 116 | 118 | 120 | 122 | 124 | 126 | 128 |
| H4H1238N | 130 | 132 | 134 | 136 | 138 | 140 | 142 | 144 |
| H2M1242N | 146 | 148 | 150 | 152 | 154 | 156 | 158 | 160 |
| H4H1616N | 162 | 164 | 166 | 168 | 170 | 172 | 174 | 176 |
| H4H2574P | 178 | 180 | 182 | 184 | 186 | 188 | 190 | 192 |
| H4H2590S | 194 | 196 | 198 | 200 | 202 | 204 | 206 | 208 |
| H4H2592B | 210 | 212 | 214 | 216 | 218 | 220 | 222 | 224 |
| H4H2594S | 226 | 228 | 230 | 232 | 234 | 236 | 238 | 240 |
| H4H2597P | 242 | 244 | 246 | 248 | 250 | 252 | 254 | 256 |
| H4H2606B | 258 | 260 | 262 | 264 | 266 | 268 | 270 | 272 |
| H4H2607B | 274 | 276 | 278 | 280 | 282 | 284 | 286 | 288 |
| H4H2608B | 290 | 292 | 294 | 296 | 298 | 300 | 302 | 304 |
| H4H2636P | 306 | 308 | 310 | 312 | 314 | 316 | 318 | 320 |
| H4H2645P | 322 | 324 | 326 | 328 | 330 | 332 | 334 | 336 |
| H4H2793P | 338 | 340 | 342 | 344 | 346 | 348 | 350 | 352 |
| H4H2797P | 354 | 356 | 358 | 360 | 362 | 364 | 366 | 368 |
| H4H2864P | 370 | 372 | 374 | 376 | 378 | 380 | 382 | 384 |
| H4H2574B | 428 | 430 | 432 | 434 | 436 | 438 | 440 | 442 |
| H4H2597B | 444 | 446 | 448 | 450 | 452 | 454 | 456 | 458 |
| H4H2636B | 460 | 462 | 464 | 466 | 468 | 470 | 472 | 474 |
| H4H2645B | 476 | 478 | 480 | 482 | 484 | 486 | 488 | 490 |

Example 3

Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage ($V_H$, D, $J_H$, $V_K$, or $J_K$) was identified for each Heavy Chain Variable Region (HCVR) and Light Chain Variable Region (LCVR). Table 2 sets forth the gene usage for selected antibodies in accordance with the invention.

TABLE 2

| Antibody PID | Antibody Identifier HCVR/LCVR | HCVR | | | LCVR | |
|---|---|---|---|---|---|---|
| | | $V_H$ | D | $J_H$ | $V_K$ | $J_K$ |
| H1M1230N | 2/10 | 3-7 | 6-13 | 6 | 1-12 | 5 |
| H4H1232N | 18/26 | 3-21 | 2-15 | 6 | 1-27 | 2 |
| H1M1234N | 34/42 | 6-1 | 1-7 | 4 | 4-1 | 4 |
| H1M1241N | 50/58 | 3-21 | 2-2 | 6 | 1-17 | 4 |
| H4H1300N | 66/74 | 1-2 | 5-12 | 4 | 4-1 | 2 |
| H2M1233N | 82/90 | 3-33 | 6-19 | 4 | 1-5 | 1 |
| H2M1236N | 98/105 | 4-59 | 1-7 | 4 | 1-33 | 2 |
| H2M1237N | 114/122 | 3-33 | 6-19 | 4 | 1-5 | 1 |
| H4H1238N | 130/138 | 4-59 | 1-7 | 4 | 1-33 | 2 |
| H2M1242N | 146/154 | 3-21 | 5-12 | 4 | 1-5 | 1 |
| H4H1616N | 162/170 | 3-23 | 6-13 | 4 | 1-33 | 3 |
| H4H2574P | 178/186 | 4-39 | 6-19 | 3 | 3-20 | 2 |
| H4H2590S | 194/202 | 3-11 | 6-6 | 4 | 6-21 | 1 |
| H4H2592B | 210/218 | 3-11 | 1-26 | 4 | 6-21 | 1 |
| H4H2594S | 226/234 | 3-11 | 6-6 | 4 | 1-16 | 4 |
| H4H2597P | 242/250 | 3-11 | 6-6 | 4 | 6-21 | 1 |
| H4H2606B | 258/266 | 3-11 | 3-9 | 4 | 6-21 | 1 |
| H4H2607B | 274/282 | 3-11 | 1-26 | 4 | 1-17 | 2 |
| H4H2608B | 290/298 | 3-11 | 1-26 | 4 | 6-21 | 1 |
| H4H2636P | 306/314 | 3-23 | 1-1 | 4 | 1-5 | 4 |
| H4H2645P | 322/330 | 3-23 | ND | 1 | 1-16 | 3 |
| H4H2793P | 338/346 | 3-7 | 3-16 | 4 | 1-12 | 1 |

TABLE 2-continued

| Antibody PID | Antibody Identifier HCVR/LCVR | HCVR | | | LCVR | |
|---|---|---|---|---|---|---|
| | | $V_H$ | D | $J_H$ | $V_K$ | $J_K$ |
| H4H2797P | 354/362 | 3-33 | 5-12 | 3 | 1-16 | 3 |
| H4H2864P | 370/378 | 3-23 | 1-7 | 4 | 1-9 | 3 |

Example 4

Antibody Binding to Fel d1 as Determined by Surface Plasmon Resonance

Binding associative and dissociative rate constants ($k_a$ and $k_d$, respectively) and calculated equilibrium dissociation constants and dissociative half-lives ($K_D$ and $t_{1/2}$, respectively) for antigen binding to anti-Fel d1 monoclonal antibodies were determined using a real-time surface plasmon resonance biosensor (Biacore T200 or Biacore 2000) assay. The Biacore sensor surface was derivatized with either polyclonal rabbit anti-mouse antibody (GE Healthcare, # BR-1008-38) or with monoclonal mouse anti-human Fc antibody (GE Healthcare, # BR-1008-39) to capture anti-Fel d1 antibodies, expressed with mouse Fc (antibody ID prefix H1M, H2M, H2aM, H2bM) or human IgG4 Fc (antibody ID prefix H4H), respectively. For kinetic fits, at least two different concentrations (ranging from 390 pM to 67 nM) of natural Fel d1 (Indoor Biotech, # NA-FD1-2) or a recombinant version of the protein, Fel d1 (B-A)-mmH (SEQ ID NO: 396) were injected over the anti-Fel d1 monoclonal antibody-captured surface at 25° C. at a flow rate of 50 µl/min in running buffer (10 mM HEPES, 150 mM NaCl, 0.05% P20, 3 mM MgCl$_2$, 3 mM CaCl$_2$). Fel d1 (B-A)-mmH was expressed in Chinese hamster ovary (CHO) cells and is comprised of amino acids 18-109 of Fel d1 B (accession

P30440) fused in-line with amino acids 23-92 of Fel d1 A (accession #P30438) with a C-terminal myc-myc-hexahistidine tag. Antibody-antigen association was monitored for 3 to 5 minutes, and the dissociation of antigen from the captured monoclonal antibody (in running buffer alone at 25° C.) was monitored for 10 or 15 minutes. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D=k_d/k_a$ and $t_{1/2}=\ln(2)/k_d$. Binding parameters for different anti-Fel d1 monoclonal antibodies are tabulated in Table 3 and Table 4. Table 3 shows the Biacore affinities at 25° C. for natural Fel d1 binding to captured anti-Fel d1 monoclonal antibodies and Table 4 shows the Biacore affinities at 25° C. for recombinant Fel d1 binding to captured anti-Fel d1 monoclonal antibodies.

As shown in Table 3, 10 of the 25 antibodies tested exhibited $K_D$ values below 1 nM for binding to natural Fel d1, ranging from 207 pM to 982 pM. As shown in Table 4, 17 of the 25 antibodies tested exhibited $K_D$ values below 1 nM for binding to recombinant Fel d1, ranging from 144 pM to 924 pM. Two of the antibodies, H4H2574B and H4H2793P, bound to recombinant, but not natural Fel d1 under these experimental conditions

TABLE 3

| mAb Captured | $k_a$ (1/Ms) | $k_d$ (1/s) | $K_D$ (M) | $t_{1/2}$ (min) |
|---|---|---|---|---|
| H4H1232N | 1.60E+06 | 3.31E−04 | 2.07E−10 | 35 |
| H4H1238N | 3.83E+05 | 1.67E−03 | 4.37E−09 | 7 |
| H4H1300N* | 4.40E+04 | 2.11E−01 | 4.80E−06 | 0.05 |
| H4H1616N | 2.41E+05 | 1.24E−03 | 5.14E−09 | 9 |
| H1M1230N | 2.58E+05 | 8.69E−04 | 3.37E−09 | 13 |
| H1M1234N | 3.71E+05 | 6.79E−03 | 1.83E−08 | 2 |
| H2M1233N | 2.53E+05 | 3.53E−04 | 1.40E−09 | 33 |
| H2M1236N | 3.12E+05 | 1.42E−03 | 4.55E−09 | 8 |
| H2M1237N | 2.81E+05 | 2.76E−04 | 9.82E−10 | 42 |
| H1M1241N | 1.82E+05 | 6.62E−04 | 3.63E−09 | 17 |
| H2M1242N | 1.92E+05 | 6.04E−04 | 3.14E−09 | 19 |
| H4H2574B | NB | NB | NB | NB |
| H4H2590S | 1.23E+06 | 8.02E−04 | 6.55E−10 | 14 |
| H4H2592B | 1.14E+06 | 7.28E−04 | 6.41E−10 | 16 |
| H4H2594S | 1.10E+06 | 9.65E−04 | 8.78E−10 | 12 |
| H4H2597B | 2.31E+06 | 1.50E−03 | 6.50E−10 | 8 |
| H4H2606B | 9.24E+05 | 7.07E−04 | 7.65E−10 | 16 |
| H4H2607B | 2.97E+06 | 9.10E−04 | 3.07E−10 | 13 |
| H4H2608B | 5.16E+05 | 1.06E−03 | 2.05E−09 | 11 |
| H4H2636B | 2.24E+05 | 3.95E−04 | 1.77E−09 | 29 |
| H4H2793P | NB | NB | NB | NB |
| H4H2797P | 2.02E+05 | 7.13E−03 | 3.54E−08 | 2 |
| H4H2864P | 1.68E+06 | 1.35E−03 | 8.01E−10 | 9 |
| H4H2645P | 5.69E+05 | 2.61E−04 | 4.59E−10 | 44 |
| H4H2636P | 4.31E+05 | 4.48E−04 | 1.04E−09 | 26 |

*Because of the lower observed binding affinity, higher injected concentrations of natural Fel d1 (67 nM, 200 nM, and 600 nM) were used for this sample.

TABLE 4

| mAb Captured | $k_a$ (1/Ms) | $k_d$ (1/s) | $K_D$ (M) | $t_{1/2}$ (min) |
|---|---|---|---|---|
| H4H1232N | 1.79E+06 | 2.58E−04 | 1.44E−10 | 45 |
| H4H1238N | 7.35E+05 | 9.74E−04 | 1.33E−09 | 12 |
| H4H1300N* | 1.68E+05 | 2.28E−01 | 1.36E−06 | 0.05 |
| H4H1616N | 2.29E+05 | 1.88E−03 | 8.21E−09 | 6 |
| H1M1230N | 3.88E+05 | 5.10E−04 | 1.31E−09 | 23 |
| H1M1234N | 2.54E+05 | 1.42E−03 | 5.58E−09 | 8 |
| H2M1233N | 3.05E+05 | 1.66E−04 | 5.44E−10 | 70 |
| H2M1236N | 4.15E+05 | 2.32E−04 | 5.58E−10 | 50 |
| H2M1237N | 3.59E+05 | 1.65E−04 | 4.58E−10 | 70 |
| H1M1241N | 3.37E+05 | 1.12E−04 | 3.31E−10 | 104 |
| H2M1242N | 2.72E+05 | 1.22E−04 | 4.49E−10 | 94 |
| H4H2574B | 1.25E+05 | 3.73E−04 | 2.98E−09 | 31 |
| H4H2590S | 1.31E+06 | 4.16E−04 | 3.18E−10 | 28 |
| H4H2592B | 1.55E+06 | 5.56E−04 | 3.58E−10 | 21 |
| H4H2594S | 1.30E+06 | 5.21E−04 | 4.02E−10 | 22 |
| H4H2597B | 1.12E+06 | 5.58E−04 | 5.01E−10 | 21 |
| H4H2606B | 1.26E+06 | 4.86E−04 | 3.88E−10 | 24 |
| H4H2607B | 1.55E+06 | 5.63E−04 | 3.64E−10 | 21 |
| H4H2608B | 9.70E+05 | 5.89E−04 | 6.07E−10 | 20 |
| H4H2636B | 2.47E+05 | 2.28E−04 | 9.24E−10 | 51 |
| H4H2793P | 1.52E+05 | 1.95E−04 | 1.28E−09 | 59 |
| H4H2797P | 4.37E+05 | 2.05E−03 | 4.69E−09 | 6 |
| H4H2864P | 5.37E+05 | 3.09E−04 | 5.76E−10 | 37 |
| H4H2645P | 4.87E+05 | 1.79E−04 | 3.68E−10 | 65 |
| H4H2636P | 2.57E+05 | 2.35E−04 | 9.12E−10 | 49 |

*Because of the lower observed binding affinity, higher injected concentrations of recombinant Fel d1 (67 nM, 200 nM, and 600 nM) were used for this sample Example 5

Cross Competition of Anti-Fel d1 Antibodies for Binding to Natural (n) Fel d1

A binding experiment was performed using an Octet Red biosensor system (Fortebio Inc.) to determine cross-competition for a panel of 8 anti-Fel d1 antibodies binding to natural Fel d1 (nFel d1; Indoor Biotechnologies, #NA-FD1-2). The experiment was performed at 25° C. in HBST buffer (0.01 M HEPES pH7.4, 0.15M NaCl, 3 mM EDTA, 0.05% v/v Surfactant P20) containing 0.1 mg/mL BSA. A washing step with the HBST buffer was performed between each binding step, and plates were agitated during the binding and washing steps using an orbital plate shaker at 1000 rpm. A first anti-Fel d1 antibody (mAb-1) was captured for 2 minutes onto the anti-hFc biosensor surface from stock solutions of antibody at 10 ug/mL (final capture levels ~1.5 nm response units). The coated sensor tips were then blocked for 5 minutes with a 100 ug/mL solution of an irrelevant antibody. Sensor tips were then submerged into wells containing 500 nM of nFel d1 for 5 minutes, and then into wells containing 50 ug/mL solutions of a second anti-Fel d1 antibody (mAb-2). The mAb-2 solutions were supplemented with 100 ug/mL of an irrelevant antibody to minimize non-specific binding. The binding responses for mAb-2 binding to nFel d1 pre-complexed with mAb-1 were measured for the 8×8 antibody matrix (Table 5). Each binding value for mAb-2 binding to a different mAb-1/Fel d1 capture surface (down a column in Table 5) was subtracted by the mAb-1/Fel d1/mAb-2 self-competition value (where mAb-1=mAb-2; across the diagonal in Table 5). Values below 0.10 nm indicate cross-competition of mAb-1 and mAb-2 to a common binding site on Fel d1.

Four antibodies, H4H2636P, H4H1616N, H4H2645P, and H4H2864P, bi-directionally compete with each other for binding to nFel d1, but do not compete with any of the other anti-Fel d1 antibodies. Two antibodies, H4H1232N and H4H2597P, bi-directionally compete with each other for binding to nFel d1. Both H4H1232N and H4H2597P unidirectionally compete with H4H1300N. Bi-directional competition with H4H1300N could not be determined because H4H1300N did not pre-complex with nFel d1. H4H1238N did not compete with any of the anti-Fel d1 antibodies for binding to nFel d1.

TABLE 5

| mAb Captured | Amount of mAb-1 Captured +/- Std dev (nm) | Amount of 500 nM nFel d1 Bound +/- Std dev (nm) | Response of mAb-2 Binding to nFel d1 pre-complexed with mAb-1 (nm) | | |
|---|---|---|---|---|---|
| | | | H4H2636P | H4H1616N | H4H2645P |
| H4H2636P | 1.37 ± 0.07 | 0.09 ± 0.01 | 0.00 | 0.01 | 0.00 |
| H4H1616N | 1.21 ± 0.08 | 0.09 ± 0.01 | -0.01 | 0.00 | -0.01 |
| H4H2645P | 1.31 ± 0.07 | 0.10 ± 0.01 | 0.00 | 0.01 | 0.00 |
| H4H2864P | 1.41 ± 0.09 | 0.08 ± 0.01 | -0.01 | 0.01 | -0.01 |
| H4H2597P | 1.26 ± 0.08 | 0.06 ± 0.01 | 0.55 | 0.40 | 0.55 |
| H4H1232N | 1.51 ± 0.09 | 0.08 ± 0.02 | 0.76 | 0.54 | 0.75 |
| H4H1238N | 1.28 ± 0.08 | 0.08 ± 0.01 | 0.63 | 0.43 | 0.62 |
| H4H1300N | 1.29 ± 0.09 | -0.02 ± 0.01 | 0.06 | 0.06 | 0.05 |

| mAb Captured | Response of mAb-2 Binding to nFel d1 pre-complexed with mAb-1 (nm) | | | | |
|---|---|---|---|---|---|
| | H4H2864P | H4H2597P | H4H1232N | H4H1238N | H4H1300N |
| H4H2636P | 0.00 | 0.27 | 0.29 | 0.28 | 0.38 |
| H4H1616N | -0.01 | 0.18 | 0.18 | 0.21 | 0.20 |
| H4H2645P | -0.01 | 0.29 | 0.31 | 0.31 | 0.26 |
| H4H2864P | 0.00 | 0.27 | 0.30 | 0.30 | 0.33 |
| H4H2597P | 0.54 | 0.00 | -0.03 | 0.56 | -0.03 |
| H4H1232N | 0.71 | 0.00 | 0.00 | 0.73 | -0.02 |
| H4H1238N | 0.62 | 0.65 | 0.76 | 0.00 | 0.60 |
| H4H1300N | 0.06 | 0.03 | 0.02 | 0.07 | 0.00 |

Example 6

Effect of Anti-Fel d1 Antibodies in a Passive Cutaneous Anaphylaxis (PCA) In Vivo Model The passive cutaneous anaphylaxis (PCA) in vivo model was used to assess in vivo mast cell degranulation. The model involves intradermal injection of an allergen-specific antiserum into a local area on the skin followed by intravenous injection of an antigen along with a dye. The allergic reaction causes capillary dilatation and increased vascular permeability at the site of sensitization, resulting in preferential accumulation of dye at this site. The dye can be extracted from the tissue and quantitated spectrophotometrically. Dye extravasation into tissue sensitized with test antiserum is compared to extravasation into tissue sensitized with a non-relevant antiserum.

Antisera were generated by immunizing Balb/c mice with 5 µg natural Fel d1 protein purified from cat hair extract (Indoor Biotechnologies, # LTN-FD1-1), 5 µg of crude peanut allergen extract (Greer Laboratories, # XPF171D3A25), or 1250 of Bioequivalent allergy units (BAU) of standardized cat hair extract (Greer Laboratories, #GTE3A01) in a solution of 1 mg/ml of alum (Pierce, #77161) in 1× phosphate buffered saline. Two weeks later (day 14) sensitized mice were boosted with doses of allergen identical to those used for the initial immunization. Two weeks after the boost (day 28), mice were sacrificed and serum was collected. Total IgE concentration in the isolated antisera was determined by ELISA. The final concentration of antiserum was diluted to 2400 ng/mL IgE in 1× phosphate buffered saline.

To determine the effect of anti-Fel d1 antibodies on mast cell degranulation in the PCA model, prior to ear sensitization with antiserum generated as described above, groups of Balb/c mice were first injected subcutaneously with either a human IgG4 isotype control antibody, an anti-Fel d1 antibody, or a combination of anti-Fel d1 antibodies at doses of 5 mg/kg (total antibody dose, 2.5 mg/kg of each antibody) for single point experiments unless otherwise indicated or at concentrations ranging from 0.06 mg/kg to 2 mg/kg for dose-ranging experiments. Three days after pre-treatment with antibodies, one group of mice ("natural Fel d1 group") was sensitized by intradermal injection with 10 µl of natural Fel d1-derived antiserum or 10 µl of peanut-derived antiserum (negative control) into the right and left ears, respectively, of each mouse. A second group of mice ("cat extract group") was sensitized with 20 µL of cat hair extract-derived antiserum or 20 µL of peanut-derived antiserum (negative control) into the right and left ears, respectively, of each mouse. Twenty-four hours after sensitization, mice in the natural Fel d1 group were challenged by intravenous injection (100 µL per mouse) of a solution of 0.25 µg/mL natural Fel d1 (Indoor Biotechnologies, # LTN-FD1-1) dissolved in 1× phosphate buffered saline containing 0.5% (w/v) Evan's blue dye (Sigma, # E2129). Similarly, 24 hours after sensitization, mice in the cat extract group were challenged with 250BAU of standardized cat hair extract [standardized cat hair extract (Greer Laboratories, #GTE3A01)] dissolved in 1× phosphate buffered saline containing 0.5% (w/v) Evan's blue dye (Sigma, # E2129). One hour after antigen challenge, mice were sacrificed, ears were excised and placed in 1 mL formamide and incubated for 3 days at 56° C. to extract the Evan's blue dye from the tissue. Ear tissue was then removed from the formamide, blotted to remove excess liquid and weighed. Two hundred microliter aliquots of each formamide extract were transferred to 96 well plates in duplicate. Absorbance of the resulting supernatants was measured at 620 nm. The OD was converted to Evan's blue dye concentration using a standard curve. The average concentration of Evan's blue dye extravasated into the tissue of the antisera-sensitized ear (normalized by ear tissue weight) was calculated for the group treated with the isotype control antibody and defined as F(isotype,avg). The reduction in Evan's blue dye extravasation resulting from antibody pre-treatment was calculated per mouse by subtracting the amount of Evan's blue dye for the antibody-treated group's Fel d1 or extract sensitized ear, defined as F(mAb,i), from F(isotype,avg). This number was then divided by the difference between F(isotype,avg) and the dye amount for the antibody-treated group's peanut sensitized ear [P(mAb, i)] and multiplied by 100 to give the overall percent reduction in dye extravasation for each mouse (% Reduction).

% Reduction (per mouse)=100*[$F$(isotype,avg)−$F$(mAb,$i$)]/[$F$(isotype,avg)−$P$(mAb,$i$)]

The average percent reduction in dye leakage was then calculated for each antibody group. Results, expressed as (mean±SD) of percent Evan's blue reduction are shown in Table 6 and Table 7 for the natural Fel d1 group and in Table 8 for the cat hair extract group.

As shown in Table 6, seven groups of mice from the natural Fel d1 group, when treated with specific combinations of anti-Fel d1 antibodies at fixed concentrations, exhibited reductions in dye extravasations ranging from 79% to 103% compared to mice receiving control antibody. Mice treated with H4H2590S/H4H1238N, H4H2590S/H4H2574P, or H4H1232N/H4H1616N pairwise antibody combinations exhibited less than 3% reduction in dye extravasation compared to mice receiving control antibody, demonstrating that not all anti-Fel d1 antibodies tested in this model were efficacious.

In addition, dose-ranging experiments were performed with mice from the natural Fel d1 group, as shown in Table 7. Single antibodies were not as effective at reducing dye extravasation as the anti-Fel d1 antibody combinations at the tested doses.

A specific pair of anti-Fel d1 antibodies (H4H2636P and H4H1232N) at multiple dose levels, as well as each of these anti-Fel d1 antibodies alone at a single (highest) dose level, was further tested in the PCA model using mice that were sensitized and challenged with cat hair extract as shown in Table 8. At 2 mg/kg, these single anti-Fel d1 antibodies alone were not as efficacious at reducing dye extravasation as a combination of the two antibodies. The combination of H4H2636P and H4H1232N at both 2 mg/kg and 1 mg/kg reduced dye extravasation by more than 90% as compared with the isotype control in the PCA model using cat hair extract as the antigen.

All reductions that were statistically significant ($p<0.05$) compared to isotype control as determined by two-way ANOVA with Bonferroni's post-test are noted with an asterisk (*). The number of mice used per group (n) is noted within parentheses in the tables.

TABLE 6

| Antibody | % Reduction in Dye Extravasation |
|---|---|
| H4H1232N + H4H1238N* (n = 5) | 87 ± 8 |
| H4H1232N + H4H2645B* (n = 5) | 87 ± 29 |
| H4H1232N + H4H2636B* (n = 5) | 89 ± 23 |
| H4H1232N + H4H2864P* (n = 5) | 79 ± 27 |
| H4H1232N + H4H1238N + H4H1300N + H4H1616N* (n = 5) | 103 ± 16 |
| H4H1232N + H4H1616N (n = 5)§ | 3 ± 92 |
| H4H2590S + H4H1238N (n = 5) | 0 ± 74 |
| H4H2597P + H4H2636P*,** (n = 5) | 89 ± 4 |
| H4H2597P + H4H2645P*,** (n = 5) | 85 ± 36 |
| H4H2590S + H4H2574P (n = 5) | 0 ± 129 |

§ 10 mg/kg total antibody concentration;
**0.5 mg/kg total antibody concentration

TABLE 7

| | Percent Reduction in Dye Extravasation | | | | |
|---|---|---|---|---|---|
| Antibodies used | 1 mg/kg | 0.5 mg/kg | 0.25 mg/kg | 0.125 mg/kg | 0.06 mg/kg |
| Study 1 | | | | | |
| H4H1232N + H4H2636P | 84 ± 16* (n = 15) | 53 ± 41* (n = 15) | 53 ± 40* (n = 15) | 19 ± 32 (n = 15) | |
| H4H1232N | 24 ± 61 (n = 15) | | | | |
| H4H2636P | 0 ± 44 (n = 15) | | | | |
| Study 2 | | | | | |
| H4H1232N + H4H2645P | | 66 ± 29 (n = 10) | 49 ± 37 (n = 10) | 22 ± 36 (n = 10) | 0.26 ± 0.28 (n = 10) |
| H4H1232N | | 6 ± 6 (n = 10) | | | |
| H4H2645P | | 14 ± 14 (n = 10) | | | |
| Study 3 | | | | | |
| H4H1232N + H4H2864P | | 93 ± 10* (n = 10) | 50 ± 33* (n = 9) | 49 ± 42* (n = 10) | 11 ± 28 (n = 10) |
| H4H1232N | | 0 ± 45 (n = 10) | | | |
| H4H2864P | | 0 ± 35 (n = 10) | | | |
| Study 4 | | | | | |
| H4H1232N + H4H1238N | | 46 ± 46 (n = 10) | 60 ± 19* (n = 10) | 48 ± 53* (n = 10) | 0 ± 47 (n = 10) |
| H4H1232N | | 21 ± 57 (n = 10) | | | |
| H4H1238N | | 35 ± 36 (n = 10) | | | |

TABLE 7-continued

| | Percent Reduction in Dye Extravasation | | | | |
|---|---|---|---|---|---|
| Antibodies used | 1 mg/kg | 0.5 mg/kg | 0.25 mg/kg | 0.125 mg/kg | 0.06 mg/kg |
| Study 5 | | | | | |
| H4H2597P + H4H2636P | | 90 ± 8* | 81 ± 16* (n = 5) | 43 ± 21 (n = 5) | 14 ± 32 (n = 5) |
| H4H2597P | | 0 ± 49 (n = 5) | | | |
| H4H2636P | | 28 ± 51 (n = 5) | | | |
| Study 6 | | | | | |
| H4H2597P + H4H2645P | | 64 ± 41* (n = 10) | 27 ± 25 (n = 5) | 18 ± 39 (n = 5) | 0 ± 16 (n = 5) |
| H4H2597P | | 7 ± 31 (n = 5) | | | |
| H4H2645P | | 0 ± 26 (n = 5) | | | |

TABLE 8

| | Percent Reduction in Dye Extravasation | | | |
|---|---|---|---|---|
| Antibodies used | 2 mg/kg | 1 mg/kg | 0.5 mg/kg | 0.25 mg/kg |
| H4H1232N + H4H2636P | 93 ± 4* (n = 5) | 97 ± 2* (n = 5) | 85 ± 13* (n = 5) | 40 ± 51 (n = 5) |
| H4H1232N | 66 ± 9* (n = 5) | | | |
| H4H2636P | 40 ± 55 (n = 5) | | | |

Example 7

Effect of Anti-Fel d1 Antibodies in a Lung Inflammation In Vivo Model

The lung inflammation in vivo mouse model is used to assess allergen induced lung inflammation and mucus accumulation that could be associated with asthma or rhinoconjuctivitis. The model involves repeated intranasal administration of an allergen into previously allergen-sensitized mice. The allergen-associated inflammation can cause increases in lung mucus accumulation, eosinophil migration into the lung, serum total IgE, and allergen specific IgG1 levels.

Balb/c mice were intraperitoneally immunized with 1 ug of natural Fel d 1 protein purified from cat hair extract (Indoor Biotechnologies, #LTN-FD1-1) in a solution of 1 mg/mL of alum (Pierce, #77161) in 1× phosphate buffered saline. Seven days later, sensitized mice were boosted intraperitoneally with 1 ug of natural Fel d 1 in a solution of 1 mg/mL alum in 1× phosphate buffered saline. On days 17, 21, and 25, groups of mice (n=5) were injected subcutaneously with a human IgG4 isotype control antibody or a 1:1 combination of anti-Fel d 1 antibodies, H4H1232N and H4H2636P, at 20 mg/kg (total antibody dose). On days 20, 24, and 28, mice were intranasally challenged with 0.05 ug of natural Fel d 1 diluted in 20 uL of 1× phosphate buffered saline. Control mice were challenged with 20 uL of 1× phosphate buffered saline on the same days. On day 32, all mice were sacrificed and their lungs were harvested. Experimental dosing and treatment protocol for groups of mice are shown in Table 9.

To determine circulating total IgE and Fel d 1 specific IgG1 in the serum of the mice, serum samples were collected for each mouse via terminal cardiac puncture using a 27G1/2 1 mL TB syringe (Becton Dickinson, #309306) with a needle attached. Blood samples were placed into BD Microtainer® serum separator tubes (Becton Dickinson, #365956), centrifuged, and then the serum was transferred to a fresh tube for storage until analysis.

To determine the total IgE concentration in the serum samples for each mouse, a sandwich ELISA OPTEIA kit (BD Biosciences, #555248) was used according to the manufacturer's instructions. Serum samples were diluted and incubated with anti-IgE capture antibody coated on 96-well plates. Total IgE was detected by biotinylated anti-mouse IgE secondary antibody. Purified horseradish peroxidase (HRP)-labeled mouse IgE was used as a standard. The chromogen 3,3',5,5'-tetramethylbenzidine (TMB) (BD OPTEIA substrate reagent set, BD, #555214) was used to detect HRP activity. A stop solution of 1M sulfuric acid was then added, and absorbance at 450 nm was measured on a Molecular Devices SpectraMax M5 plate reader. Data analysis was performed using Prism™ software. The mean amounts of circulating IgE levels in serum for each experimental group are expressed as ng/mL (±SEM) as shown in Table 10. Mice challenged with Fel d 1 intranasally when treated with the combination of anti-Fel d 1 antibodies exhibited a significant decrease in the amount of circulating IgE [6683 (±1394) ng/mL] compared to mice receiving isotype control antibody [14080 (±1505) ng/mL].

To determine the Fel d 1 specific IgG1 levels in the serum samples from each mouse, an ELISA was utilized. Fel d 1 coated plates were incubated with serially diluted mouse serum samples, followed by incubation with anti-mouse IgG1-HRP conjugated antibody (BD Biosciences, #559626). All samples were developed with a TMB solution and analyzed as described above. Relative levels of circulating IgG1 in serum were represented as titer units (titer units were calculated by multiplying the measured OD by a dilution factor required to achieve OD450 that was greater than two times background). The mean circulating Fel d 1-specific IgG1 levels in serum for each experimental group are expressed as titer×$10^3$ (±SEM) as shown in Table 11. Mice challenged with Fel d 1 intranasally when treated with the combination of anti-Fel d 1 antibodies exhibited a significant decrease in the amount of Fel d 1-specific IgG1 levels in serum [titer of 105.3 (±31.33)×$10^3$] when compared to mice receiving isotype control antibody [titer of 526.1 (±144.0)×$10^3$].

Lung Harvest for Cell Infiltrate Analysis:

After exsanguination, the right lung from each mouse was removed and placed into a small petri dish containing Dulbecco's Modified Eagle Medium (DMEM) (Irvine Scientific, #9033) and chopped into cubes that were approximately 2 to 3 mm in size. The cubes were then transferred to a tube containing a solution of 20 μg/mL DNAse (Roche, #10104159001) and 0.7 U/mL Liberase TH (Roche, #05401151001) diluted in Hank's Balanced Salt Solution (HBSS) (Gibco, #14025) and placed into a 37° C. water bath for 20 minutes with vortexing every 5 minutes. This reaction was then stopped by adding ethylenediaminetetraacetic acid (EDTA) (Gibco, #15575) at a final concentration of 10 mM. Each lung was mashed, filtered through a 70 μm filter, centrifuged, and then lung pellet was resuspended in 4 mL of ACK lysing buffer (Gibco, #10492) to remove red blood cells. After a 3 minute room temperature incubation, DMEM was added to deactivate the ACK buffer. The cell suspensions were centrifuged, and the cell pellets were then resuspended into 10 mL of MACS buffer solution [a mixture of Militenyi auto MACS Rinsing Solution (Militenyi Biotec, #130-091-222) and MACS BSA (Militenyi Biotec, #130-091-376)]. The resuspended samples were filtered through a 70 μm filter and 1×10$^6$ cells were plated into a 96-well V-bottom plate. Cells were then centrifuged and the pellets were resuspended in purified rat anti-mouse CD16/CD32 Fc Block, (BD Biosciences Clone: 2.4G2, #553142) diluted in MACS Buffer for 15 minutes at 40° C. The cells were washed twice and were then incubated in the appropriate antibody mixture (described in Table 12) diluted in MACS buffer for 30 minutes at 4° C. protected from light. After antibody incubation, the cells were washed twice in MACS buffer and resuspended in BD cytofix (BD Biosciences, #554655) for 15 minutes at 4° C. while being protected from light. The cells were washed, resuspended in MACS buffer and were then transferred to BD FACS tubes (BD Biosciences, #352235) for analysis of eosinophils by flow cytometry. Eosinophils were defined as cells that were CD45$^+$, GR1$^-$, CD11c$^{lo}$, SiglecF$^{hi}$. Data are expressed as frequency of eosinophils in CD45$^+$ cells (±SEM) in Table 13.

Mice challenged with Fel d 1 intranasally when treated with the combination of anti-Fel d 1 antibodies exhibited a significant decrease in the frequency of eosinophils in the CD45+ cell population as compared to mice receiving no antibody (67% decrease) or receiving isotype control antibody (46% decrease) as shown in Table 13.

Lung Harvest for Histological Analysis:

After exsanguination, the left lungs were removed and placed into tubes containing a 5 mL solution of 4% (w/v) paraformaldehyde (Boston Bioproducts, # BM-155) in 1× phosphate buffered saline and stored at room temperature for 3 days. Lung samples were then blotted dry and transferred to tubes containing 70% ethanol for histological analysis. The samples were sent to Histoserv, Inc (Germantown, Md.) for sectioning and periodic acid Schiff (PAS) staining.

Approximately 35 digital images across the full area of each PAS-stained lung section were acquired using a Zeiss Axioplan 2 Imaging light microscope with a Zeiss AxioCam MRc camera. A whole lung image was then constructed from the smaller images and analyzed using ImageJ software with the aid of a color threshold plugin. The regions of mucus accumulation in the bronchial lumen were identified and quantitated through a user-chosen color threshold and normalized to the total area of the lumen that was identified and quantitated by a separate color threshold setting. Percentage of the bronchial lumen occupied by mucus accumulation for each lung was expressed as [(mucus area/lumen area)×100] and was calculated for each treatment group. Results, expressed as mean percent lung obstruction (±SEM) are shown in Table 14.

Mice treated with the combination of anti-Fel d 1 antibodies exhibited a trend towards reduced mucus accumulation in the lung bronchi (5.21+/−0.81% mucus accumulation) compared to mice receiving control antibody (10.81+/−1.13% mucus accumulation) in the lung inflammation model as shown in Table 14. No differences were observed in bronchial lumen size or overall lung size between the groups of mice.

TABLE 9

Experimental dosing and treatment protocol for groups of Balb/c mice

| Group | Intraperitoneal Immunization (D0) and boost (D7) | Intranasal Challenge (D20, D24 & D28) | Subcutaneous antibody injection (D17, D21, D25) |
|---|---|---|---|
| 1 | 1 ug Fel d 1 in 1 mg Alum | 1X phosphate buffered saline | No antibody |
| 2 | 1 ug Fel d 1 in 1 mg Alum | .05 ug/20 uL Fel d 1 | No antibody |
| 3 | 1 ug Fel d 1 in 1 mg Alum | .05 ug/20 uL Fel d 1 | Human IgG4 isotype control |
| 4 | 1 ug Fel d 1 in 1 mg Alum | .05 ug/20 uL Fel d 1 | H4H1232N + H4H2636P |

TABLE 10

Total Circulating IgE levels in Mouse Serum

| Mouse group | Mean circulating IgE levels (ng/mL) (±SEM) |
|---|---|
| 1. Saline Challenge, no antibody treatment (n = 19) | 2661 (±361)*** |
| 2. Fel d 1 challenge, no antibody treatment (n = 20) | 11711 (±1518) |
| 3. Fel d 1 challenge, human IgG4 Isotype control treatment (n = 20) | 14080 (±1505) |
| 4. Fel d 1 challenge, anti-Fel d 1 antibody treatment (n = 20) | 6683 (±1394)*** |

Note:
Statistical significance compared to isotype control determined by one-way ANOVA with Tukey's multiple comparison post-test is indicated (***p < 0.001). Outliers, defined as greater than 2 standard deviations from the mean, were removed from the study.

TABLE 11

Circulating Fel d 1-specific IgG1 in Mouse Serum

| Mouse group | Mean circulating Fel d 1 - specific IgG1 levels (Titer × 10$^3$) (±SEM) |
|---|---|
| 1. Saline Challenge, no antibody treatment (n = 19) | 81.79 (±22.07)*** |
| 2. Fel d 1 challenge, no antibody treatment (n = 19) | 720.1 (±102.8) |
| 3. Fel d 1 challenge, human IgG4 Isotype control treatment (n = 19) | 526.1 (±144.0) |
| 4. Fel d 1 challenge, anti-Fel d 1 antibody treatment (n = 19) | 105.3 (±31.33)** |

Note:
Statistical significance compared to isotype control determined by one-way ANOVA with Dunn's multiple comparison post-test is indicated (*p < 0.001, p < 0.01). Outliers, defined as greater than 2 standard deviations from the mean, were removed from the study.

TABLE 12

Antibodies Used for Flow Cytometry Analysis

| Antibody | Fluorochrome | Company | Catalog Number | Concentration |
|---|---|---|---|---|
| CD11c | APC | BDBiosciences | 550261 | 1/100 |
| CD45 | PerCP Cy5.5 | BDBiosciences | 552950 | 1/800 |
| F4/80 | Pacific Blue | eBiosciences | 48-4801-82 | 1/200 |
| Siglec-F | PE | BDBiosciences | 552126 | 1/100 |
| Ly6G (Gr-1) | APC-eFluor780 | eBiosciences | 47-5931-82 | 1/200 |

TABLE 13

Frequency of eosinophils in $CD45^+$ cells as determined by flow cytometry

| Mouse group | Mean Frequency of Eosinophils in CD45+ cells (±SEM) |
|---|---|
| 1. Saline Challenge, no antibody treatment (n = 19) | 1.05 (±0.10)*** |
| 2. Fel d 1 challenge, no antibody treatment (n = 20) | 6.28 (±0.59)** |
| 3. Fel d 1 challenge, human IgG4 Isotype control treatment (n = 19) | 3.89 (±0.60) |
| 4. Fel d 1 challenge, anti-Fel d 1 antibody treatment (n = 19) | 2.08 (±0.23)* |

Note:
Statistical significance compared to isotype control determined by one-way ANOVA with Tukey's multiple comparison post-hoc test is indicated (*$p < 0.001$, $p < 0.01$, *$p < 0.05$). Outliers, defined as greater than 2 standard deviations from the mean, were removed from the analysis.

TABLE 14

Lung Obstruction (mucus area/lumen area, %)

| Mouse group | Lung Obstruction (±SEM) |
|---|---|
| 1. Saline Challenge, no antibody treatment (n = 19) | 0.48 (±0.10)*** |
| 2. Fel d 1 challenge, no antibody treatment (n = 20) | 10.31 (±0.75) |
| 3. Fel d 1 challenge, human IgG4 Isotype control treatment (n = 19) | 10.18 (±1.13) |
| 4. Fel d 1 challenge, anti-Fel d 1 antibody treatment (n = 20) | 5.21 (±0.81) |

Note:
Statistical significance compared to isotype control determined by one-way ANOVA with Dunn's multiple comparison post-hoc test is indicated (*$p < 0.001$, $p < 0.01$, *$p < 0.05$). Outliers, defined as greater than 2 standard deviations from the mean, were removed from the analysis.

Example 8

Hydrogen-Deuterium Exchange Epitope Mapping

In order to determine the epitopes of Fel d1 (a heterodimeric protein comprised of Fel d1 chain A and FELD1 chain B) recognized by two anti-Fel d1 antibodies, hydrogen-deuterium (H/D) exchange studies were performed for each antibody co-complexed with Fel d1. Prior to the H/D exchange experiments, CHO cell-expressed recombinant Fel d1 comprised of amino acids 18-109 of Feld 1 chain B (GenBank accession number NP_001041619.1) fused in-line with amino acids 19-88 of FELD1 A (GenBank accession #NP_001041618.1) expressed with a C-terminal myc-myc-hexahistidine tag and with a D27G mutation (Fel d1 B-A-mmH; SEQ ID: 396) was deglycosylated at 37° C. for 4 hours under native conditions using PNGase F (New England BioLabs, #0704). For this study, two anti-FELD1 antibodies (H4H1232N and H4H2636P) were covalently attached to N-hydroxysuccinimide (NHS) agarose beads (GE Lifescience, #17-0906-01) according to the manufacturer's protocol.

To map the Fel d1 B-A-mmH binding epitope recognized by H4H1232N, two sets of H/D exchange experiments were carried out (all binding and exchange reactions carried out at room temperature). The first experiment used an 'on-solution/off-beads' format (on-exchange in solution followed by off-exchange on beads). For the on-exchange, the deglycosylated Fel d1 B-A-mmH protein was deuterated for 5 and 10 minutes (in two separate sub-experiments) in PBS buffer at pH 7.4 prepared with $D_2O$ (PBS-D) and was then bound to the H4H1232N beads during a 2-minute incubation in PBS-D. The co-complex of Fel d1 B-A-mmH-bound to H4H1232N beads was then washed with PBS buffer at pH 7.4 prepared with $H_2O$ (PBS-H) and incubated in PBS-H for half of the on-exchange time (off-exchange), allowing only the epitopes on Fel d1 B-A-mmH protected by the binding of the H4H1232N antibody to remain deuterated. After the off-exchange, the bound Fel d1 B-A-mmH was eluted from the beads using an ice-cold 0.1% aqueous trifluoroacetic acid (TFA) solution. The eluted Fel d1 B-A-mmH was then digested with immobilized pepsin (Thermo Scientific, #20343) for 5 minutes at 4° C. The resulting peptides were desalted at 4° C. using ZipTip chromatographic pipette tips (Millipore, #ZTC18S096) according to the manufacturer's protocol and then immediately analyzed on an UltrafleXtreme matrix assisted laser desorption ionization time of flight (MALDI-TOF) mass spectrometer (MS).

The second experiment is referred to as the 'on-beads/off-beads' (on-exchange on beads followed by off-exchange on beads). For this experiment, the deglycosylated Fel d1 B-A-mmH was first bound to the H4H1232N beads, and then incubated for 5 or 10 minutes (in separate sub-experiments) in PBS-D to allow on-exchange. The following steps (off-exchange, pepsin digestion, and MS analysis) were carried out as described for the 'on-solution/off-beads' procedure above. The centroid values or average mass-to-charge ratios (m/z) of all the detected peptides were calculated and compared between the on-solution/off-beads and on-beads/off-beads experiments. Peptides exhibiting increased mass after the on-solution/off-beads procedure compared to the on-beads/off-beads procedure include amino acids within the Fel d1 protein protected from exchange as a result of antibody binding and therefore reveal binding epitope regions.

The H/D exchange experiment for Fel d1 B-A-mmH binding to the anti-Fel d1 antibody H4H2636P was performed using the same procedure described above for H4H1232N, but with H4H2636P beads replacing the H4H1232N beads.

A comparison of the centroid m/z values for all the peptides detected in the H/D exchange experiment of Fel d1 B-A-mmH with H4H1232N are shown in Table 15. These peptides were identified by liquid chromatography-matrix assisted laser desorption ionization (LC-MALDI) MS. Most peptic peptides gave similar centroid values (differences <0.3 m/z units) for both the on-solution/off-beads and on-beads/off-beads protocols, for each of two different on-exchange and off-exchange times. However, three peptides with amino acids spanning from 85-103, 85-104, and 113-127 of Fel d1B-A-mmH (SEQ ID NO: 396) had differences in m/z centroid values >0.3 in both the 5 minute and 10 minute experiments. The differences between these centroid values from the on-solution/off-beads and on-beads/off-beads protocol are highlighted in bold in Table 15. Since another peptide, amino acids 117-127 of SEQ ID NO: 396, did not show deuteron retention after off-exchange, the region of protection from exchange in the 113-127 peptide can be reduced to residues 113-116 of SEQ ID NO: 396. The two regions, residues 85-104 (SEQ ID NO: 403) and 113-116 (SEQ ID NO: 426), are protected from full off-exchange as a result of H4H1232N binding to Fel d1 B-A-mmH after on-exchange. Therefore, these two segments are defined by the H/D exchange method as a discontinuous epitope for antibody H4H1232N binding to the Fel d1 B-A-mmH protein.

Comparisons of the centroid m/z values for the peptides detected in the H/D exchange experiment of Fel d1 B-A-mmH complexed with H4H2636P are shown in Table 16. Only one peptide, amino acids 15-24 of FELD1 B-A-mmH, exhibited an increase in the centroid m/z values >0.3 m/z for the on-solution/off-beads condition compared to the on-beads/off-beads condition, indicating that this segment was protected from full off-exchange by the binding of H4H2636P. The centroid value differences greater than 0.3 m/z are highlighted in bold in Table 16. Therefore, amino acids within this 15-24 region (SEQ ID NO: 412) based on the H/D exchange method include an epitope for antibody H4H2636P binding to the Fel d1 B-A-mmH protein.

TABLE 15

The Effect on H/D Exchange of H4H1232N Binding Fel d1B-A-mmH as Measured by Centroid m/z Values of Peptic Peptides

| | Experiment I 5 min on-/2.5 min off-exchange | | | Experiment II 10 min on-/5 min off-exchange | | | |
|---|---|---|---|---|---|---|---|
| Residues of FELDB-A-MMH | on-solution/ off beads | on-beads/ off-beads | D | on-solution/ off beads | on-beads/ off-beads | D | Peptide |
| 1-11 | 1318.37 | 1318.29 | 0.09 | 1318.27 | 1318.27 | -0.01 | VKMAETCPIFY (SEQ ID NO: 398) |
| 55-61 | 759.89 | 759.83 | 0.06 | 759.87 | 759.86 | 0.01 | ISRVLDG (SEQ ID NO: 399) |
| 55-62 | 873.04 | 873.02 | 0.02 | 873.02 | 873 | 0.02 | ISRVLDGL (SEQ ID NO: 400) |
| 55-64 | 1103.37 | 1103.39 | -0.03 | 1103.36 | 1103.36 | -0.01 | ISRVLDGLVM (SEQ ID NO: 401) |
| 85-103 | 2084.38 | 2083.75 | 0.63 | 2084.28 | 2083.83 | 0.45 | LKLNTLGREICP AVKRGVD (SEQ ID NO: 402) |
| 85-104 | 2197.63 | 2196.99 | 0.64 | 2197.73 | 2197.21 | 0.52 | LKLNTLGREICP AVKRGVDL (SEQ ID NO: 403) |
| 113-127 | 1721.91 | 1721.33 | 0.58 | 1722.22 | 1721.53 | 0.69 | YVEQVAQYKAL PVVL (SEQ ID NO: 404) |
| 117-127 | 1201.47 | 1201.48 | -0.01 | 1201.56 | 1201.46 | 0.1 | VAQYKALPVVL (SEQ ID NO: 405) |
| 128-141 | 1606.43 | 1606.26 | 0.16 | 1606.55 | 1606.29 | 0.26 | ENARILKNCVDA KM (SEQ ID NO: 406) |
| 153-170 | 1920.33 | 1920.25 | 0.09 | 1920.37 | 1920.38 | -0.01 | LDKIYTSPLCGP GGEQKL (SEQ ID NO: 407) |
| 183-196 | 1672.54 | 1672.59 | -0.04 | 1672.54 | 1672.51 | 0.03 | ISEEDLSGHHHH HH (SEQ ID NO: 408) |
| 183-199 | 1903.91 | 1903.95 | -0.03 | 1903.95 | 1903.92 | 0.03 | ISEEDLSGHHHH HHSSG (SEQ ID NO: 409) |

TABLE 15-continued

The Effect on H/D Exchange of H4H1232N Binding Fel d1B-A-mmH as Measured by Centroid m/z Values of Peptic Peptides

| Residues of FELDB-A-MMH | Experiment I 5 min on-/2.5 min off-exchange | | | Experiment II 10 min on-/5 min off-exchange | | | Peptide |
|---|---|---|---|---|---|---|---|
| | on-solution/ off beads | on-beads/ off-beads | D | on-solution/ off beads | on-beads/ off-beads | D | |
| 186-199 | 1574.44 | 1574.44 | 0.01 | 1574.44 | 1574.47 | -0.03 | EDLSGHHHHHH SSG (SEQ ID NO: 410) |

TABLE 16

The Effect on H/D Exchange of H4H2636P Binding to Fel d1B-A-mmH as Measured by Centroid m/z Values of Peptic Peptides

| Residues of FELDB-A-MMH | Experiment I 5 min on-/2.5 min off-exchange | | | Experiment II 10 min on-/5 min off-exchange | | | Peptide |
|---|---|---|---|---|---|---|---|
| | on-solution/ off beads | on-beads/ off-beads | D | on-solution/ off beads | on-beads/ off-beads | D | |
| 1-11 | 1318.47 | 1318.48 | -0.01 | 1318.5 | 1318.47 | 0.03 | VKMAETCPIFY (SEQ ID NO: 411) |
| 15-24 | 1049.53 | 1048.6 | 0.94 | 1049.51 | 1048.71 | 0.79 | FAVANGNELL (SEQ ID NO: 412) |
| 55-61 | 759.85 | 759.89 | -0.04 | 759.87 | 759.88 | -0.01 | ISRVLDG (SEQ ID NO: 413) |
| 55-62 | 873.06 | 873.01 | 0.05 | 873.06 | 873.04 | 0.02 | ISRVLDGL (SEQ ID NO: 414) |
| 55-64 | 1103.39 | 1103.36 | 0.03 | 1103.42 | 1103.43 | -0.01 | ISRVLDGLVM (SEQ ID NO: 415) |
| 85-103 | 2083.63 | 2083.63 | 0 | 2083.67 | 2083.62 | 0.04 | LKLNTLGREICP AVKRGVD (SEQ ID NO: 416) |
| 85-104 | 2196.67 | 2196.74 | -0.07 | 2196.8 | 2196.78 | 0.02 | LKLNTLGREICP AVKRGVDL (SEQ ID NO: 417) |
| 113-127 | 1721.28 | 1721.27 | 0.01 | 1721.19 | 1721.21 | -0.02 | YVEQVAQYKAL PVVL (SEQ ID: 418) |
| 117-127 | 1201.55 | 1201.53 | 0.02 | 1201.55 | 1201.59 | -0.04 | VAQYKALPVVL (SEQ ID NO: 419) |
| 120-127 | 903.18 | 903.12 | 0.06 | 903.14 | 903.14 | -0.01 | YKALPVVL (SEQ ID NO: 420) |
| 128-141 | 1606.41 | 1606.34 | 0.08 | 1606.57 | 1606.46 | 0.11 | ENARILKNCVDA KM (SEQ ID NO: 421) |
| 153-170 | 1920.29 | 1920.23 | 0.06 | 1920.24 | 1920.36 | -0.13 | LDKIYTSPLCGP GGEQKL (SEQ ID NO: 422) |

TABLE 16-continued

The Effect on H/D Exchange of H4H2636P Binding to Fel d1B-A-mmH as Measured by Centroid m/z Values of Peptic Peptides

| Residues of FELDB-A-MMH | Experiment I 5 min on-/2.5 min off-exchange | | | Experiment II 10 min on-/5 min off-exchange | | | Peptide |
|---|---|---|---|---|---|---|---|
| | on-solution/ off beads | on-beads/ off-beads | D | on-solution/ off beads | on-beads/ off-beads | D | |
| 183-196 | 1672.56 | 1672.59 | -0.02 | 1672.58 | 1672.54 | 0.04 | ISEEDLSGHHHH HH (SEQ ID NO: 423) |
| 183-199 | 1903.9 | 1903.89 | 0.01 | 1903.94 | 1903.93 | 0.02 | ISEEDLSGHHHH HHSSG (SEQ ID NO: 424) |
| 186-199 | 1574.4 | 1574.37 | 0.03 | 1574.41 | 1574.37 | 0.04 | EDLSGHHHHHH SSG (SEQ ID NO: 425) |

Example 9

Generation of Bi-Specific Antibodies

Description of the Fel d 1 Bispecific Antibodies Produced

Bi-specific antibodies comprising heavy and light chain binding domains from pairs of certain of the anti-Fel d1 antibodies described in the present invention were constructed using standard methodologies. The anti-Fel d1 antibodies used to construct the bi-specific antibodies of this example were obtained by immunizing a VelocImmune® mouse with a primary immunogen, such as full length natural Fel d1, which may be purchased commercially (e.g., from Indoor Biotechnologies, # LTN-FD1-1), or isolated from cat hair or dander by multi-step column chromatography (See, for example, Chapman M D, et al. (1988), J. Immunol. 140:812-818), or which may be produced recombinantly (See GenBank accession numbers P30438, or NP_001041618.1 for the full length amino acid sequence of chain 1 of Fel d1 (also referred to as chain A or FELD1 A; also see SEQ ID NO: 392) and GenBank accession number P30440, or NP_001041619.1 for the full length amino acid sequence of chain 2 of Fel d1 (also referred to as chain B or FELD B; also see SEQ ID NO: 393), or fragments of either chain 1 or chain 2, or fragments from both chain 1 and chain 2 of the Fel d1 protein, followed by immunization with a secondary immunogen, or with an immunogenically active fragment of the natural protein. In one embodiment, the immunogen used is exemplified in SEQ ID NO: 394 (in line fusion of Fel d1 Chain-2-Chain1-mFc) or SEQ ID NO: 395 (fusion of Fel d1 Chain 1 using a linker and Chain 2-mFc).

The bi-specific antibodies produced in accordance with the present Example comprise two antigen-binding domains (i.e. "binding arms 1 and 2").

One of the bi-specific antibodies, designated H4H3467D comprises a common kappa light chain on both Fab arms, derived from the antibody H4H2864P (SEQ ID NO: 378). One Fab arm of H4H3467D utilizes the heavy chain variable region ($V_H$) from the antibody H4H2864P (SEQ ID NO: 370), while the other Fab arm utilizes the $V_H$ region from H4H1232N (SEQ ID NO: 18).

A second bi-specific antibody of the invention, designated H4H8751 D, comprises a common kappa light chain on both Fab arms, derived from the antibody H4H2636P (SEQ ID NO: 314). One Fab arm of H4H8751 D utilizes the $V_H$ region from H4H2636P (SEQ ID NO: 306), while the other Fab arm utilizes the $V_H$ region from H4H1232N (SEQ ID NO: 18).

Table 17 below provides the component parts of the antigen-binding domains of the two bi-specific antibodies made in accordance with Example 9. The amino acid sequence identifiers for the various heavy chain and light chain variable regions that were derived from the parental antibodies (used to prepare the bi-specific antibodies) are also provided in Table 17.

TABLE 17

Component parts of the two arms of the bi-specific antibodies produced

| | Parental Antibody Identifier from which Bi-specific Sequence Derived | | | |
|---|---|---|---|---|
| | Arm 1 Antigen Binding Domain | | Arm 2 Antigen Binding Domain | |
| Bispecific Identifier | HCVR | LCVR | HCVR | LCVR |
| H4H3467D | H4H2864P SEQ ID NO: 370 | H4H2864P SEQ ID NO: 378 | H4H1232N SEQ ID NO: 18 | H4H2864P SEQ ID NO: 378 |
| H4H8751D | H4H2636P SEQ ID NO: 306 | H4H2636P SEQ ID NO: 314 | H4H1232N SEQ ID NO: 18 | H4H2636D SEQ ID NO: 314 |

Tables 18A and 18B below set forth the amino acid sequence identifiers for the various heavy chain variable regions (Table 18A) and the light chain variable regions (Table 18B) and their corresponding complementarity determining region sequences (CDRs) for the two bi-specific antibodies described herein.

TABLE 18A

HCVR and HCDR Sequence Identifiers for bi-specific antibodies produced

| Bi-specific Ab Identifier | Parent Ab from which sequences derived | SEQ ID NOs | | | |
|---|---|---|---|---|---|
| | | HCVR | HCDR1 | HCDR2 | HCDR3 |
| H4H3467D | H4H2864P (Arm 1) | 370 | 372 | 374 | 376 |
| | H4H1232N (Arm 2) | 18 | 20 | 22 | 24 |
| H4H8751D | H4H2636P (Arm 1) | 306 | 308 | 310 | 312 |
| | H4H1232N (Arm 2) | 18 | 20 | 22 | 24 |

TABLE 18B

LCVR and LCDR Sequence Identifiers for bi-specific antibodies produced

| Bi-specific Ab Identifier | Parent Ab from which sequences derived | SEQ ID NOs | | | |
|---|---|---|---|---|---|
| | | LCVR | LCDR1 | LCDR2 | LCDR3 |
| H4H3467D | H4H2864P (Arm 1) | 378 | 380 | 382 | 384 |
| | H4H2864P (Arm 2) | 378 | 380 | 382 | 384 |
| H4H8751D | H4H2636P (Arm 1) | 314 | 316 | 318 | 320 |
| | H4H2636P (Arm 2) | 314 | 316 | 318 | 320 |

Biacore Analysis of Bi-Specific Antibodies to Determine Association and Dissociation Values Binding association and dissociation rate constants ($k_a$ and $k_d$, respectively), equilibrium dissociation constants and dissociation half-lives ($K_D$ and $t_{1/2}$, respectively) for natural Fel d 1 (subsequently referred to as nFel d 1) binding to purified anti-Fel d 1 monospecific and bispecific antibodies were determined using a real-time surface plasmon resonance biosensor assay on a Biacore 2000 instrument. On a CM5 chip, using the EDC-NHS chemistry, the Biacore sensor surface was derivatized with a monoclonal mouse anti-human Fc antibody (GE, # BR-1008-39) to capture anti-Fel d 1 monospecific and bispecific antibodies. All the Biacore binding studies were performed at 25° C. in HBSP+ running buffer (0.01M HEPES pH 7.4, 0.15M NaCl, 3 mM $CaCl_2$, 3 mM $MgCl_2$, 0.05% v/v Surfactant P20). Different concentrations of nFel d 1 (Indoor Biotech, # NA-FD1-2) (ranging from 600 nM to 2.34 nM, 6-fold dilutions) prepared in HBSP+ running buffer were injected over the anti-Fel d 1 antibody captured surface at a flow rate of 50 µL/min. Association of nFel d 1 to the captured monoclonal antibodies was monitored for 4 minutes and the dissociation of nFel d 1 in HBSP+ running buffer was monitored for 7 minutes. Kinetic association ($k_a$) and dissociation ($k_d$) rate constants were determined by fitting the real-time sensorgrams to a 1:1 binding model with mass transport limitation using Scrubber 2.0c curve fitting software. Binding dissociation equilibrium constants ($K_D$) and dissociative half-lives ($t_{1/2}$) were then calculated from the kinetic rate constants as: $K_D$ (M)=$k_d/k_a$ and $t_{1/2}$ (min)=[ln2/(60*$k_d$)].

Binding kinetics of nFel d1 binding to different anti-Fel d 1 mono-specific and bi-specific antibodies at 25° C. are shown in Table 19. The three monospecific anti-Fel d 1 antibodies bound to nFel d1 with $K_D$ values ranging from 155 pM to 1.6 nM. The two bi-specific anti-Fel d1 antibodies, H4H3467D and H4H8751D, bound to nFel d1 with $K_D$ values of 250 pM and 347 pM respectively.

TABLE 19

Binding Kinetics of anti-Fel d1 mono-specific and bi-specific antibodies binding to nFel d 1 at 25° C.

| AbPID | Amount of mAb Captured (RU) | 600 nM nFel d 1 Bound (RU) | $k_a$ (1/Ms) | $k_d$ (1/s) | $K_D$ (M) | t½ (min) |
|---|---|---|---|---|---|---|
| H4H2864N | 277 | 48 | 9.16E+05 | 9.47E−04 | 1.03E−09 | 12 |
| H4H2636N | 280 | 54 | 3.14E+05 | 5.02E−04 | 1.60E−09 | 23 |
| H4H1232N | 259 | 42 | 3.05E+06 | 4.72E−04 | 1.55E−10 | 24 |
| H4H3467D | 278 | 35 | 2.85E+06 | 7.12E−04 | 2.50E−10 | 16 |
| H4H8751D | 300 | 30 | 1.79E+06 | 6.20E−04 | 3.47E−10 | 19 |

To determine the in vivo efficacy of the anti-Fel d 1 bi-specifics compared with their mono-specific parental antibodies, these antibodies along with an isotype control antibody were tested in the PCA in vivo model using natural Fel d 1 for both sensitization and challenging, which was previously described (see Example 6). Antibodies in this study were administered at a concentration of 1 mg/kg total antibody (0.5 mg/kg of each antibody was used when two antibodies were administered simultaneously) using 8 mice per experimental group. The data for each experimental group expressed as percent reduction in dye extravasation±SD are shown in Table 20.

The mono-specific antibodies H4H1232N and H4H2864P caused a 67 (±26)% and an 81 (±26)% reduction in dye extravasation, respectively. The combination of the mono-specific antibodies, H4H1232N and H4H2864P, caused a 98 (±3.5)% reduction in dye extravasation, while the bi-specific, H4H3467D, composed of the mono-specific antibodies, H4H1232N and H4H2864P, caused a 93 (±11)% reduction in dye extravasation.

The mono-specific antibodies H4H1232N and H4H2636P caused a 64 (±33)% and an 8.7 (±79)% reduction in dye extravasation, respectively, in another experiment. The combination of the mono-specific antibodies, H4H1232N and H4H2636P, caused a 90 (±15)% reduction in dye extravasation, while the bi-specific, H4H8751 D, composed of the mono-specific antibodies, H4H1232N and H4H2636P, caused a 77 (±20)% reduction in dye extravasation.

TABLE 20

Effect of anti-Fel d 1 bispecific antibodies and their parental mono-specific antibodies in the passive cutaneous anaphylaxis (PCA) in vivo model

| Antibody | % Reduction in Dye Extravasation ± SD |
|---|---|
| H4H1232N | 67 ± 26**** |
| H4H2864P | 81 ± 26**** |
| H4H3467D | 93 ± 11**** |
| H4H1232N + H4H2864P | 98 ± 3.5**** |
| H4H1232N$^a$ | 64 ± 33*** |
| H4H2636P$^a$ | 8.7 ± 79 |
| H4H8751D$^a$ | 77 ± 20**** |
| H4H1232N + H4H2636P$^a$ | 90 ± 15**** |

$^a$Experiments performed on a separate day

Statistical significance compared to isotype control determined by two-way ANOVA with Bonferroni's multiple comparison post-test is indicated (*= $p < 0.001$ and **= $p < 0.00001$)

What is claimed is:

1. A nucleic acid molecule encoding a human monoclonal antibody, or a fragment thereof that binds specifically to Fel d1, wherein the antibody comprises the three heavy chain complementarity determining regions (CDRs) (HCDR1, HCDR2 and HCDR3) contained within a heavy chain variable region (HCVR) amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354 and 370; and the three light chain CDRs (LCDR1, LCDR2 and LCDR3) contained within the light chain variable region (LCVR) amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362 and 378.

2. The nucleic acid molecule of claim 1, wherein the nucleic acid encodes an antibody or fragment thereof comprising a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354 and 370.

3. The nucleic acid molecule of claim 1, wherein nucleic acid encodes the antibody or fragment thereof comprising a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362 and 378.

4. The nucleic acid molecule of claim 1, wherein nucleic acid encodes the antibody or fragment thereof comprising a HCVR/LCVR amino acid sequence pair of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362 and 370/378.

5. An expression vector comprising the nucleic acid molecule encoding a human monoclonal antibody, or a fragment thereof that binds specifically to Fel d1, according to claim 1.

6. A method of producing a Fel d1 antibody or antigen-binding fragment thereof comprising the steps of introducing the expression vector of claim 5 into an isolated host cell, growing the cell under conditions permitting production of the antibody or antibody fragment, and recovering the antibody or antibody fragment so produced.

7. The method of claim 6, wherein the host cell is a CHO cell.

8. An isolated host cell containing the expression vector of claim 5.

* * * * *